(12) United States Patent
Banwell et al.

(10) Patent No.: US 7,173,019 B2
(45) Date of Patent: Feb. 6, 2007

(54) LINKED CYCLITOLS AND THEIR POLYSULFATED DERIVATIVES

(75) Inventors: Martin Gerhardt Banwell, Aranda (AU); Ligong Liu, Sunnybank (AU); Christopher Richard Parish, Campbell (AU); Craig Geoffrey Freeman, Rivett (AU)

(73) Assignee: The Australian National University, Acton (AU)

( * ) Notice: Subject to any disclaimer, the term of this patent is extended or adjusted under 35 U.S.C. 154(b) by 160 days.

(21) Appl. No.: 10/398,662

(22) PCT Filed: Jul. 4, 2002

(86) PCT No.: PCT/AU02/00884

§ 371 (c)(1),
(2), (4) Date: Apr. 8, 2003

(87) PCT Pub. No.: WO03/004454

PCT Pub. Date: Jan. 16, 2003

(65) Prior Publication Data

US 2004/0019021 A1  Jan. 29, 2004

(30) Foreign Application Priority Data

Jul. 4, 2001  (AU) .................................... PR6128

(51) Int. Cl.
*A66K 31/66* (2006.01)
*A61K 31/255* (2006.01)
*A61K 31/185* (2006.01)
*A61K 31/13* (2006.01)

(52) U.S. Cl. ............... 514/114; 514/517; 514/553; 514/660

(58) Field of Classification Search .......... 514/114, 514/517, 553, 660
See application file for complete search history.

(56) References Cited

FOREIGN PATENT DOCUMENTS

WO  97/09053  3/1997
WO  WO 97/09053 *  3/1997

OTHER PUBLICATIONS

Paul et al., Novel O- and N-Linked Inositol Oligomers: A New class of Unnatural *Saccharide mimics*, Synthesis, 2001, 6, 952-960.*

*Primary Examiner*—Thurman Page
*Assistant Examiner*—Chukwuma Nwaonicha
(74) *Attorney, Agent, or Firm*—Buchanan Ingersoll PC

(57) ABSTRACT

The invention relates to compounds of the following formula (I). In these compounds, $R_1$, $R_2$, $R_3$ and $R_4$ are each independently a substituted or unsubstituted cyclitol with a ring comprising six carbon atoms, or hydrogen, substituted or unsubstituted alkyl, cycloalkyl, aryl, acyl, alkyloxycarbonyl, or alkylaminocarbonyl. At least two of $R_1$, $R_2$, $R_3$ and $R_4$ comprise the substituted or unsubstituted cyclitol. The linker can be any one of the following: $-(CH_2)_w-$, $-(CH_2)_x-C_6H_4-(CH_2)_x-$, $-(CH_2)_y-NR_5-(CH_2)_y-$, and $-(CH_2)_z-HCR_6-(CH_2)_z-$; wherein: w, x, y and z are independently an integer having a value of 0–10; $R_5$ is a substituted or unsubstituted cyclitol with a ring comprising six carbon atoms; and, $R_6$ is $-OH$, $-OSO_3Na$, $-OSO_3Na$ substituted with alkyl, cycloalkyl or aryl, or substituted or unsubstituted alkyl, cycloalkyl or aryl. The compounds can also include substituted or unsubstituted cyclitol carbamides with the linker bond at the carbamide nitrogen. In other embodiments, the invention provides pharmaceutical compositions which include the compounds, and use of the compounds in the prevention or treatment in a mammalian subject of a disorder resulting from angiogenesis, metastasis, inflammation and/or coagulation/thrombosis

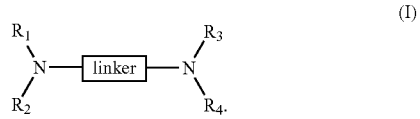

21 Claims, 4 Drawing Sheets

OTHER PUBLICATIONS

Bernhard J. Paul, et al., "Novel O- and N-Linked Inositol Oligomers: A New Class of Unnatural *Saccharide mimics*", Synthesis 2001, No. 6, pp. 952-956, ISSN 0039-7881, New York.

Xun Xie et al., "Inhibition of Selection-Mediated Cell Adhesion and Prevention of Acute Inflammation by Nonanticoagulant Sulfated Saccharides", The Journal of Biological Chemistry, vol. 275, No. 44, pp. 34818-34825, Nov. 3, 2003.

Tomas Hudlicky et al., "Biocatalysis as the Strategy of Choice in the Exhaustive Enantiomerically Controlled Synthesis of Conduritos", J. Chem. Soc. Perkin Trans., pp. 2907-2918, 1991.

Supplementary European Search Report dated Nov. 28, 2005.

* cited by examiner

LINKED CYCLITOLS AND THEIR POLYSULFATED DERIVATIVES

TECHNICAL FIELD

The invention that is the subject of this application lies in the area of compounds that mimic the structure of certain carbohydrates. More particularly, the invention lies in the area of heparanoid mimetics.

Specifically, the invention relates to compounds comprising at least two linked cyclitol moieties and polysulfated derivatives of these compounds. The invention also relates to methods for the preparation of the compounds, compositions comprising the compounds, and use of the compounds and compositions thereof for the anti-angiogenic, anti-metastatic and/or anti-inflammatory treatment of a mammalian subject. The invention further relates to the use of the compounds and compositions thereof as an anti-anticoagulant and/or anti-thrombotic agent in the treatment of a mammalian subject having a condition amenable to treatment with such agents.

BACKGROUND OF THE INVENTION

Carbohydrate-based, and particularly oligosaccharide-based, drugs and vaccines are attracting increasing attention because of the enormous potential they offer for the treatment of a broad range of disease states. This potential derives, at least in part, from the intimate involvement of carbohydrates in many biological processes including, inter alia, cell-to-cell recognition, cell adhesion, neural cell development and tumour metastasis. Whilst developments in this therapeutic area continue apace, the presence of glycosidic linkages in most of such compounds renders them vulnerable to hydrolytic cleavage. As a consequence they often posses unfavourable metabolic profiles that may restrict their use in, for example, oral applications. In principle, such problems might be overcome by employing glycominmetics particularly those embodying pseudo-sugars (wherein a pyranosyl- or furanosyl-ring oxygen has been replaced by a methylene unit) or related cyclitols in place of one or more of the "normal" monosaccharide residues. Despite the consequent potential of pseudo-sugars and cyclitols, remarkably few oligosaccharide analogues incorporating more than one such residue are known.

The applicant has previously identified a range of sulfated oligosaccharides with efficacy as, inter alia, anti-angiogenic, anti-proliferative and anti-thrombotic agents. One sulfated oligo-saccharide was found to be particularly potent and is now undergoing clinical trials. This oligosaccharide is phosphomannopentaose sulfate (hereafter "PI-88") and is described in International Patent Application No. PCT/AU96/00238 (Publication No. WO 96/33726). The utility of PI-88 as an anti-angiogenic, anti-proliferative and anti-thrombotic agent is also described in WO 96/33726 while other indications of PI-88 and related sulfated oligo-saccharides are given in the international applications by the present applicant having the application numbers PCT/AU98/00151 (Publication No. WO 98/40081) and PCT/AU98/00707 (Publication No. WO 99/11273).

With regard to pseudo-sugars and cyclitols, B. J. Paul, T. A. Martinot, J. Willis and T. Hudlicky in *Synthesis*, 2001, p 952, reported the preparation of novel O- and N-linked inositol oligomers by chemoenzymatic means and highlighted the potential of these products as a new class of unnatural saccharide mimics. The inventors considered, in the light of this work by Paul et al., that it might be possible to develop methods for the rapid construction of other linked cyclitols, particularlypseudo-sugar based analogues of PI-88.

OBJECTS OF THE INVENTION

It is an object of the invention to provide novel linked cyclitols that have utility as heparanoid mimetics.

It is a further object of the invention to provide effective synthetic routes for the preparation of the subject linked cyclitols.

SUMMARY OF THE INVENTION

According to a first embodiment of the invention, there is provided a compound of the formula

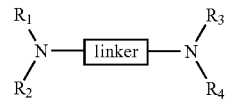

wherein:

$R_1$, $R_2$, $R_3$ and $R_4$ are independently a substituted or unsubstituted cyclitol with a ring comprising six carbon atoms, or hydrogen, substituted or unsubstituted alkyl, cycloalkyl, aryl, acyl, aroyl, alkyloxycarbonyl, or alkylaminocarbonyl, with the proviso that at least two of $R_1$, $R_2$, $R_3$ and $R_4$ comprise said substituted or unsubstituted cyclitol; or $R_1$ and $R_3$ are independently a substituted or unsubstituted cyclitol carbamide with a ring comprising six carbon atoms with the linker bond at the carbamide nitrogen, and $R_2$ and $R_4$ are independently hydrogen, substituted or unsubstituted alkyl, cycloalkyl or aryl; and the linker is selected from the group consisting of —(CH$_2$)$_w$—, —(CH$_2$)$_x$—C$_6$H$_4$—(CH$_2$)$_x$—, —(CH$_2$)$_y$—NR$_5$—(CH$_2$)$_y$—, and —(CH$_2$)$_z$—HCR$_6$—(CH$_2$)$_z$—; wherein: w, x, y and z are independently an integer having a value of 0–10; $R_5$ is a substituted or unsubstituted cyclitol with a ring comprising six carbon atoms; and, $R_6$ is —OH, —OSO$_3$Na, —OSO$_3$Na substituted with alkyl, cycloalkyl or aryl, or substituted or unsubstituted alkyl, cycloalkyl or aryl; and wherein each substituent on said substituted cyclitol is independently selected from:

(a) phosphoryl groups such as phosphate, thiophosphate —O—P(S)(OH)$_2$; phosphate esters —O—P(O)(OR)$_2$; thiophosphate esters —O—P(S)(OR)$_2$; phosphonate —O—P(O)OHR; thiophosphonate —O—P(S)OHR; substituted phosphonate —O—P(O)OR$_1$R$_2$; substituted thiophosphonate —O—P(S)OR$_1$R$_2$; —O—P(S)(OH)(SH); and cyclic phosphate;

(b) other phosphorus containing compounds such as phosphoramidite —O—P(OR)—NR$_1$R$_2$; and phosphoramidate —O—P(O)(OR)—NR$_1$R$_2$;

(c) sulphur groups such as —O—S(O)(OH), —O—S(O)$_2$(OH), RO—S(O)$_3^-$, —SH, —SR, —S(→O)—R, S(O)$_2$R, RO—S(O)$_2^-$, —O—SO$_2$NH$_2$, —O—SO$_2$R$_1$R$_2$ or sulphamide —NHSO$_2$NH$_2$;

(d) amino groups such as —NHR, —NR$_1$R$_2$, —NHAc, —NHCOR, —NH—O—COR, —NHSO$_3$, —NHSO$_2$R, —N(SO$_2$R)$_2$, and/or amidino groups such as —NH—C(=NH)NH$_2$ and/or ureido groups such as —NH—CO—NR$_1$R$_2$ or thiouriedo groups such as —H—C(S)—NH$_2$;

(e) substituted hydroxy groups such as —OR$_3$, where R$_3$ is C$_{1-10}$ unsubstituted or substituted alkyl, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or where two hydroxyl groups are joined as a ketal;

(f) a halogen;

(g) a cyclitol or substituted cyclitol as defined above; or (h) a physiologically acceptable salt of any of the above; wherein in (a) to (g) above R, R$_1$ and R$_2$ are independently hydrogen or C$_{1-10}$ unsubstituted or substituted alkyl or aryl.

According to a second embodiment of the invention, there is provided a process for preparing a compound comprising linked cyclitol residues, which process comprises the steps of:

i) reacting a substituted or unsubstituted epoxide of the formula

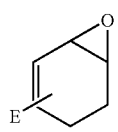

with a 1,ω-diol or a 1,ω-diamine, wherein E is an electrophilic moiety and said substituents on said epoxide comprise at least one group selected from a protected or unprotected hydroxyl or amino group;

ii) if necessary, deprotecting the linked cyclitol compound formed in step (i); and, optionally, iii) sulphating the compound formed in step (ii).

According to a third embodiment of the invention, there is provided a process for preparing a compound comprising linked cyclitol residues, which process comprises the steps of:

i) reacting a substituted or unsubstituted alkenyl compound of the formula

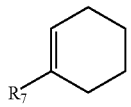

with a 1,ω-diol or a 1,ω-diamine in the presence of carbon dioxide and a transition metal catalyst, wherein R$_7$ is a halogen, triflate or boronate group, or a metal derivative, and said substituents on said alkenyl compound comprise at least two groups independently selected from a protected or unprotected hydroxyl or amino group;

ii) if necessary, deprotecting the linked cyclitol compound formed in step (i); and, optionally, iii) sulphating the compound formed in step (ii).

According to a fourth embodiment of the invention, there is provided a pharmaceutical or veterinary composition for the prevention or treatment in a mammalian subject of a disorder resulting from angiogenesis, tumour metastasis, inflammation and/or coagulation/thrombosis, which composition comprises at least one compound according to the first embodiment together with a pharmaceutically or veterinarially acceptable carrier or diluent for said at least one compound.

A fifth embodiment of the invention comprises the use of a compound according to the first embodiment in the manufacture of a medicament for the prevention or treatment in a mammalian subject of a disorder resulting from angiogenesis, tumour metastasis, inflammation and/or coagulation/thrombosis.

According to a sixth embodiment of the invention there is provided a method for the prevention or treatment in a mammalian subject of a disorder resulting from angiogenesis, tumour metastasis, inflammation and/or coagulation/thrombosis, which method comprises administer-ing to the subject an effective amount of at least one compound according to the first embodiment, or a composition comprising said at least one compound.

With regard to the compounds of the first embodiment defined above, the term "cyclitol" is used in accordance with the IUPAC definition of the term save that compounds comprising such residues can have as few as two hydroxyl groups, or derivatives of such groups, on the ring carbons. Residues can, furthermore, have one double bond within the ring.

If not otherwise specified, alkyl, aryl and other substituent groups are used in accordance with their usual meaning in the art. For example, alkyl groups would normally have from 1 to 10 carbon atoms.

Preferred compounds according to the first embodiment of the invention include the following:

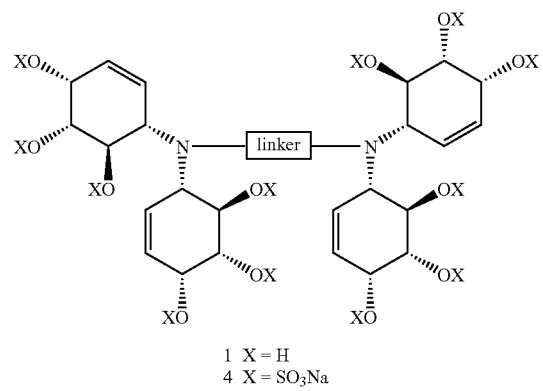

1 X = H
4 X = SO$_3$Na

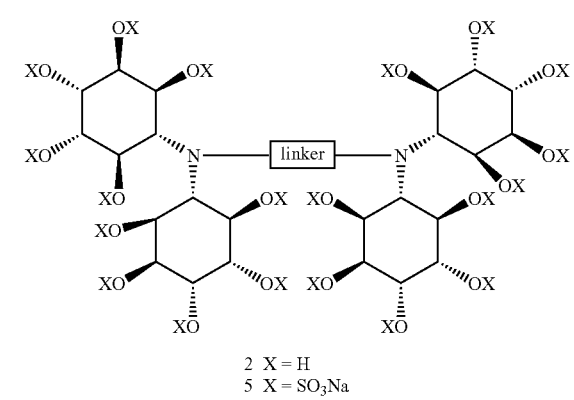

2 X = H
5 X = SO$_3$Na

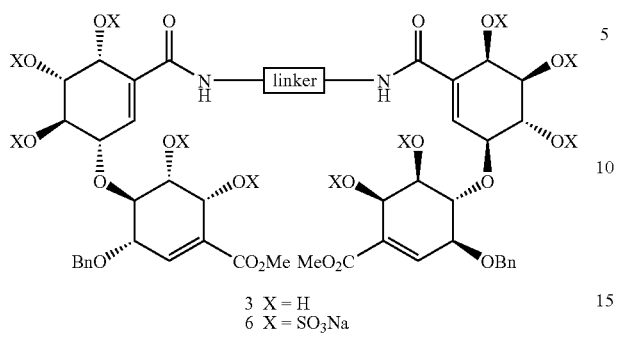

3 X = H
6 X = SO₃Na wherein the linker is any one of —(CH₂)₂—, —(CH₂)₃—, —(CH₂)₄—, —(CH₂)₅—, —(CH₂)₆—, —(CH₂)₇—, —(CH₂)₈—, —(CH₂)₉—, —(CH₂)₁₀—, m-C₆H₄—, p-C₆H₄—, m-(CH₂)C₆H₄(CH₂)— or p-(CH₂)C₆H₄(CH₂)—.

A motivating factor in selecting the types of compounds was the indication that compounds incorporating approximately five monosaccharide units might be of a "size" that leads to biologically active derivatives. In an assessment of the "size" of targets 1–6, the diamine group linking the cyclitol residues was estimated to be roughly equivalent to a single monosaccharide unit and with the overall structure, therefore, equating to that of a pentasaccharide. Since the biologically active conformations of such pentasaccharide units remain unclear, synthetic approaches were sought which would allow for significant variation in the shape (and to some extent the length) of the linkers. Capacity for variation in the manner in which the individual cyclitols were connected to one another as well as the linkers was also sought.

In the process of preparing compounds according to the invention—the second embodiment defined above—the electrophilic moiety, E, is typically a halo group (such as bromo, chloro or iodo), a carboxyl group, a derivatised carboxyl group, a cyano group, a nitro group, a sulfoxide or a sulfonate. Other suitable electrophilic groups will be known to those of skill in the art and include halo-substituted alkyl groups, acyl- or aryl-substituted amino groups, sulfhydryl groups, phenyl and substituted phenyl groups, and the like.

The epoxide of step (i) of the process according to the second embodiment is advantageously of the following structure:

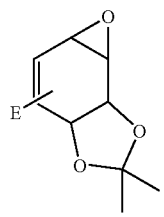

wherein E is as defined above. A particularly preferred epoxide is a compound of the following structure:

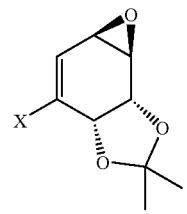

in which X is a halo group, a carboxyl group, or a derivatised carboxyl group.

The process can also include additional steps such as:
Pd[0]-mediated carbomethoxylation of the cyclitol moieties;
acetylation of the cyclitol moieties;
dehalogenation of the cyclitol moieties; and
hydroxylation of the cyclitol moieties.

These and other variations in the process will be explained in greater detail below.

Advantageously, the initial step of the process is carried out by reacting excess epoxide with the 1,ω-diol or 1,ω-diamine at elevated pressure and/or temperature. By controlling the pressure and temperature during the process, various structures are produced in which the linker can be "derivatised" such that two or more cyclitol residues are attached thereto.

The temperature and/or pressure at which step (i) of the process according to the second embodiment is performed can also be exploited to produce a particular type of linked cyclitol compound. For example, when the process is carried out with various 1,ω-diamines at room temperature to 80° C., dimers are obtained. At a temperature of 110° C., trimers are obtained while at 120° C. tetramers predominate. Conducting the step at a pressure of 5–19 kbar also results in predominantly tetramers.

The electrophilic epoxide starting material can be prepared in enantiomerically pure form using known enzymatic techniques to generate the precursor dihydrocatechol which is then elaborated using standard techniques as will be exemplified below. The process has the capacity to produce a diverse range of linked cyclitol compounds by varying the nature of the 1,ω-diols, 1,ω-diamines, and related polyamines and polyols selected, as well as by controlling the stepwise reaction/replacement of E or X.

With regard to the third embodiment defined above, the metal derivative is typically a zinc-containing reagent. Of the transition metal catalysts, palladium is preferred.

As indicated above, the invention includes within its scope compositions of the subject linked cyclitol compounds. These compositions can be formulated for pharmaceutical or veterinary use and can be administered in any of the ways known to those of skill in the art.

Pharmaceutical compositions for oral administration can be in tablet, capsule, powder or liquid form. A tablet can include a solid carrier such as gelatine or an adjuvant or an inert diluent. Liquid pharmaceutical compositions generally include a liquid carrier such as water, petroleum, animal or vegetable oils, a mineral oil or a synthetic oil. Physiological saline solution, or glycols such as ethylene glycol, propylene glycol or polyethylene glycol may be included. Such compositions and preparations will generally contain at least 0.1 wt % of the linked cyclitol compound.

Parental administration includes administration by the following routes: intravenously, cutaneously or subcutaneously, nasally, intramuscularly, intraocularly, transepithelially, intraperitoneally and tropically. Topical administration includes dermal, ocular, rectal, nasal, as well as administration by inhalation or by aerosol means. For intravenous, cutaneous or subcutaneous injection, or injection at a site where treatment is desired, the active ingredient will be in the form of a parenterally acceptable aqueous solution which is pyrogen-free and has suitable pH, isotonicity and stability. Those of skill in the art will be well able to prepare suitable solutions using, for example, solutions of the subject compounds or derivatives thereof.

In addition to the at least one linked cyclitol compound and a carrier or diluent, compositions according to the invention can further include a pharmaceutically or veterinarially acceptable excipient, buffer, stabiliser, isotonicising agent, preservative or anti-oxidant or any other material known to those of skill in the art. It will be appreciated by the person of skill that such materials should be non-toxic and should not interfere with the efficacy of the at least one linked cyclitol compound. The precise nature of any additive may depend on the route of administration of the composition: that is, whether the composition is to be administered orally or parentally. With regard to buffers, aqueous compositions typically include such substances so as to maintain the composition at a close to physiological pH or at least within a range of about pH 5.0 to 8.0.

Compositions according to the invention can also include active ingredients in addition to the at least one linked cyclitol compound. Such ingredients will be principally chosen for their efficacy as anti-angiogenic, anti-metastatic, anti-inflammatory anti-coagulant and/or anti-thrombotic agents but can be chosen for their efficacy against any associated condition.

A pharmaceutical or veterinary composition according to the invention will be administered to a subject in either a prophylactically effective or a therapeutically effective amount as necessary for the particular situation under consideration. The actual amount of at least one linked cyclitol compound administered by way of a composition, and rate and time-course of administration, will depend on the nature and severity of the condition being treated or the prophylaxis required. Prescription of treatment such as decisions on dosage and the like will be within the skill of the medical practitioner or veterinarian responsible for the care of the subject. Typically, however, compositions for administration to a human subject will include between about 0.01 and 100 mg of the linked cyclitol compound per kg of body weight and more preferably between about 0.1 and 10 mg/kg of body weight.

The linked cyclitol compounds can be included in compositions as pharmaceutically or veterinarially acceptable derivatives thereof. As used herein "derivatives" of the compounds includes salts, coordination complexes with metal irons such as $Mn^{2+}$ and $Zn^{2+}$, esters such as in vivo hydrolysable esters, free acids or bases, hydrates, or prodrugs. Compounds having acidic groups such as phosphates or sulfates can form salts with alkaline or alkaline earth metals such as Na, K, Mg and Ca, and with organic amines such as triethylamine and tris-(2-hydroxyethyl)amine. Salts can also be formed between compounds with basic groups, such as amines, with inorganic acids such as hydrochloric acid, phosphoric acid or sulfuric acid, or organic acids such as acetic acid, citric acid, benzoic acid, fumaric acid, or tartaric acid. Compounds having both acidic and base groups can form internal salts.

Esters can be formed between hydroxyl or carboxylic acid groups present in the compound and an appropriate carboxylic acid or alcohol reaction partner, using techniques that will be well known to those of skill in the art.

Prodrug derivatives of the linked cyclitol compounds of the invention can be transformed ill vivo or iii vitro into the parent compounds. Typically, at least one of the biological activities of a parent compound may be suppressed in the prodrug form of the compound, and can be activated by conversion of the prodrug to the parent compound or a metabolite thereof. Examples of prodrugs are glycolipid derivatives in which one or more lipid moieties are provided as substituents on the cyclitol moieties, leading to the release of the free form of the compound by cleavage with an enzyme having phospholipase activity. Prodrugs of linked cyclitol compounds of the invention include the use of protecting groups which may be removed in vivo to release the active compound or serve to inhibit clearance of the drug. Suitable protecting groups will be known to those of skill in the art and include an acetate group.

As also indicated above, compounds according to the invention have utility in the manufacture of a medicament for the prevention or treatment in a mammalian subject of a disorder resulting from angiogenesis, metastasis, inflammation and/or coagulation/thrombosis. Processes for the manufacture of such medicaments will be known to those of skill in the art and include the processes used to manufacture the pharmaceutical compositions described above.

Linked cyclitol compounds falling within the scope of the invention have been found to be inhibitors of endoglucuronidases (e.g., heparanase) and proteases, and to have growth factor inhibitory activity. In particular, it has been established that the compounds have heparanase inhibitory activity. The compounds thus have utility as anti-angiogenic, anti-metastatic and/or anti-inflammatory agents in the treatment of mammalian subjects including humans. The uses of the compounds include the treatment of angiogenesis-dependent diseases such as angiogenesis associated with the growth of solid tumours, proliferative retinopathies and rheumatoid arthritis, as well as the treatment of inflammatory diseases and conditions in which the heparanase-inhibitory activity of the compounds is useful in inhibiting leukocyte infiltration, including chronic inflammatory diseases where leukocyte infiltration is a key element such as rheumatoid arthritis, multiple sclerosis, inflammatory bowel diseases such as ulcerative colitis and Crohn's disease, allograft rejection and chronic asthma.

As further indicated above, the linked cyclitol compounds of the invention additionally have utility as anti-coagulant or anti-thrombotic agents. The compounds can therefore be used for both the prophylaxis and treatment of many thrombotic and cardiovascular diseases, the most notable of these being deep venous thrombosis, pulmonary embolism, thrombotic stroke, peripheral arterial thrombosis, unstable angina and myocardial infarction. Since compositions of the linked cyclitol compounds can be delivered orally, the compounds are an attractive alternative to warfarin, a widely used oral anticoagulant with severe side effects.

Having broadly described the invention, non-limiting examples of the linked cyclitol compounds, their synthesis, and their biological activities, will now be given with reference to the accompanying figures which will be briefly described in the following section of this specification.

BRIEF DESCRIPTION OF THE FIGURES

FIGS. 1 and 2 respectively show the results of inhibition of growth factor (a-FGF, b-FGF and VEGF) and chemokine (IL-8) binding to heparin while FIG. 3 shows the results of inhibition of growth factor binding to heparan sulfate.

ABBREVIATIONS AND NOMENCLATURE

Figure 1:
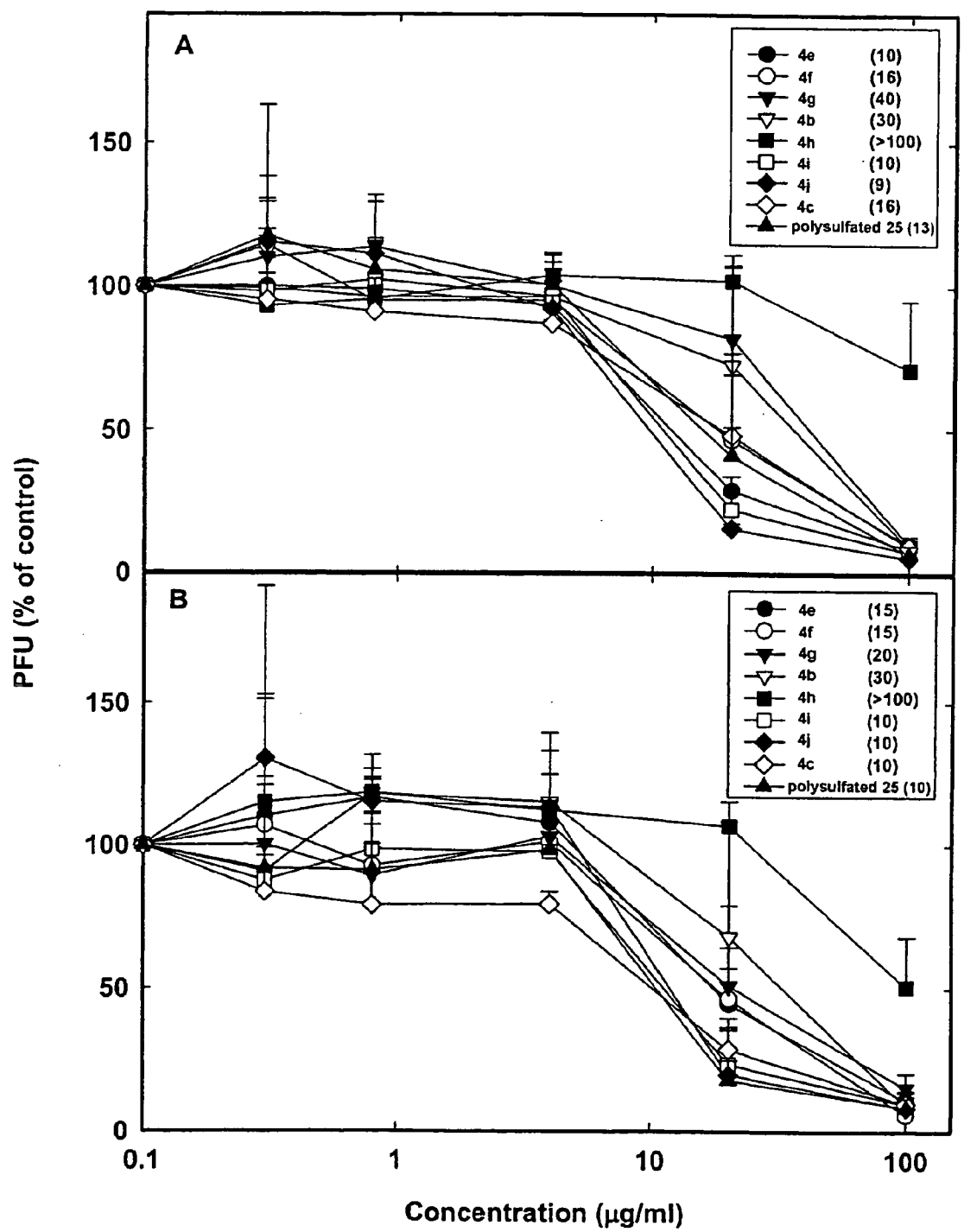
FIGS. 1 to 3 comprise graphical presentations of results of inhibition studies included in Table 4 below.

The following abbreviations are used herein:

| | |
|---|---|
| ACT | activated clotting time |
| APTT | activated partial thromboplastin time |
| Bz | benzyl |
| BM | basement membrane |
| ECM | extracellular matrix |
| FGF | fibroblast growth factor |
| Hep | heparin |
| HGF | hepatocyte growth factor |
| HS | heparan sulfate |
| IL | interleukin |
| ND | not determined |
| Ph | phenyl |
| PI-88 | phosphomannopentaose sulfate |
| VEGF | vascular endothelial growth factor |

The suffixes set out in the following table are used in the designations of the linked cyclitol compounds referred to herein.

| Suffix | Linker |
|---|---|
| (a) | —(CH$_2$)$_3$— |
| (b) | —(CH$_2$)$_6$— |
| (c) | —(CH$_2$)$_{10}$— |
| (d) | m—(CH$_2$)C$_6$H$_4$(CH$_2$)— |
| (e) | p—(CH$_2$)C$_6$H$_4$(CH$_2$)— |
| (f) | —(CH$_2$)$_2$— |
| (g) | —(CH$_2$)$_4$— |
| (h) | —(CH$_2$)$_7$— |
| (i) | —(CH$_2$)$_8$— |
| (j) | —(CH$_2$)$_9$— |
| (k) | —(CH$_2$)$_5$— |
| (l) | —CH$_2$CH(OSO$_3$Na)CH$_2$— |

BEST MODE AND OTHER MODES OF CARRYING OUT THE INVENTION

A. Chemical Syntheses

EXAMPLE 1

Synthesis of Iodoepoxide 10

Procedure A—m-CPBA in DCM

Structures of compounds referred to in this synthesis are given below in Scheme 1. To a solution of the diol 7 (25.78 g, 0.108 mol) in 2,2-dimethoxypropane (100 mL) was added p-toluenesulfonic acid monohydrate (1.03 g, 5.42 mmol, 5 mol %). The mixture was stirred in the dark at 18° C. for 1 h. Triethylamine (10 mL) was added, the solution was stirred for a few minutes and evaporated to dryness (Note: the rotovap bath temperature was maintained at 18° C. to avoid Diels-Alder dimerisation of the product). The residue was dissolved in diethyl ether (300 mL), washed with 1 M NaOH (aq. 30 mL), water (30 mL) and dried (MgSO$_4$). Filtration and evaporation gave the acetonide 8 (23.47 g, 78%) as a light-yellow gum.

The crude diene 8 (3.54 g, 12.7 mmol) obtained as described in the previous paragraph was dissolved in DCM (70 mL) and the solution was cooled in ice-water bath while m-CPBA (70% purity, 6.26 g, 25.4 mmol, 2 eq) was added in portions. After addition, the reaction mixture was stirred in the dark at 18° C. for 3 days while being monitored by TLC (n-hexane-EtOAc 6:1 v/v). The reaction mixture was filtered to remove m-chlorobenzoic acid by-product and the filtrate was washed with 15% Na$_2$SO$_3$ solution (2×30 mL), 1 M NaOH (3×30 mL), water and dried (MgSO$_4$). Filtration and evaporation gave a crude product which was subjected to column chromatography [silica, eluted with it-hexane-EtOAc (8:1 to 1:1) then EtOAc] to give four major fractions.

The fraction (R$_f$=0.39, n-hexane-EtOAc 8:1) containing the epoxide product 10 (0.859 g, 23%) was separated as colourless needles after recrystallisation from n-hexane-EtOAc (8:1). A better single-crystal (colourless needle) was obtained by sublimation at 55° C./0.12 mmHg, and this was used for X-ray analysis.

Procedure B—m-CPBA in DCM aid NaHCO$_3$

The iodo-diol 7 (16.89 g, 71.0 mmol) was protected as acetonide 8 using the method described above. The crude reaction mixture was diluted with DCM (600 mL) and washed with 1 M aq. NaOH (200 mL). The DCM phase was further diluted with DCM to 1.5 liter then sat. NaHCO$_3$ (200 mL) was added. To the resulting and vigorously stirred mixture was added m-CPBA (70% purity, 25 g) in portions. The resulting mixture was stirred in the dark at 18° C. for 8 days whilst being monitored by TLC. Another portion of m-CPBA (70% purity, 12 g, total 37 g, 150 mmol) was added and stirring continued for another 4 days. Work-up as usual and flash chromatographic purification gave epoxide 10 (8.48 g, 41%).

Structure and Properties

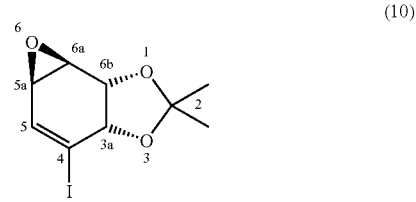

(10)

Mp 74–75.5° C. (colourless needles, sublimation at 55° C./0.12 mmHg or recrystallisation from n-hexane-ethyl acetate 8:1). Relative stereochemistry was confirmed by single X-ray diffraction analysis. [α]$_D^{18}$+142.8° (c 1.17, CHCl$_3$). HRMS-EI: C$_9$H$_{11}$IO$_3$ requires 293.9753; found 293.9753. C$_9$H$_{11}$IO$_3$ requires C, 36.76; H, 3.77; I, 43.15; found: C, 36.88; H, 3.75; I, 43.25%. IR (KBr)/cm$^{-1}$: 2987, 2931, 2878, 1617 (m), 1369, 1298, 1228 (s), 1169, 1073, (s), 1041, 1003, 975, 942, 888, 854, 825, 780, 748, 613, 573 and 532. MS-EI: 294 (49%, M+*), 279 [100, (M–CH$_3$)+], 236 (28), 221 (11), 207 (94), 191 (12), 127 (12), 110 (93), 109 (96) and 100 (52). $^1$H: 6.80 (1 H, J$_{5,5a}$ 4.4, J$_{5,3a}$ 1.5, 5-H), 4.86 (1 H, ddd, J$_{6b,3a}$ 6.6, J$_{6b,6a}$ 2.1, J$_{6b,5a}$ 1.0, 6b-H), 4.37 (1 H, dd, J$_{3a,6b}$ 6.6, J$_{3a,5}$ 1.5, 3a-H), 3.62 (1 H, dd, J$_{6a,5a}$ 3.6, J$_{6a,6b}$ 2.1, 6a-H), 3.19 (1 H, dd, J$_{5a,5}$ 4.4, J$_{5a,6a}$ 3.6, 5a-H), 1.47 (3 H, s, CH$_3$) and 1.43 (3 H, s, CH$_3$). $^{13}$C: 134.13 (CH, 5), 108.48 (C, 4), 111.10 (C, 2), 75.72 (CH, 6b), 72.00 (CH, 3a), 49.11 (CH, 6a), 48.52 (CH, 5a), 27.58 (CH$_3$) and 26.20 (CH$_3$).

EXAMPLE 2

Synthesis of Class 1 and 2 Compounds

A representative reaction sequence used to effect preparation of compounds according to the invention that included class 1 compounds is shown in Scheme 1 below and employed the cis-1,2-dihydrocatechol 7 as starting material. The following reagents and conditions were used for the indicated steps of the process: (i) 2,2-Dimethoxypropane, p-TsOH (cat.), 18° C., 1 h; (ii) m-CPBA, DCM, 18° C., 3 days; (iii) various conditions—see following text; (iv) AcCl, Et$_3$N, DCM, 0–18° C., 12 h; (v) CO, MeOH, Pd (OAc)$_2$, bis(diphenylphosphino)ferrocene, DMF, Et$_3$N, 18° C., 40 h.

Compound 7 was readily obtained in large quantity and enantiomerically pure form by the biotransformation of iodobenzene using the genetically engineered micro-organism E. coli JM109 (pDTG601) which over expresses toluene dioxygenase (TDO), the enzyme responsible for this dihydroxylation reaction. In the first step of the reaction sequence, cis-1,2-dihydrocatechol 7 was converted into the corresponding acetonide, 8, under standard conditions. The acetonide was immediately reacted with ml-chloroperbenzoic acid (m-CPBA) so as to produce, in a completely regio- and diastereo-selective manner, the epoxide 10. This compound represented a potent electrophile which reacted with a range of nucleophiles at the allylic carbon of the epoxide ring so as to give conduritol and conduramine derivatives. In particular, reaction of compound 10 with 1,6-hexadiamine in dichloromethane at 18° C. for 4 days gave the dimeric species 11 in quantitative yield. The readily obtained bis-acetamido-derivative, 12, of the latter compound was subject to a Pd[0]-mediated carbomethoxylation reaction thereby producing the diester 13 wherein each six-membered ring incorporates an exocyclic carbon in an appropriate oxidation state as required for elaboration to pseudo-sugars.

Reaction of dichloromethane solutions of various 1,ω-diaminoalkanes and related diamines with excess epoxide 10 in a sealed tube at 120° C. for seven days yielded a mixture of the corresponding di- tri- and tetra-alkylated amines, 16, 17 and 18 respectively.

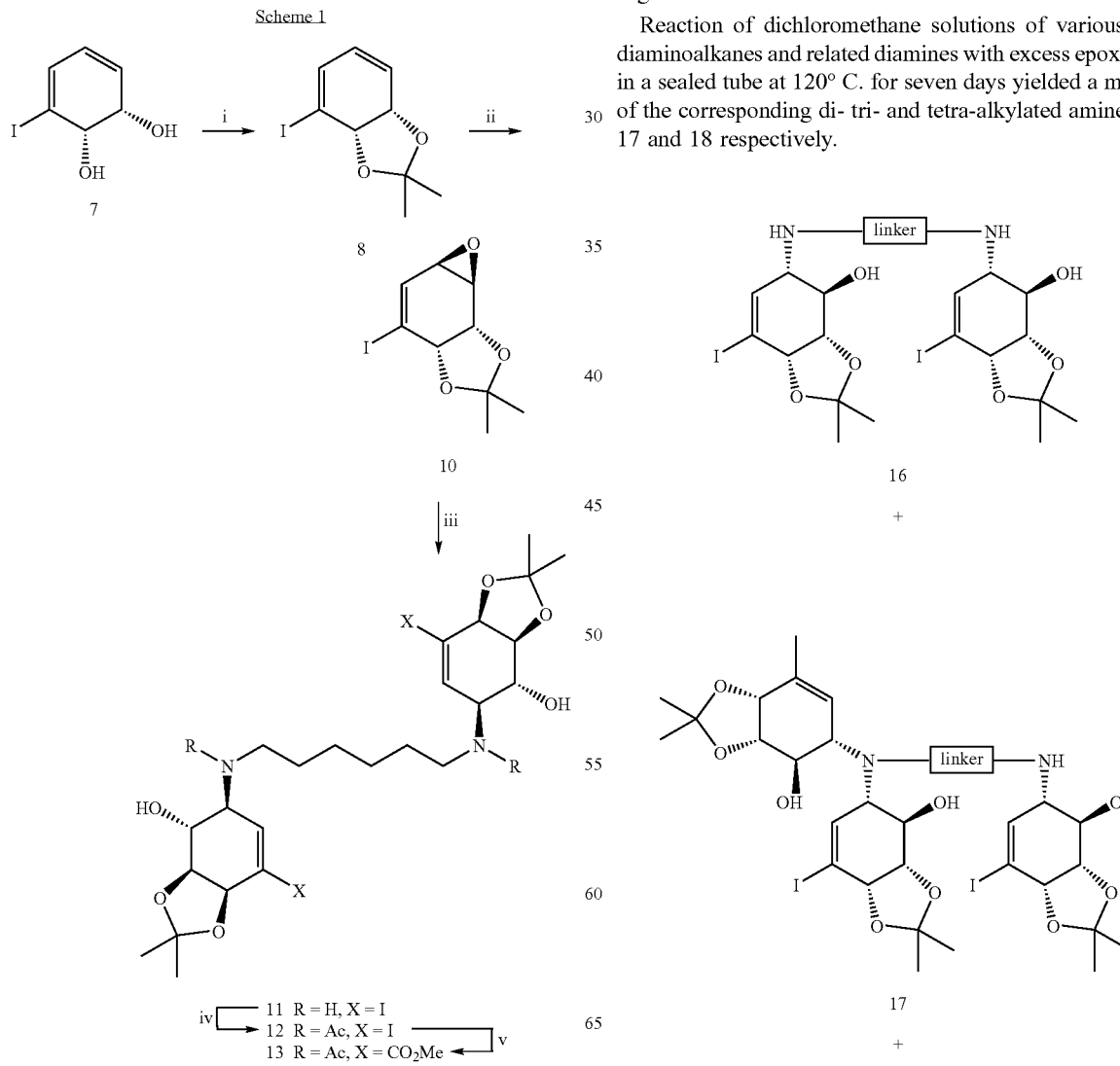
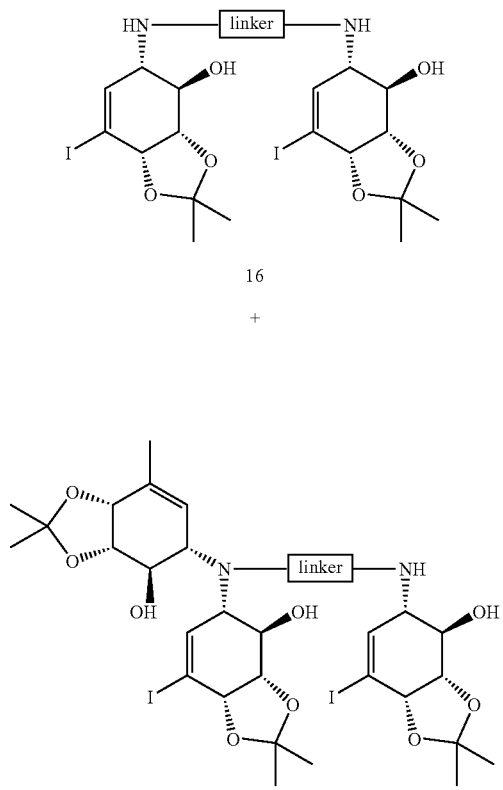

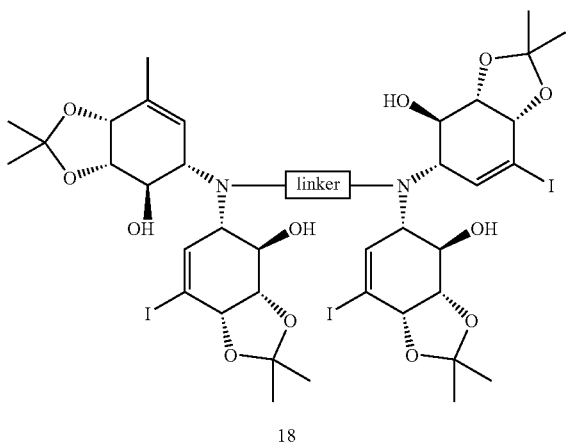

18

Generally the tetrameric product predominated. The individual components of these product mixtures were readily isolated by standard flash chromatographic methods. An examination of the product distribution as a function of temperature was undertaken and, in broad terms, when the reaction was run at or below 80° C. then only "dimer" 16 was observed, at 110° C. the "trimer" 17 predominated whilst, at 120° C. "tetramer" 18 was the major reaction product. Excellent yields of the tetrameric 18 species were often obtained when the diamine was reacted with 4.3 mole equivalents of epoxide 10 in dichloromethane at 18° C. and 19 kbar (as achieved in a PSIKA high pressure reactor) for 24 h. As a consequence this approach became the method of choice for obtaining preparative quantities of the tetramers.

The methods employed for elaboration of the tetrameric species 18 into linked pseudo-disaccharides of the general types 1 and 2 is shown below in Scheme 2. The following reagents and conditions were used for the indicated steps of the process: (i) $H_2$ (55 psi), 10% Pd on C, $Et_3N$, EtOAc, 18° C., 1 h; (ii) 1 M aq. HCl, THF, 18° C., 16 h; (iii) $OsO_4$, NMMNO, t-BuOH, acetone, water, 60° C., 7 h.

Scheme 2

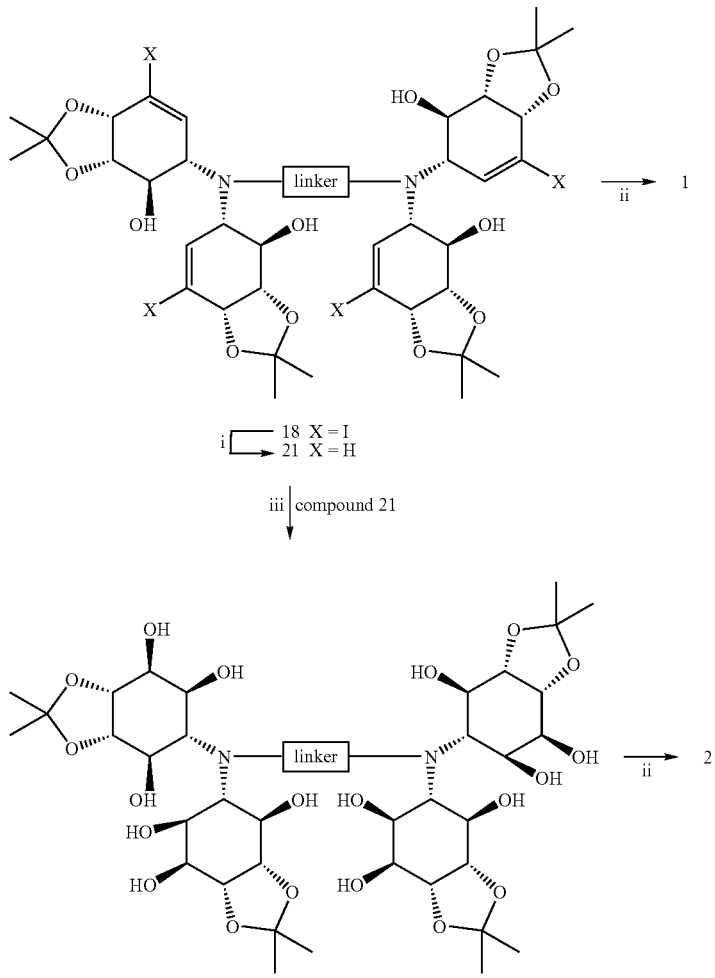

Reaction of compounds of the general type 18 with dihydrogen (55 psi) in the presence of 10% palladium on carbon and triethylamine resulted in the smooth formation of the corresponding de-iodinated products 21 without any accompanying reduction of the double bonds. The latter compounds were then readily hydrolysed, under standard conditions, to give the corresponding linked conduramines 1 or dihydroxylated under the Upjohn conditions to give the acetonide-protected cyclitols 22 which were themselves readily hydrolysed to give the second category of target compounds, namely the tetra-inositols 2. Each of the steps illustrated above occurred in a smooth fashion and the conversion 22→2 proceeded in a sluggish but completely diastereoselective manner such that dihydroxylation occurred at those faces of the double bonds unobstructed by the flanking acetonide groups.

An extension of the methods described above to a "pentameric" system is shown in Scheme 3. The following reagents and conditions were used for the indicated steps of the process: (i) various conditions—see text which follows; (ii) $H_2$ (55 psi), 10% Pd on C, $Et_3N$, EtOAc, 18° C., 24 h; (iii) 1 M aq. HCl, THF, 18° C., 16 h.

The forgoing process involved reaction of diethylenetriamine with ten equivalents of epoxide 10 in dichloromethane at 18° C. and 19 kbar for 24 hrs. Under such conditions the penta-alkylated product 23 (24%) predominated although some tetrameric material (11% as a mixture of isomers) was also observed. Reductive de-iodination of the former product was effected under the previously noted conditions and the ensuing penta-acetonide 24 (58%) then hydrolysed with aqueous acid to give the penta-conduramine 25 (85%) which was comprehensively characterized by the usual range of spectroscopic and analytical methods.

EXAMPLE 3

Synthesis of Class 3 Compounds

The diamide-linked cyclitols 3, which each incorporated four dehydropseudosugar units, were prepared by the pathway shown below in Scheme 4. The following reagents and conditions were used for the indicated steps of the process: (i) BnOH, TfOH (5 mole %), DCM, 0° C., 0.66 h; (ii) CO, MeOH, Pd(OAc)$_2$, bis(diphenylphosphino)ferrocene, DMF,

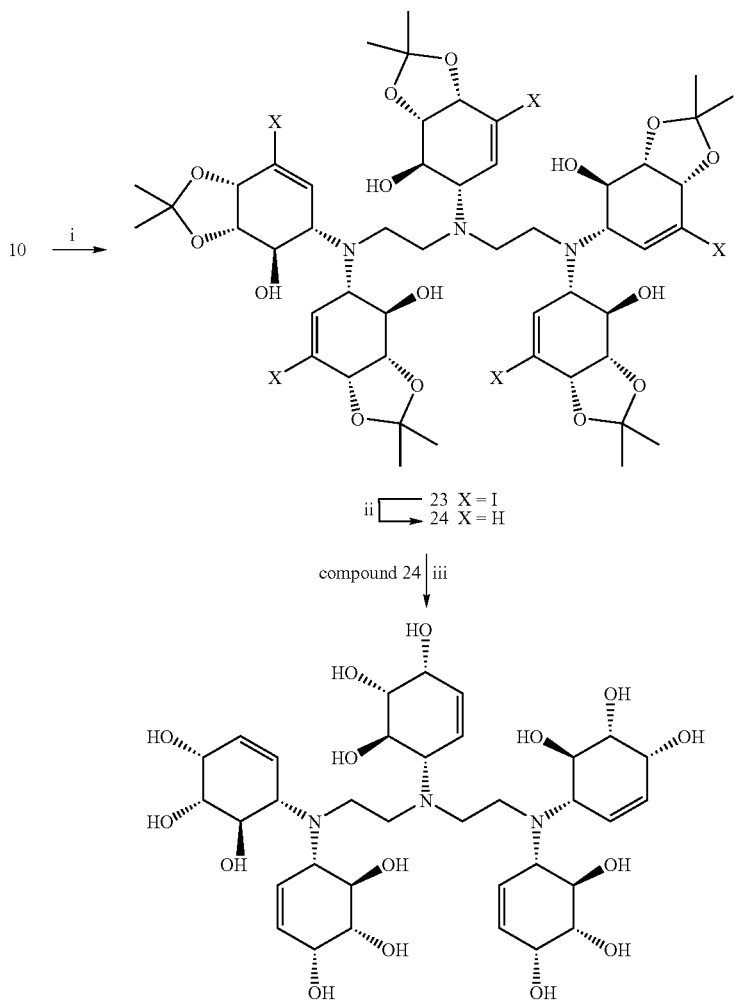

Et$_3$N, 18° C., 40 h; (iii) Compound 10, BF$_3$.Et$_2$O, DCM.−20° C., 2.5 h; (iv) 1,ω-diamine (0.5 mole equiv.), n-Bu$_3$N (1.02 mole equiv.), Pd[0] (3 mole %), DMF, CO, 100° C., 4 h; (v) 1M aq. HCl THF, 18° C., 16 h.

the presence of 5 mole % BF$_3$.Et$_2$O at −20° C. afforded the required bis-cyclitol 28 (66%) together with small quantities (12%) of the tris-cyclitol 29. The former product was subject to a Pd[0]-catalysed bis-amination reaction using the appro-

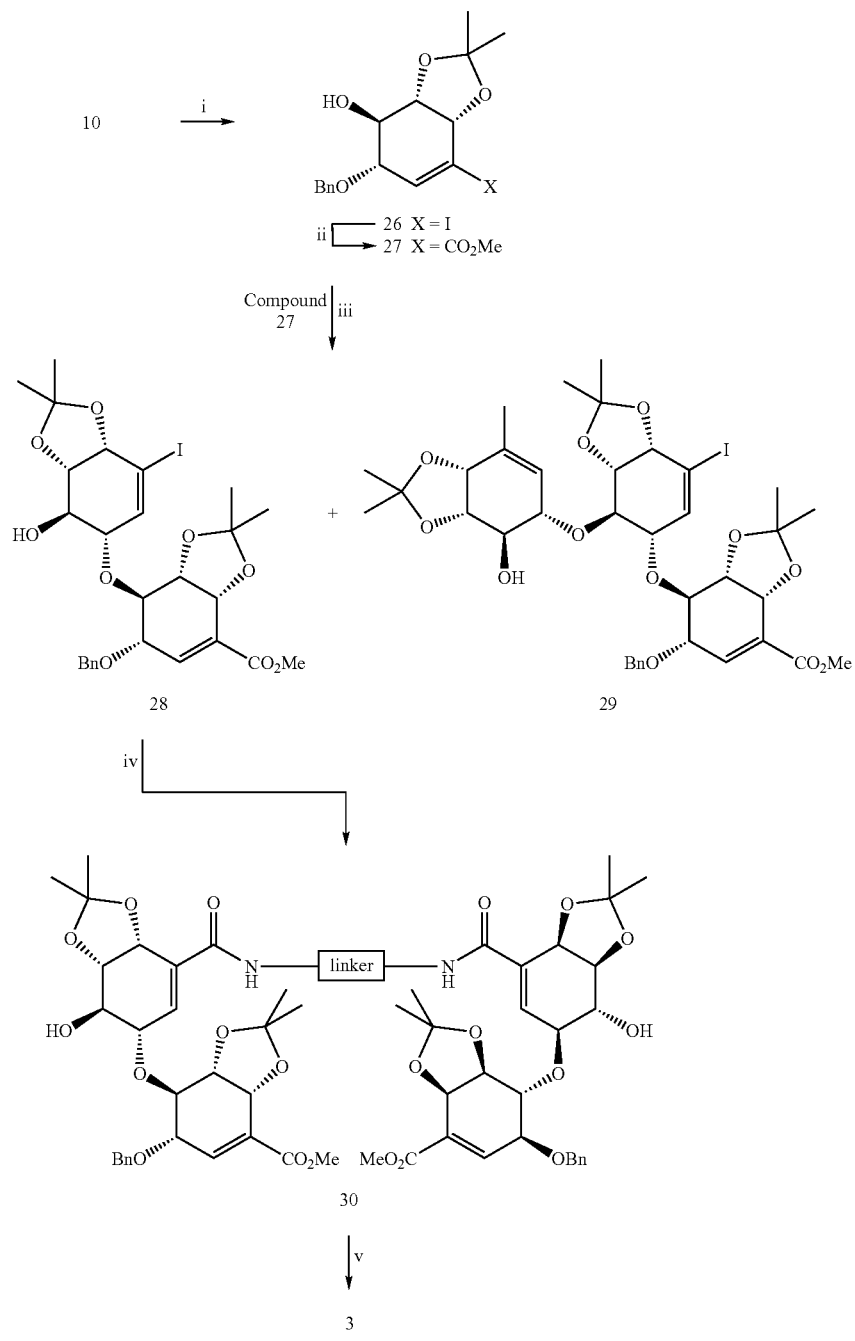

priate diamine and in this manner the bis-amides of the general type 30 were obtained in yields ranging from 5–46% depending on the catalyst and reaction conditions used. Hydrolytic cleavage of the acetonide units was achieved in the presence of aqueous mineral acid and the target scaffolds 3 thereby obtained in serviceable yield.

By way of this process, epoxide 10 was subjected to reaction with benzyl alcohol in dichloromethane at 0° C. in the presence of triflic acid and the ensuing trans-diolmonobenzyl ether 26 was carbomethoxylated under the previously described (Pd[0]-catalysed) conditions to give ester 27 (100%). Reaction of the latter compound with epoxide 10 in

EXAMPLE 4

Sulfation of Linked Cyclitols 1–3 and Evaluation of Constitution and Purity of Products of Classes 4–6

The linked cyclitols 1–3 were each reacted with sulfur trioxide/pyridine in DMF at 60° C. for 1–7 days then cooled and subjected to work-up with aqueous sodium hydroxide. The crude samples of products 4–6 thereby obtained were subject to chromatography on a Bio-Gel P-2 column so as to remove inorganic sulfate and otherwise effect some level of purification of the target compounds. These compounds were then subjected to capillary electrophoretic (CE) analyses so as to determine the homogeneity (or otherwise) of the compounds. The results of analyses are summarized in Table 1.

TABLE 1

| Compound ID | Capillary Electrophoretic Analysis |
| --- | --- |
| 4f | 5 peaks, 1 dominant (74%) |
| 4a | 4 peaks, 1 dominant (93%) |
| 4g | peaks, 2 major (65%, salt 31%) |
| 4k | pure |
| 4b | 3 peaks, 1 dominant (65,25,10%) |
| 4h | pure |
| 4i | pure |
| 4j | 4 peaks, 1 dominant (87%) |
| 4c | pure |
| 4l | broad peak |
| 4d | pure |
| 4e | pure |
| Polysulfated derivate of Compound 25 | 4 peaks, 1 dominant (71%) |
| Extra Sulfation Series Through OsO$_4$ Catalysis | |
| 5b | 7 similar peaks |
| 5c | 1 major peak |
| 5l | broad peak |
| 5d | several peaks, 1 dominant |

EXAMPLE 5

Reaction of Epoxides With Alcohol-based Nucleophiles

Acid Catalysed Reactions

A flame-dried round bottom flask was loaded with the epoxide (1 eq) and the appropriate alcohol (1–1.1 eq) in dry DCM (0.05 M), the solution was cooled to the desired temperature and treated with the appropriate acid (TfOH or BF$_3$.Et$_2$O, 5 mol %). The reaction was monitored by TLC (n-hexane-EtOAc 2:1 or 1:1). After disappearance of the epoxide, triethylamine (1 eq) and water (or sat. NaHCO$_3$ solution) were added. The DCM phase was separated and dried (MgSO$_4$). Purification by column chromatography or PTLC (n-hexane-EtOAc 2:1) provided the products.

Reaction of Iodo-epoxide 10 with Benzyl Alcohol

The following conditions were used: TfOH (5 mol %), 0° C., 40 min. Products were isolated by column chromatography (silica, n-hexane-EtOAc 4:1 to 2:1) as follows:

trans-alcohol 26, R$_f$=0.34 (n-hexane-EtOAc 2:1), yield 50%;

cis-alcohol 31, R$_f$=0.49 (n-hexane-EtOAc 2:1), yield 17%; and iodo-"dimer" 32, R$_f$=0.42 (n-hexane-EtOAc 2:1), yield 6%.

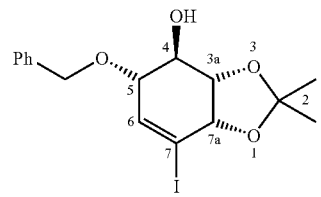

Properties: mp 113–116° C. (colourless fine needles, n-hexane-ethyl acetate 8:1). HRMS-EI: C$_{16}$H$_{19}$IO$_4$ requires 402.0328; found 402.0333. C$_{16}$H$_{19}$IO$_4$.0.25H$_2$O requires C, 47.25, H, 4.83, I, 31.20; Found: C, 47.28, H, 4.91, I, 31.92. $[\alpha]_D^{18}$+225.6° (c 0.546, CHCl$_3$). IR (KBr)/cm$^{-1}$: 3483 (s), 3063, 3030, 2978, 2870, 1629, 1496, 1453, 1386, 1372, 1306, 1255, 1210, 1163, 1136, 1069 (s), 1009, 909, 870, 795, 736, 695, 614, 533 and 507. MS-EI: 402 (1%, M$^{+*}$), 387 (10, [M–CH$_3$]$^+$), 343 (0.6), 344 (0.6), 315 (10), 302 (25), 238 (33), 220 (14), 217 (7), 101 (49) and 91 (100). $^1$H: 7.40–7.31 (5H, m), 6.55 (1H, s, 6-H), 4.73 (1H, d, $^2$J 11.5, 1×OCH$_2$Ph), 4.68 (1H, d, J$_{7a,3a}$ 6.7, 7a-H), 4.63 (1H, d, $^2$J 11.5, 1×OCH$_2$Ph), 4.13 (1H, dd, J$_{3a,4}$ 8.8, J$_{3a,7a}$ 6.7, 3a-H), 3.86 (1H, d, J$_{5,4}$ 8.4, 5-H), 3.71 (1H, t, J$_{4,5}$ 8.8, J$_{4,3a}$ 8.4, 4-H), 2.70 (1H, br s, OH), 1.54 (3H, s, CH$_3$) and 1.41 (3H, s, CH$_3$). $^{13}$C: 140.93 (CH), 137.32 (C), 128.60 (CH), 128.10 (CH), 127.92 (CH), 110.30 (C), 93.04 (C), 79.46 (CH), 79.36 (CH), 77.11 (CH), 72.74 (CH), 72.22 (CH$_2$), 28.07 (CH$_3$) and 25.80 (CH$_3$).

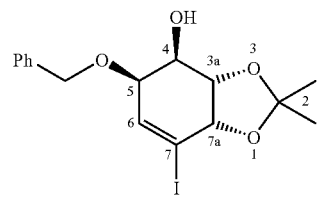

Properties: mp 78–79° C. (colourless crystals, n-hexane-EtOAc 8:1). HRMS-EI: C$_{16}$H$_{19}$IO$_4$ requires 402.0328; found 402.0331. $[\alpha]_D^{18}$–38.6° (c 0.627, CHCl$_3$). IR (KBr)/cm$^{-1}$: 3432, 2989, 2871, 1626, 1449, 1373, 1241, 1224, 1073 (s), 1052, 751. MS-EI: 402 (0.7%, M$^{+*}$), 387 (4.8, [M–CH$_3$]$^+$), 344 (3.5), 315 (3.3), 302 (45), 217 (8.0). $^1$H: 7.42–7.30 (5H, m), 6.43 (1H, d, J 2.4), 4.68 (1H, d, $^2$J 11.6), 4.63 (1H, d, $^2$J 11.6), 4.69–4.63 (1H, m, overlapping with the doublets centered at δ 4.68 and 4.63), 4.44–4.36 (2H, m), 4.11 (1H, br m), 2.55 (1H, br s), 1.41 (3H, s) and 1.39 (3H, s). $^{13}$C: 137.22, 136.46, 128.65, 128.21, 127.80, 109.80, 101.27, 78.20, 75.77, 74.74, 71.60, 67.23, 27.56 and 26.24.

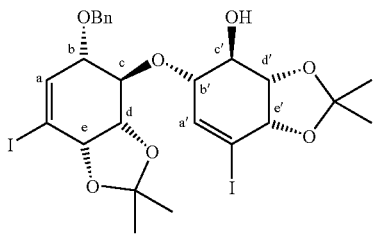

32

Properties: mp 216–218° C. (colourless needles, n-hexane-EtOAc 1:1). HRMS-EI: M–CH$_3$ (C$_{24}$H$_{27}$I$_2$O$_7$ requires 680.9846; found 680.9834. C$_{25}$H$_{30}$I$_2$O$_7$ requires C, 43.12, H, 4.34, I, 36.45; found C, 42.84, H, 4.22, I, 36.52. $[\alpha]_D^{18}$+ 70.6° (c 0.895, CHCl$_3$). IR (KBr)/cm$^{-1}$: 3467, 2984, 2882, 1630, 1453, 1378, 1258, 1213, 1164, 1110, 1086, 1069 (s), 1037, 997, 907, 872 (m), 790, 750 and 698. MS-EI: 681 (2.1%, [M–CH$_3$]$^+$), 596 (3.4), 532 (3.6), 512 (2,3), 454 (1.1), 395 (24), 302 (8), 278 (13), 237 (27) and 220 (34). $^1$H: 7.45–7.30 (5H, m), 6.58 (1H, s, Ha), 6.50 (1H, s, Ha'), 4.73 (1H, d, J 6.7, He), 4.71(1H, d, $^2$J 10.9, OCH$_2$Ph), 4.62 (1H, d, J 6.9, He'), 4.53 (1H, d,$^2$J 10.9, OCH$_2$Ph), 4.45 (1H, br s), 4.22 (1H, dd, J 9.0, J 6.9, Hd'), 4.10 (1H, dd, J 9.1, J 6.8, Hd'), 3.92 (1H, d, J 8.7, Hb), 3.86 (1H, d, J 8.5, Hb'), 3.62 (1H, dd, J 9.1, J 8.5, Hc'), 3.53 (1H, dd, J 9.0, J 8.7, Hc), 1.56 (3H, s), 1.54 (3H, s), 1.40 (3H, s) and 1.38 (3H, s); Note: Ha-Hb-Hc-Hd-He and Ha'-Hb'-Hc'-Hd'-He' are used to distinguish two sets of protons in two cyclohexene rings, but which set belong to which ring has not been confirmed (connection deduced by COSY). $^{13}$C: 142.85 (CH), 140.48 (CH), 136.51 (C), 128.84 (CH), 128.43 (CH),128.37 (CH), 110.67 (C), 110.16 (C), 92.27 (C), 92.11 (C), 84.95 (CH), 83.74 (CH), 79.78 (CH), 79.70 (CH), 79.69 (CH), 79.32 (CH), 76.68 (CH), 73.86 (CH), 72.29 (CH$_2$), 28.04 (CH$_3$), 27.55 (CH$_3$), 25.65 (CH$_3$) and 25.44 (CH$_3$).

Reaction of Iodo-epoxide 10 with Iodo-alcohol 26

The following conditions were employed: BF$_3$.Et$_2$O (5 mol %), –23° C., 2h. The crude reaction product (white solid) was recrystallised from EtOAc to give pure "dimer" 32 as colourless crystals (45%).

Reaction of Ester-epoxide with Benzyl Alcohol

The following conditions were used: TfOH (10 mol %), 18° C., 3 h. Products were isolated by column chromatography (silica, n-hexane-EtOAc 2:1 to 1:2) as follows:

trans-alcohol 27, R$_f$=0.38 (n-hexane-EtOAc 1:1), yield 42%;

cis-alcohol 33, R$_f$=0.45 (n-hexane-EtOAc 1:1), yield 2%; and ester "dimer" 34, R$_f$=0.28 (n-hexane-EtOAc 1:1), yield 17%.

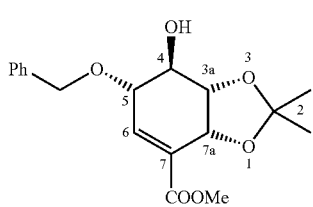

27

Properties: colourless oil. HRMS-EI: C$_{18}$H$_{22}$O$_6$ requires 334.1416; found 334.1413. $[\alpha]_D^{18}$+36.2° (c 0.646, CHCl$_3$). IR (CHCl$_3$ film)/cm$^{-1}$: 3464 (br s), 3028, 2988, 2934, 1723 (s), 1656, 1497, 1437, 1371, 1249 (s), 1218 (s), 1165, 1092 (s), 1069 (s), 1000, 919, 877, 863, 753, 699 and 513. MS-EI: 334 (19%, M$^{+*}$), 319 (17, [M–CH$_3$]$^+$), 227 (7), 170 (28), 152 (12), 138 (13), 125 (8), 101 (21) and 91 (100). $^1$H: 7.39–7.33 (5H, m), 7.05 (1H, d, J 1.6), 4.93 (1H, d, J 5.5), 4.81 (1H, d, J 11.5), 4.71 (1H, d, J 11.5), 4.11 (1H, dd, J 9.2, 6.0), 4.00 (1H, dt, J 8.9, 1.5), 3.81 (3H, s), 3.83–2.98 (1H, m, overlapping with CH$_3$O at δ 3.81), 2.79 (1H, d, J 2.0), 1.52 (3H, s) and 1.45 (3H, s). $^{13}$C: 165.33, 141.79, 137.39, 128.61, 128.11, 127.97, 127.58, 111.06, 17.59, 77.50, 72.78, 72.43, 71.02, 52.33, 28.38 and 26.24.

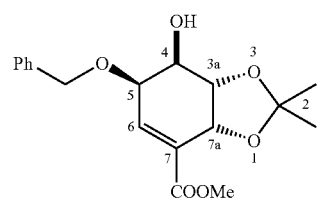

33

Properties: light-yellow wax. HRMS-EI: M–CH$_3$ (C$_{17}$H$_{19}$O$_6$) requires 319.1182; found 319.1184. $[\alpha]_D^{18}$–40.5° (c 1.34, CHCl$_3$). R (CHCl$_3$)/cm$^{-1}$: 3461, 2986, 2930, 1721 (s), 1437, 1371, 1252 (s), 1060 (s), 1027, 911, 864, 743 and 699. MS-EI: 319 (9%, [M–CH$_3$]$^+$), 276 (7), 247 (12), 234 (20), 185 (9), 170 (13), 152 (8) and 139 (13). $^1$H: 7.38–7.30 (5H, m), 6.91 (1H, dd, J$_{6,5}$ 1.9, J$_{6,4}$ 1.8, H6), 5.05 (1H, d, J$_{7a,3a}$ 5.7, H7a), 4.74 (1H, d, $^2$J 11.7, OCH$_2$Ph), 4.68 (1H, d, $^2$J 11.6, OCH$_2$Ph), 4.51 (1H, dd, J$_{3a,7a}$ 5.7, J$_{3a,4}$ 4.2, H3a), 439 (1H, m, H4), 4.28 (1H, m, H5), 3.81 (3H, s, OCH$_3$), 2.52 (1H, br s, OH), 1.39 (3H, s, 2-CH$_3$) and 1.32 (3H, s, 2-CH$_3$). $^{13}$C: 166.01 (C), 137.93 (CH), 137.25 (C), 130.39 (C), 128.65 (CH), 128.20 (CH), 127.84 (CH), 109.23 (C), 74.68 (CH), 73.19 (CH), 71.75 (CH$_2$), 70.09 (CH), 68.57 (CH), 52.21 (CH$_3$), 27.41 (CH$_3$) and 25.59 (CH$_3$).

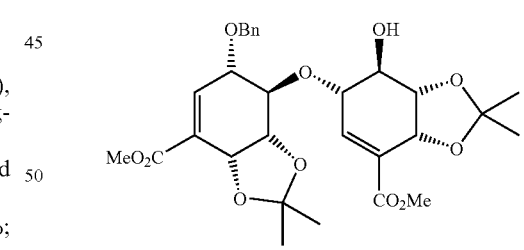

34

Properties: mp 149.5–150.5° C. (colourless needles, n-hexane-EtOAc 3:1). HRMS-EI: C$_{29}$H$_{36}$O$_{11}$ requires 560.2258; found 560.2262. C$_{29}$H$_{36}$O$_{11}$ requires C, 62.13, H, 6.47; found C, 62.16, H, 6.30. $[\alpha]_D^{18}$+71.3° (c 0.70, CHCl$_3$). IR (KBr)/cm$^{-1}$: 3506, 2994, 2951, 2882, 1719 (s), 1658, 1455, 1438, 1375, 1362, 1322, 1281, 1258 (s), 1215, 1168, 1147, 1098, 1072, 1061, 1024, 1009, 991, 917, 874 (m), 813, 756 (m) and 700. MS-EI: 560 (2%, M$^{+*}$), 545 (2.8, [M–CH$_3$]$^+$), 487 (0.7), 460 (3.3), 437 (1.0), 415 (0.8), 396 (7.2), 237 (12), 169 (35) and 137 (28). $^1$H: 7.40–7.29 (5H, m), 7.09 (1H, d, J 1.6), 7.05 (1H, d, J 1.7), 5.01 (1H, d, 6.0), 4.89 (1H, d, J 6.0), 4.82 (1H, d, $^2$J 11.1, OCH$_2$Ph), 4.67 (1H, d, $^2$J 11.1, OCH$_2$Ph), 4.54 (1H, s), 4.26 (1H, dd, J9.2, 6.4), 4.14–4.08 (2H, m), 4.02 (1H, d, J 8.8), 3.82 (3H, s), 3.74 (3H, s), 3.82–3.62 (2H, m, overlapping with two methoxy singlets at δ 3.82 and δ 3.74), 1.56 (3H, s), 1.54 (3H, s), 1.45 (3H, s) and 1.43 (3H, s). $^{13}$C: 165.30 (C), 165.08(C, 143.69 (CH), 140.68 (CH) 136.72 (C), 128.54 (CH), 128.21 (CH, 2×CH overlapping), 127.34 (C), 126.93 (C), 111.44 (C), 110.86 (C), 84.29 (CH), 83.53 (CH), 77.86 (CH), 77.08 (CH), 73.51 (CH), 72.22(CH$_2$), 71.33 (CH, 2×CH overlapping), 70.88 (CH), 52.40 (CH$_3$), 52.11 (CH$_3$), 28.35 (CH$_3$), 27.77 (CH$_3$), 26.13 (CH$_3$) and 25.77 (CH$_3$).

Reaction of Iodo-epoxide 10 with Ester Alcohol 27

The following conditions were used: BF$_3$.Et$_2$O (5 mol %), −20° C., 2.5 h. The crude product mixture (white solid) was recrystallised from EtOAc to afford the first crop of the "dimer" 28 (44%). The filtrate was separated by column chromatography (silica, CHCl$_3$-EtOAc 8:1 to 4:1) to give the following two fractions:

F1: R$_f$=0.68 (CHCl$_3$-EtOAc 8:1), "trimer" 29 (colourless gum, 12%); and

F2: R$_f$=0.38 (CHCl$_3$-EtOAc 8:1), "dimer" 28 (white solid, 22%)

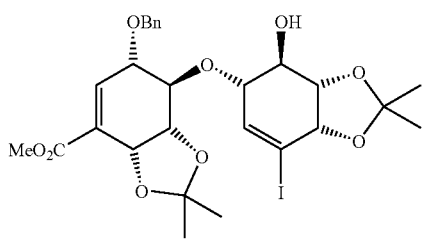

28

Properties: mp 190–192° C. (white solid). HRMS-EI: C$_{27}$H$_{33}$IO$_9$ requires 628.1169; found 628.1163. M−CH$_3$ (C$_{26}$H$_{30}$IO$_9$) requires 613.0935; found 613.0934. [α]$_D^{18}$+ 76.6° (c 0.522, CHCl$_3$). IR (KBr)/cm$^{−1}$: 3507, 2980, 2878, 1719 (s), 1655, 1453, 1376, 1362, 1259 (s), 1212, 1111, 1067, 1023, 874 and 753. MS-EI: 628 (6%, M$^{+*}$), 613 (7, [M−CH$_3$]$^+$), 528 (8), 464 (10), 395 (11), 295 (8), 237 (17), 169 (19) and 152 (26). $^1$H: 7.43–7.30 (5H, m), 7.10 (1H, d, J 1.6), 6.54 (1H, s), 5.00 (1H, d, J 6.1), 4.80 (1H, d, $^2$J 10.9, OCH$_2$Ph), 4.63 (1H, d, J 7.1), 4.59 (1H, d, $^2$J 10.9, OCH$_2$Ph), 4.55 (1H, s), 4.23 (1H, dd, J 9.2, 6.3), 4.11 (1H, dd, J 9.1, 6.8), 4.06 (1H, d, J 8.9), 3.87–3.82 (1H, m or d, overlapping with δ 3.83 singlet), 3.83 (3H, s), 3.64 (1H, dd, J 8.9, 8.7), 3.59 (1H, dd, J 9.1, 9.0), 1.549 (3H, s), 1.543 (3H, s), 1.44 (3H, s) and 1.39 (3H, s). $^{13}$C: 165.07 (C), 142.85 (CH), 140.65 (CH), 136.46 (C), 128.83 (CH), 128.48 (CH), 128.36 (CH), 127.28 (C), 111.40 (C), 110.13 (C), 92.09 (C), 85.12 (CH), 83.93 (CH), 79.29 (CH), 77.76 (CH), 77.06 (CH), 76.68 (CH), 73.76 (CH), 72.26 (CH$_2$), 71.29 (CH), 52.40 (CH$_3$), 28.01 (CH$_3$), 27.75 (CH$_3$), 25.75 (CH$_3$) and 25.64 (CH$_3$).

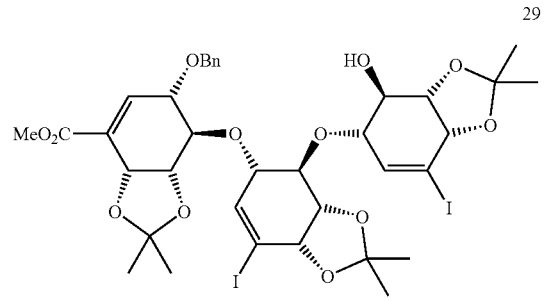

29

Properties: colourless gum. HRMS-EI: M−CH$_3$ (C$_{35}$H$_{41}$I$_2$O$_{12}$) requires 907.0688; found 907.0681. [α]$_D^{18}$+ 22.7° (c 1.90, CHCl$_3$). IR (CHCl$_3$)/cm$^{−1}$: 3452, 2988, 2930, 1724 (s), 1632, 1454, 1437, 1381, 1254, 1216, 1163, 1072, 998, 917, 867 and 753. MS-EI: 907 (11%, [M−CH$_3$]$^+$), 737 (8), 528 (21), 395 (28), 295 (18), 237 (34), 220 (24), 169 (24) and 152 (37). $^1$H: 7.40–7.31 (5H, m), 7.04 (1H, s), 7.02 (1H, s), 6.82 (1H, s), 4.99 (1H, d, J 6.2), 4.78–4.65 (3H, m), 4.50 (1H, s), 4.28–4.11 (5H, m), 3.93–3.89 (2H, m), 3.82 (3H, s), 3.66 (1H, dd or t, 8.9, 8.8), 3.58 (1H, dd or t, 8.8, 8.8), 3.51 (1H, dd or t, 8.8, 8.8), 1.62 (3H, s), 1.56 (3H, s), 1.52 (6H, s), 1.42 (3H, s) and 1.41 (3H, s). $^{13}$C: 165.08 (C), 143.62 (CH), 142.03 (CH), 141.29 (CH), 137.02 (C), 128.63 (CH), 128.36 (CH), 128.09 (CH), 127.14 (C), 111.07 (C), 110.43 (C), 110.13 (C), 91.91 (C), 91.64 (C), 84.15 (CH), 83.50 (CH), 81.75 (CH), 79.60 (CH), 79.33 (CH), 79.24 (CH), 77.79 (CH), 76.55 (CH), 75.76 (CH), 74.33 (CH), 73.37 (CH$_2$), 71.30 (CH), 52.36 (CH$_3$), 28.32 (CH$_3$), 27.99 (CH$_3$), 27.44 (CH$_3$), 26.27 (CH$_3$), 25.6 (CH$_3$) and 25.23 (CH$_3$).

EXAMPLE 6

Pd[0]-catalysed Carbomethoxy Group Insertion

A round bottomed-flask was loaded with palladium acetate (15 mol %) and 1,1'-bis(diphenylphosphino)ferrocene (40 mol %) and DMF (0.2 M) then the mixture was purged with CO for 5 min. Triethylamine (2 eq), methanol (20 eq) and appropriate alkenyl iodide (1 eq, at 1 mmol scale) were added in that order. The mixture was purged again with CO for 15 min, then stirred under a CO atmosphere (balloon) at 18° C. for 6–40 h while being monitored by TLC (1:1 v/v n-hexane-EtOAc elution). The reaction mixture was diluted with DCM and washed with 1.67% (w/w) aqueous solution of sodium diethyldithiocarbamate then dried (MgSO$_4$) and purified by column chromatography or PTLC.

Formation of Ester Alcohol Monomer 27

The following conditions were used: 18° C., 6 h. The product 13 was isolated by column chromatography (silica, Et$_2$O); R$_f$=0.66, yield 100%.

Formation of Ester Mono Diene 36

The following conditions were used: 20 mmol of iododiene 8, Pd(OAc)$_2$ (2 mol %/) and DPPF (4 mol %), 18° C., 5 days. Column chromatography (silica, n-hexane-EtOAc 6:1) afforded the illustrated diene-ester (36) as a pale-yellow gum which was used immediately in the epoxidation reaction (see the following example).

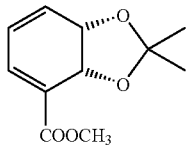
36

Properties: ¹H: 7.15 (1H, dd, J 5.0, J 1.7), 6.15–6.07 (2H, m), 4.93 (1H, d, J 8.4), 4.87 (1H, dd, J 8.7, J 1.7), 3.82 (3H, s), 1.46 (3H, s) and 1.40 (3H, s).

EXAMPLE 7

Formation of Ester Epoxide A

Following the procedure for epoxidation described above, the crude diene ester 36 (which was contaminated with some iodo-diene precursor) was treated with m-CPBA to give a mixture of epoxides A and 37 as well as Diels-Alder adducts 38, 39, which were separated by column chromatography (silica, 4:1 to 1:1 v/v n-hexane-EtOAc elution) to yield the fractions summarised in the following paragraphs.

F1: aromatised by-product 40 (0.3%, colourless gum), $R_f$=0.62 (n-hexane-EtOAc 2:1).

F2: ester epoxide 37 (2–16%, colourless crystals), $R_f$=0.52 (n-hexane-EtOAc 2:1). A single crystal was obtained by recrystallisation from EtOAc and this was subject to X-ray analysis).

F3: ester epoxide A (13–31%, pale-yellow syrup), $R_f$=0.46 (it-hexane-EtOAc 2:1).

F4: mono-ester Diels-Alder adduct 38 (1–6%, white solid), $R_f$=0.38 (n-hexane-EtOAc 2:1).

F4: diester Diels-Alder adduct 39 (1–11%, white solid), $R_f$=0.33 (n-hexane-EtOAc 2:1).

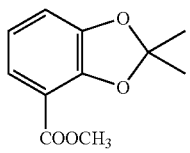
40

Properties: ¹H: 7.35 (1H, dd, J 7.9, J 1.5), 6.87 (1H, dd, J 7.6, J 1.5), 6.79 (1H, dd, J 7.9, J 7.6), 3.89 (3H, s) and 1.73 (6H, s). ¹³C: 164.97 (C), 148.33 (C), 148.30 (C), 121.91 (CH), 120.30 (CH), 119.04 (C), 112.38 (CH), 111.82 (CH), 51.70 (CH₃) and 25.78 (CH₃).

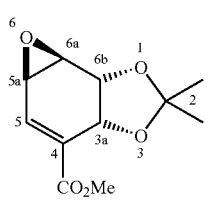
A

Properties: HRMS-EI: $C_{11}H_{14}O_5$ requires 211.0607; found 211.0607. $[\alpha]_D^{18}$+101.8° (c 1.36, CHCl₃). IR (neat)/cm⁻¹: 2989, 2953, 1725 (s), 1657, 1437, 1381, 1258, 1067, 1018, 964, 865, 808, 835 and 766. MS-EI: 227 (4%, [M+H]⁺), 211 (100, [M−CH₃]⁺), 195 (26), 179 (7), 169 (44), 153 (11), 139 (56), 137 (52) and 109 (51). ¹H: 7.11 (1H, d, $J_{5,5a}$ 3.8, H5), 4.79 (2H), m, H3a and H6b), 3.81 (3H, s, CH₃O), 3.57 (1H, d, $J_{6a,5a}$ 3.3, H6a), 3.46 (1H, dd, $J_{5a,5}$ 3.8, $J_{5a,6a}$ 3.3, H5a), 1.43 (3H, s) and 1.40 (3H, s). ¹³C: 165.61 (C), 134.30 (CH), 133.20 (C), 110.74 (C), 70.92 (CH), 68.64 (CH), 52.26 (CH or CH₃), 50.72 (CH or CH₃), 46.18 (CH or CH₃), 27.53 (CH₃) and 25.51 (CH₃).

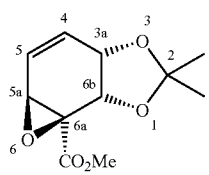
37

Properties: mp 56–60° C. (colourless crystals, n-hexane-Et₂O 1:1). Relative stereochemistry was confirmed by single X-ray diffraction analysis. The single crystal was obtained by sublimation of the bulk sample at 30–37° C. whilst stored in a vacuum desiccator for about 3 months. HRMS-EI: $C_{11}H_{14}O_5$ requires 211.0606; Found 211.0603. $[\alpha]_D^{18}$ −65.4° (c 1.16, CHCl₃). R (KBr)/cm⁻¹: 3075, 2994, 2901, 1743 (s), 1441, 1373, 1312, 1282, 1237, 1191, 1140, 1090, 1068, 1049, 1035, 990, 962, 941, 900, 857, 803, 785, 765, 621 and 524. MS-EI: 211 (100%, [M−CH₃]⁺), 195 (7), 179 (20), 169 (68), 143 (15), 139 (27), 137 (44), 125 (12), 109 (87), 110 (29) and 107 (31). ¹H: 6.00 (1H, ddd, $J_{5,4}$ 10.0, $J_{5,5a}$ 3.9, ⁴$J_{5,3a}$ 1.8, H5), 5.82 (1H, dm or br d, $J_{4,5}$ 10.0, $J_{4,3a}$ 2.0, ⁴$J_{4,5a}$ 1.1, H4), 4.98 (1H, d, $J_{6b,3a}$ 6.1, H6b), 4.58 (1H, ddd, $J_{3a,6b}$ 6.1, $J_{3a,4}$ 2.0, ⁴$J_{3a,5}$ 1.8, H3a), 3.86 (1H, dd, $J_{5a,5}$ 3.9, ⁴$J_{5a,4}$ 1.1, H5a), 3.83 (3H, s), 1.44 (3H, s) and 1.38 (3H, s). ¹³C: 170.00 (C), 134.32 (CH), 121.22 (CH), 110.83 (C), 72.50 (CH), 70.51 (CH), 54.61 (C), 52.67 (CH or CH₃), 51.63 (CH or CH₃), 27.64 (CH₃) and 26.29 (CH₃).

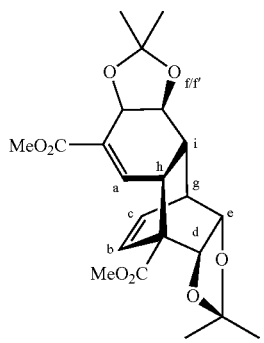
38

Properties: mp 132–133° C. (white solid, n-hexane-Et₂O). HRMS-EI: M−CH₃ ($C_{21}H_{25}O_8$) requires 405.1549; found 405.1553. $[\alpha]_D^{18}$+71.7° (c 0.565, CHCl₃). IR (KBr)/cm⁻¹: 3064, 2985, 2958, 2940, 2907, 2875, 1741 (s), 1722 (s), 1659, 1462, 1435, 1380, 1372, 1262 (s), 1245, 1220, 1187, 1167, 1108, 1088, 1061 (s), 1025, 972, 881, 742, 637 and 529. MS-EI: 421 (1.2%, M+1), 405 (82, [M−CH₃]⁺), 389 (34), 363 (39), 362 (100), 347 (90), 331 (49), 304 (40), 287

(32), 286 (22), 273 (72), 245 (66), 227 (64), 213 (68), 199 (40), 185 (46), 177 (50), 153 (85), 128 (66) and 121 (82). $^1$H: 6.38 (1H, d, J 3.8), 6.37 (1H, d, J 8.2), 6.04 (1H, dd, J 8.2, J 6.6), 4.59 (1H, d, J7.2), 4.56 (1H, d, J 4.8), 4.42 (1H, dd, J 7.1, J 3.4), 4.19 (1H, dd, J 4.8, J 2.1), 3.89 (3H, s), 3.76 (3H, s), 3.02–2.94 (2H, m), 2.35 (1H, d, J 9.2), 1.36 (3H, s), 1.29 (6H, s) and 1.27 (3H, s). $^{13}$C: 171.89 (C), 166.39 (C), 136.47 (CH), 131.42 (C), 130.05 (CH), 128.65 (CH), 109.72 (C), 108.15 (C), 80.60 (CH), 78.29 (CH), 76.84 (CH), 69.13 (CH), 53.94 (C), 52.64 (CH$_3$), 51.91 (CH$_3$), 40.29 (CH), 38.29 (CH), 34.64 (CH), 28.03 (CH$_3$), 26.45 (CH$_3$), 25.30 (CH$_3$) and 25.04 (CH$_3$).

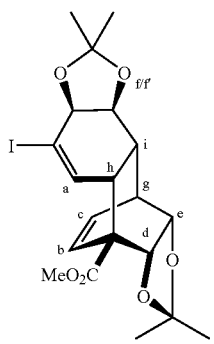

39

Properties: mp 166–167° C. (colourless cubic crystals, EtOAc). HRMS-EI: C$_{20}$H$_{25}$IO$_6$ requires 488.0696; found 488.0696. [α]$_D^{18}$+134.4° (c 0.73, CHCl$_3$). IR (KBr)/cm$^{-1}$: 3025, 2991, 2954, 2925, 2890, 1739 (s), 1643, 1438, 1380, 1368, 1317, 1272, 1259, 1230, 1159, 1100, 1075 (s), 1055, 874 and 744. MS-EI: 488 (0.2%, M$^{+*}$), 473 (36, [M–CH$_3$]$^+$), 457 (12), 430 (96), 415 (24), 399 (23), 372 (60), 361 (68), 328 (26), 313 (34), 245 (91), 228 (46), 220 (100), 213 (80), 186 (49), 185 (55), 157 (48), 153 (61), 129 (56), 128 (57), 121 (42) and 115 (37). $^1$H: 6.46 (1H, d, J 8.4), 6.05 (1H, dd, J 8.4, J 7.0), 6.00 (1H, d, J 4.0), 4.53 (1H, d, J 7.3), 4.39 (1H, dd, J 7.2, J 3.4), 4.20 (1H, d, J 4.7), 4.08 (1H, d, J 4.4), 3.87 (3H, s), 2.96–2.93 (1H, m), 2.83 (1H, dd, J 8.9, J 4.1), 2.41 (1H, d, J 8.9), 1.41 (3H, s), 1.35 (3H, s), 1.29 (3H, s) and 1.26 (3H, s). $^{13}$C: 172.05 (C), 136.42 (CH), 130.57 (CH), 128.19 (CH), 109.75 (C), 108.40 (C), 103.62 (C), 80.17 (CH), 78.33 (CH), 78.28 (CH), 74.77 (CH), 54.19 (C), 52.66 (CH$_3$), 41.14 (CH), 40.77 (CH), 33.61 (CH), 27.84 (CH$_3$), 26.65 (CH$_3$), 25.37 (CH$_3$) and 25.11 (CH$_3$).

EXAMPLE 8

Formation of Linked Cyclitols by Reaction of Epoxides with bis-Amines

Procedure A

A solution of iodo-epoxide 10 (0.807 g, 2.74 mmol) and 1,6-hexanediamine (0.159 g, 1.37 mmol, 0.5 eq) in DCM (10 mL) was stirred in the dark for 4 days. The resulting mixture (containing a white solid) was treated with n-hexane (10 mL) and the ensuing mixture filtered to give first crop of dimer 16b (0.518 g) as colourless needles. The filtrate was separated by column chromatography (silica, CHCl$_3$-MeOH 100:5) to give the second crop of product (0.200 g, total.74%).

Procedure B

Procedure A was followed except that the mixture was stirred at 80° C. in a sealed tube overnight. Under such conditions, dimer 16b was obtained in quantitative yield.

Procedure C

A solution of iodo-epoxide 10 (4.5–5 eq) and the appropriate bis-amine (1 eq) in DCM (0.4 M) was stirred in darkness at 120° C. for 2–9 days. The resulting mixture was separated by column chromatography (silica) eluted with n-hexane-EtOAc (4:1 to 3:1) to return unreacted epoxide 10 and chlorohydrins 41 and 42, n-hexane-EtOAc (1:1 to 1:2) for tetrameric 18 product and CHCl$_3$-MeOH (95:5) for trimer 17 and dimer 16.

Procedure D

A solution of iodo-epoxide 10 (4.3 eq) and the appropriate bis-amine (1 eq) in DCM (0.4 M) was pressurised at 19 kbar for 24 h. After depressurisation, the resulting mixture was subject to column chromatography (silica 4:1 v/v n-hexane-EtOAc elution) to afford unreacted epoxide 10 and, after elution of the column with n-hexane-EtOAc (1:1 to 1:2), the tetrameric product 18.

Details of the specific linked cyclitols synthesised follow.

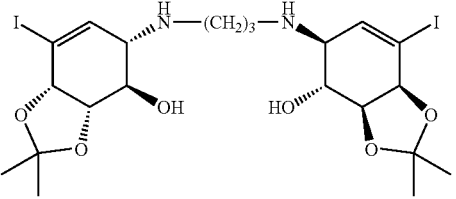

16a

Properties: mp 98–102° C. (off-white solid). [α]$_D^{18}$–52.1° (c 1.24, CHCl$_3$). IR (CHCl$_3$)/cm$^{-1}$: 3365, 2986, 2929, 2855, 1629, 1454, 1380, 1246, 1216, 1163, 1069, 1016, 868 and 753. $^1$H: 6.43 (2H, d, J 1.5), 4.67 (2H, d, J 6.0), 4.07 (2H, dd, J 8.7, J 6.6), 3.85 (2H, br s), 3.63 (2H, dd, J 9.3, J 8.7), 3.17 (2H, dm, J 9.3), 2.92–2.80 (4H, br m), 1.69 (2H, br m), 1.57 (6H, s) and 1.41 (6H, s). $^{13}$C: 143.24, 109.84, 93.01, 79.51, 78.58, 72.75, 69.51, 66.94, 45.53, 28.18, 25.63 and 25.21.

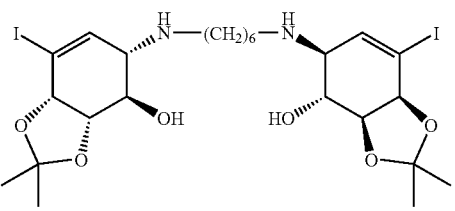

16b

Properties: mp 65–66° C. (colourless needles, n-hexane-dichloromethane). HRMS-EI: M–CH$_3$ (C$_{23}$H$_{35}$I$_2$N$_3$O$_6$) requires 689.0585; Found 689.0589. [α]$_D^{18}$+40.3° (c 0.365, CHCl$_3$). IR (KBr)/cm$^{-1}$: 3425, 2983, 2928, 2854, 1629, 1457, 1379, 1247, 1216, 1163, 1070, 911, 868, 790 and 742. MS-EI: 689 (20%, [M–CH$_3$]$^+$), 604 (51), 577 (30), 446 (13), 409 (42), 391 (42), 376 (14), 355 (21), 312 (11), 264 (11) and 241 (53). $^1$H: 6.53 (2H, s), 4.68 (2H, d, J 6.6), 4.14 (2H, dd, J 8.4, J 6.6), 3.48 (2H, dd, J 8.9, J 8.2), 3.04 (2H, d, J 8.2), 2.77 (2H, ddd, J 11.2, J 6.9, J 6.7), 2.53 (2H, ddd, J 11.2, J 6.9, J 6.7), 1.54 (6H, s), 1.41 (6H, s), 1.54–1.24 (8H, m, overlapped with methyl singlets at δ 1.54 and δ 1.41). $^{13}$C: 141.88 (CH), 109.84 (C), 93.51 (C), 79.38 (CH), 78.08 (CH), 71.16 (CH), 61.12 (CH), 46.38 (CH$_2$), 30.11 (CH$_2$), 28.12 (CH$_3$), 26.97 (CH$_2$), 25.79 (CH$_3$).

(CH), 70.46 (CH), 69.90 (CH), 61.05 (CH, broadened), 60.79 (CH), 47.23 (CH$_2$), 45.91 (CH$_2$), 29.72 (CH$_2$), 28.54 (CH$_2$), 28.01 (CH$_3$), 27.96 (CH$_3$), 26.47 (CH$_2$), 25.98 (CH$_2$), 25.73 (CH$_3$) and 25.50 (CH$_3$).

16d

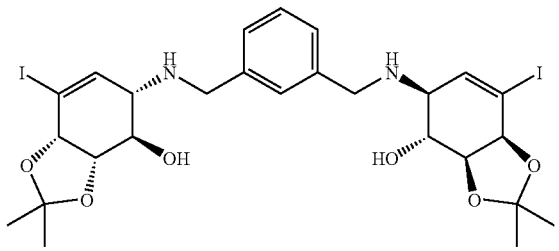

Properties: white foam. HRMS-EI: C$_{26}$H$_{34}$I$_2$N$_2$O$_6$ requires 724.0506; Found 724.0501. [α]$_D^{18}$+53.7° (c 1.05, CHCl$_3$). IR (CHCl$_3$)/cm$^{-1}$: 3308, 2986, 2930, 1628, 1454, 1380, 1216, 1162, 1070, 867 and 753. MS-EI: 724 (2%, M$^{+*}$), 709 (5, [M–CH$_3$]$^+$), 624 (100), 597 (11), 539 (20), 497 (5) and 415 (11). $^1$H: 7.36–7.20 (4H, m), 6.56 (2H, d, J 1.7), 4.66 (2H, d, J 6.6), 4.11 (2H, dd, J 8.2, J 6.6), 3.95 (2H, d, J 13.1), 3.75 (2H, d, J 13.1), 3.53 (2H, dd, J 8.5, J 8.2), 3.10 (2H, dd, J 8.5, J 1.7), 3.00–2.00 (4H, broadened signal, 2×NH and 2×OH), 1.51 (6H, s) and 1.40 (6H, s). $^{13}$C: 141.19 (CH), 139.53 (C), 128.71 (CH), 127.90 (CH), 127.25 (CH), 109.73 (C), 94.19 (C), 79.16 (CH), 77.85 (CH), 70.83 (CH), 60.16 (CH), 50.31 (CH$_2$), 27.99 (CH$_3$) and 25.74 (CH$_3$).

17e

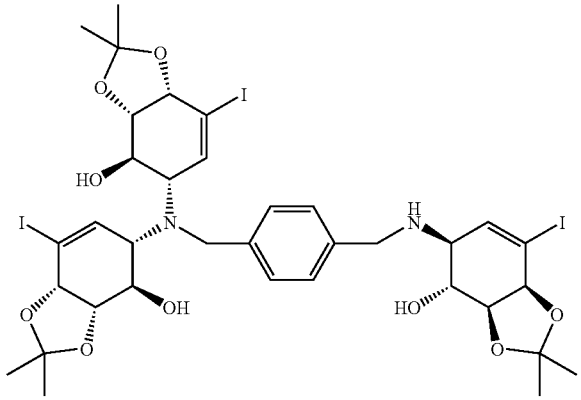

Properties: mp 122–126° C. (pale-yellow crystals). [α]$_D^{18}$+123.7° (c 3.46, CHCl$_3$). IR (CHCl$_3$)/cm$^{-1}$: 3400, 2987, 2932, 1623, 1454, 1380, 1247, 1215, 1163, 1071, 1018, 971, 909, 866 and 754. MS-ES: 1041 ([M+Na]$^+$), 1019 ([M+H]$^+$). $^1$H: 7.29 (4H, m), 6.56 (3H, s), 4.66–4.60 (3H, m), 4.15–4.04 (3H, m), 3.97–3.80 (5H, m), 3.72 (2H, d, J 13.1), 3.59–3.47 (4H, m), 3.27 (2H, d, J 8.7), 3.11 (1H, d, J 8.3), 1.50 (9H, s), 1.39 (3H, s) and 1.38 (6H, s). $^{13}$C: 141.69 (CH), 141.00 (CH), 138.16 (C), 137.28 (C), 128.56 (CH), 128.28 (CH), 109.56 (C), 94.24 (C), 93.62 (C), 79.06 (CH), 78.97 (CH), 77.71 (CH), 70.47 (CH), 69.94 (CH), 60.87 (CH), 59.93 (CH), 51.53 (CH$_2$), 49.94 (CH$_2$), 27.86 (CH$_3$), 25.64 (CH$_3$), 25.38 (CH$_3$).

17b

Properties: brownish gum, yield 40%. HRMS-FAB: M+H$^+$ (C$_{33}$H$_{50}$I$_3$N$_2$O$_9$) requires 999.0651; Found 999.0636. [α]$_D^{18}$+63.8° (c 2.51, CHCl$_3$). IR (CHCl$_3$)/cm$^{-1}$: 3391, 2986, 2931, 2857, 1623, 1455, 1380, 1246, 1215, 1163, 1071 (s), 910, 867, 788 and 753 (m). MS-FAB: 1021 ([M+Na]$^+$) and 999 ([M+H]$^+$); MS-EI: 983 (8%, [M–CH$_3$]$^+$), 898 (36), 871 (76), 813 (12), 771 (18), 703 (35), 128 (70) and 110 (100). $^1$H: 6.52 (1H, s), 6.46 (2H, s), 4.67 (3H, d, J 6.2), 4.16–4.10 (3H, m), 3.57 (1H, t, J 8.2), 3.39 (2H, t, J 8.9), 3.23 (2H, d, J 9.3), 3.07 (1H, d, J 7.7), 3.8–2.9 (4H, broadened signal), 2.82–2.68 (2H, m), 2.63–2.45 (2H, m), 1.54 (6H, s), 1.52 (3H, s), 1.40 (9H, s) and 1.60–1.20 (8H, m, (CH$_2$)$_4$ overlapping with methyl singlets). $^{13}$C: 142.53 (CH), 141.26 (CH), 110.66 (C), 109.64 (C), 94.13 (C), 93.24 (C), 79.25 (CH), 79.16 (CH), 77.98 (CH), 77.88

17d

Properties: mp 128–132° C. (off-white solid). HRMS-FAB: M+H (C$_{35}$H$_{46}$I$_3$N$_2$O$_9$) requires 1019.0338; Found 1019.0347. [α]$_D^{18}$+91.4° (c 2.34, CHCl$_3$). IR (CHCl$_3$)/cm$^{-1}$: 3391, 2986, 2931, 1623, 1453, 1380, 1246, 1215, 1162, 1071 (s), 971, 866, and 753. MS-FAB: 1019 ([M+H]$^+$). $^1$H: 7.48 (1H, s), 7.26 (1H, dd, J 7.3, J 6.7), 7.17 (2H, d, J 7.3), 6.58 (2H, s), 6.51 (1H, d, J 1.8), 4.64–3.73 (14H, m), 3.57 (1H, dd, J 8.4, J 7.7), 3.43 (2H, d, J 9.3, J 8.8), 3.28 (2H, d, J 9.3), 3.07 (1H, d, J 7.7), 1.50 (3H, s), 1.49 (6H, s), 1.38 (3H, s) and 1.37 (6H, s). $^{13}$C: 141.71, 140.85, 139.42, 138.77, 128.47, 128.14, 127.44, 127.37, 109.58 (2×C overlapping), 94.65, 93.64, 79.17, 78.95, 77.74, 77.65; 70.57, 70.00, 61.46, 59.53, 51.87, 50.11, 27.90 (2×CH$_3$ overlapping), 25.67 and 25.48.

79.32 (CH), 77.81 (CH), 70.19 (CH), 61.63 (CH), 45.55 (CH$_2$), 29.37 (CH$_2$), 28.11 (CH$_3$) and 25.58 (CH$_3$).

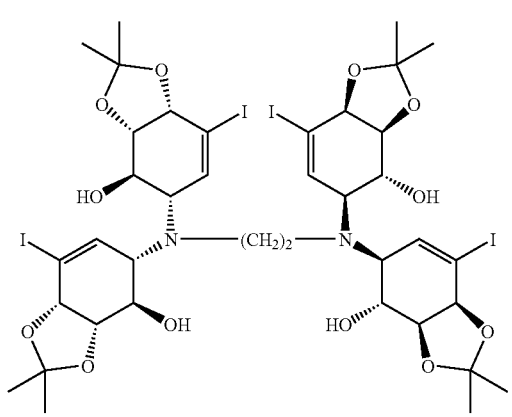

18f

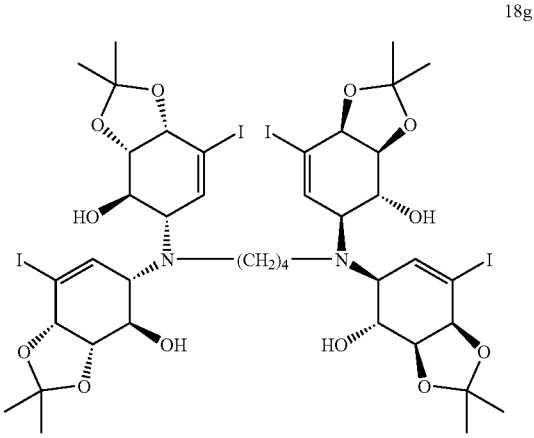

18g

Properties: mp 139–141° C. (white waxy solid) 66%. HRMS-FAB: M+H (C$_{38}$H$_{53}$I$_4$N$_2$O$_{12}$) requires 1236.9778; Found 1236.9809. [α]$_D^{18}$+139.2° (c 3.11, CHCl$_3$). IR (CHCl$_3$)/cm$^{-1}$: 3410, 2984, 2923, 1624, 1454, 1374, 1245, 1215, 1163, 1073 (s), 992, and 870. MS-ES: 1259 ([M+Na]$^+$), 1237 ([M+H]$^+$); MS-FAB: 1259 ([M+Na]$^+$), 1237 ([M+H]$^{+*}$). $^1$H: 6.45 (4H, s), 4.69 (4H, br s), 4.66 (4H, d, J 6.6), 4.13 (4H, dd, J 8.5, J 6.6), 34.41 (4H, dd, J 9.3, J 8.2), 3.26 (4H, d, J 9.3), 2.84–2.75 (4H, br m), 1.54 (12H, s) and 1.40 (12H, s). $^{13}$C: 141.74 (CH), 109.65 (C), 94.05 (C), 79.19 (CH), 77.66 (CH), 69.92 (CH), 61.31 (CH), 46.36 (CH$_2$), 27.95 (CH$_3$) and 25.40 (CH$_3$).

Properties: mp 132–136° C. (white solid) 87%. RMS-FAB: M+H (C$_{40}$H$_{57}$I$_4$N$_2$O$_{12}$) requires 1265.0091; Found 1265.0101. [α]$_D^{18}$+131.2° (c 0.79, CHCl$_3$). IR (CHCl$_3$)/cm$^{-1}$: 3419, 2985, 2932, 1625, 1454, 1380, 1247, 1215, 1162, 1071, 910, 866 and 752. MS-ES: 1287 ([M+Na]$^+$), 1265 ([M+H]$^+$); MS-FAB: 1287 (M+Na]$^+$), 1265 ([M+H]$^+$). $^1$H: 6.44 (4H, s), 4.65 (4H, d, J 6.3), 4.36 (4H, br s), 4.15 (4H, dd, J 7.9, J 6.3), 3.35 (4H, dd, J 9.1, J 7.3), 3.23 (4H, d, J 9.1), 2.87 (2H, br d, J 12.9), 2.52 (2H, br m), 1.74 (4H, br s), 1.54 (12H, s) and 1.40 (12H, s). $^{13}$C: 141.85 (CH), 109.63 (C), 93.51 (C), 79.21 (CH), 77.68 (CH), 70.19 (CH), 60.67 (CH), 47.08 (CH$_2$), 27.95 (CH$_3$), 25.43 (CH$_3$) and 25.16 (CH$_2$).

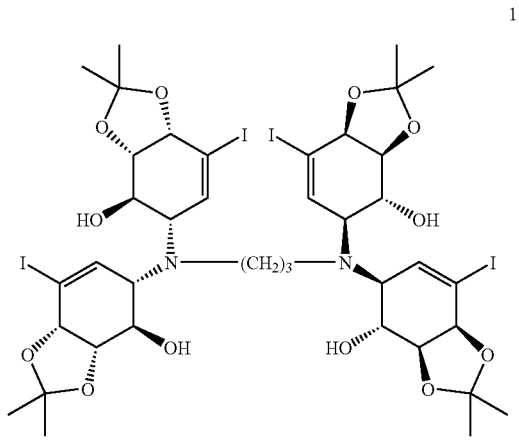

18a

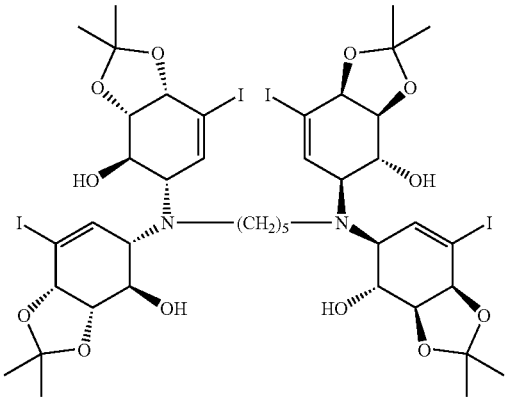

18k

Properties: mp 160–162.5° C. (off-white solid) 92%. HRMS-FAB: M+H (C$_{39}$H$_{55}$I$_4$N$_2$O$_{12}$) requires 1250.9934; Found 1250.9936. [α]$_D^{18}$+125.5° (c 0.98, CHCl$_3$). IR (CHCl$_3$)/cm$^{-1}$: 3435, 2986, 2934, 1630, 1455, 1380, 1247, 1214, 1162, 1071, 866 and 752. MS-FAB: 1273 ([M+Na]$^+$), 1251 ([M+H]$^+$); MS-ES: 1272 ([M+Na]$^+$), 1251 ([M+H]$^+$). $^1$H: 6.43 (4H, s), 4.67 (4H, d, J 6.5), 4.13 (4H, dd, J 8.8, J 6.5), 3.94 (4H, br s), 3.37 (4H, dd, J 9.3, J 8.8), 3.22 (4H, d, J 9.3), 2.87–2.81 (2H, m), 2.63–2.57 (2H, m), 1.55 (12H, s), 1.41 (12H, s), 1.61–1.24 [2H, m, CH$_2$ overlapping with methyl singlets]. $^{13}$C: 142.57 (CH), 109.87 (C), 93.36 (C), Properties: mp 118–122° C. (white solid) 73%. HRMS-FAB: M+H (C$_{41}$H$_{59}$I$_4$N$_2$O$_{12}$) requires 1279.0247; Found 1279.0241. [α]$_D^{18}$+129.3° (c 0.80, CHCl$_3$). IR (CHCl$_3$)/cm$^{-1}$: 3399, 2985, 2930, 1621, 1454, 1379, 1246, 1215, 1163, 1071 (s), 1000, 866 and 753. MS-ES: 1301 ([M+Na]$^+$), 1279 ([M+H]$^+$); MS-FAB: 1301 (M+Na]$^+$), 1279 ([M+H]$^{+*}$). $^1$H: 6.45 (4H, s), 4.65 (4H, d, J 6.3), 4.34 (4H, br s), 4.15 (4H, dd, J 8.4, J 6.3), 3.37 (4H, dd, J 9.0, J 8.7), 3.21 (4H, d, J 9.0), 2.75 (2H, br m), 2.58 (2H, br m), 1.53 (12H, s), 1.40 (12H, s) and 1.70–1.25 [6H, m, (CH$_2$)$_3$ overlapping with methyl singlets]. $^{13}$C: 145.57 (CH), 112.94 (C), 96.74

(C), 82.53 (CH), 81.17 (CH), 73.33 (CH), 64.40 (CH), 50.86 (CH$_2$), 32.01 (CH$_2$), 31.28 (CH$_3$), 28.80 (CH$_3$) and 27.10 (CH$_2$).

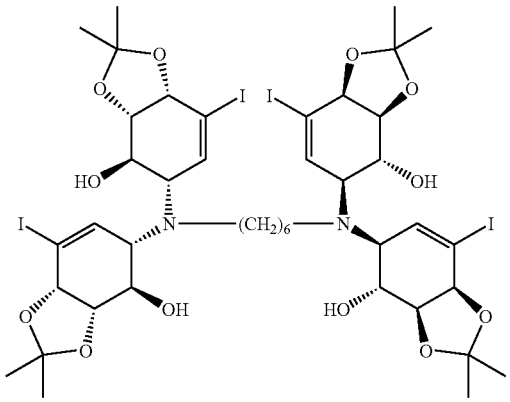

18b

Properties: mp 129–132° C. (pale-yellow solid) 68%. HRMS-FAB: M+Na$^+$ (C$_{42}$H$_{60}$I$_4$N$_2$NaO$_{12}$) requires 1315.0223; Found 1315.0220. M+H$^+$ (C$_{42}$H$_{61}$I$_4$N$_2$O$_{12}$) requires 1293.0404; Found 1293.0459. [α]$_D^{18}$+167.1° (c 1.94, CHCl$_3$). IR (CHCl$_2$)/cm$^{-1}$: 3400, 2987, 2932, 2859, 1621, 1455, 1380, 1246, 1216, 1163, 1071 (s), 100, 911, 866 and 754 (m). MS-FAB: 1315 ([M+Na]$^+$), 1293 ([M+H]$^+$). $^1$H: 6.45 (4H, s), 4.66 (4H, d, J 6.6), 4.14 (8H, dd, J 8.8, J 6.6, containing 4×OH), 3.37 (4H, dd, J 9.5, J 8.8), 3.22 (4H, d, J 9.5), 2.77–2.69 (2H, m), 2.60–2.51 (2H, m), 1.54 (12H, s), 1.40 (12H, s) and 1.60–1.20 (8H, m, —(CH$_2$)$_4$— overlapping with methyl singlets). $^{13}$C: 142.62 (CH), 109.67 (C), 93.19 (C), 79.24 (CH), 77.85 (CH), 70.04 (CH), 61.30 (CH, lump, NCH), 47.83 (CH$_2$), 29.05 (CH$_2$), 28.01 (CH$_3$), 26.32 (CH$_2$) and 25.51 (CH$_3$).

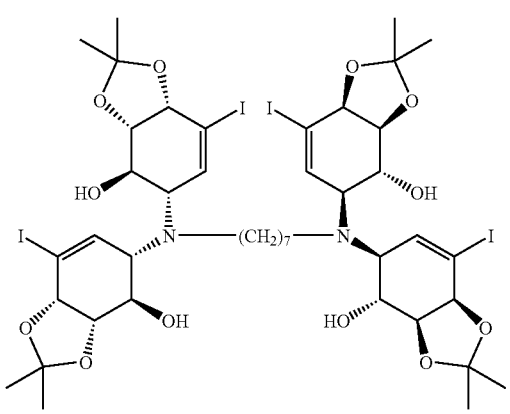

18h

Properties: mp 109–112° C. (white solid) 91%. HRMS-FAB: M+H$^+$ (C$_{43}$H$_{63}$I$_4$N$_2$O$_{12}$) requires 1307.0560; Found 1307.0532. [α]$_D^{18}$+122.9° (c 1.09, CHCl$_3$). IR (CHCl$_3$)/cm$^{-1}$: 3394, 2926, 1620, 1380, 1245, 1215, 1162, 1071 and 867. MS-ES: 1330 (11%, [M+Na]$^+$), 1307 (27, [M+H]$^+$), 703 (100). MS-FAB: 1330 (M+Na]$^+$), 1307 ([M+H]$^+$). $^1$H: 6.45 (4H, s), 4.66 (4H, d, J 6.5), 4.18 (4H, br s), 4.15 (4H, dd, J 8.4, J 6.9), 3.37(4H, dd, J 9.3, J 9.1), 3.21 (4H, d, J 9.1), 2.82–2.68 (2H, br m), 2.62–2.50 (2H, br m), 1.54 (12H, s), 1.40 (12H, s) and 1.60–1.20 [10H, m, (CH$_2$)$_5$ overlapping with methyl singlets]. $^{13}$C: 142.40 (CH), 109.53 (C), 93.20 (C), 79.15 (CH), 77.79 (CH), 69.94 (CH), 61.07 (CH), 47.45 (CH$_2$), 28.76 (CH$_2$), 28.59 (CH$_2$), 27.95 (CH$_3$), 25.80 (CH$_2$) and 25.47 (CH$_3$).

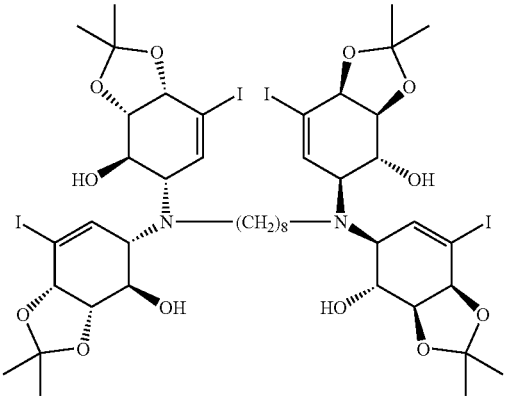

18i

Properties: mp 114–116° C. (white solid) 97%. HRMS-FAB: M+H$^+$ (C$_{44}$H$_{65}$I$_4$N$_2$O$_{12}$) requires 1321.0717; Found 1321.0724. [α]$_D^{18}$+128.7° (c 0.87, CHCl$_3$). IR (CHCl$_3$)/cm$^{-1}$: 3399, 2986, 2928, 1619, 1380, 1246, 1215, 1162, 1071 (s), 867 and 753. MS-ES: 1343 ([M+Na]$^+$), 1321 ([M+H]$^+$); MS-FAB: 1343 (M+Na]$^+$), 1321 ([M+H]$^+$). $^1$H: 6.45 (4H, s), 4.65 (4H, d, J 6.5), 4.94 (4H, br s), 4.14 (4H, dd, J 9.1, J 6.5), 3.36 (4H, dd, J 9.1, J 8.8), 3.22 (4H, d, J 8.8), 2.79–2.64 (2H, br m), 2.64–2.48 (2H, br m), 1.53 (12H, s), 1.39 (12H, S), 1.60–1.10 [12H, m, (CH$_2$)$_6$ overlapping with methyl singlets]. $^{13}$C: 142.36 (CH), 109.33 (C), 93.01 (C), 78.94 (CH), 77.67 (CH), 69.67 (CH), 61.06 (CH), 47.61 (CH$_2$), 28.93 (CH$_2$), 28.87 (CH$_2$), 27.76 (CH$_3$), 26.18 (CH$_2$) and 25.28 (CH$_3$).

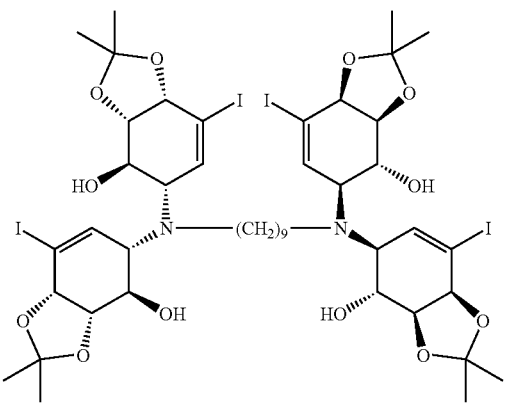

18j

Properties: Yield 85% (19 kbar, 24 h). mp 100–104° C. (white solid). HRMS-FAB: M+H (C$_{45}$H$_{67}$I$_4$N$_2$O$_{12}$) requires 1335.0873; Found 1335.0872. [α]$_D^{18}$+132.6° (c 0.90, CHCl$_3$). IR (CHCl$_3$)/cm$^{-1}$: 3401, 2985, 2926, 2854, 1620, 1455, 1380, 1246, 1215, 1163, 1072 (s), 911, 867 (m), 826, 788 and 753 (m). MS-ES: 1357 ([M+Na]$^+$), 1335 ([M+H]$^+$); MS-FAB: 1357 (M+Na]$^+$), 1335 ([M+H]$^+$). $^1$H: 6.46 (4H, s), 4.67 (4H, d, J 6.6), 4.12 (4H, dd, J 8.5, J 6.7), 3.87 (4H, br s), 3.39 (4H, dd, J 9.2, J 9.1), 3.22 (4H, d, J 9.2), 2.78–2.70 (2H, br m), 2.60–2.52 (2H, br m), 1.55 (12H, s), 1.41 (12H, s) and 1.68–1.20 [14H, m, (CH$_2$)$_7$ overlapping with methyl singlets]. $^{13}$C: 142.63 (CH), 109.56 (C), 93.07 (C), 79.16 (CH), 77.85 (CH), 69.88 (CH), 61.30 (CH), 47.84 (CH$_2$), 29.10 (CH$_2$), 28.99 (CH$_2$), 28.96 (CH$_2$), 27.91 (CH$_3$), 26.40 (CH$_2$) and 25.44 (CH$_3$).

7.23 (1H, dd, J 7.0, J 6.7), 7.13 (2H, d, J 7.1), 6.58 (4H, s), 4.63 (4H, d, J 6.6), 4.32 (4H, br s), 4.06 (4H, dd, J 8.8, J 6.6), 3.94 (2H, d, J 14.3), 3.80 (2H, d, J 14.3), 3.47 (4H, dd, J 9.3, J 8.8), 3.25 (4H, d, J 8.8), 1.50 (12H, s) and 1.37 (12H, s). $^{13}$C: 141.60 (CH), 138.66 (C), 128.84 (CH), 128.31 (CH), 127.92 (CH), 109.58 (C), 93.78 (C), 79.19 (CH), 77.71 (CH), 70.02 (CH), 61.07 (CH), 51.87 (CH$_2$), 27.92 (CH$_3$) and 25.49 (CH$_3$).

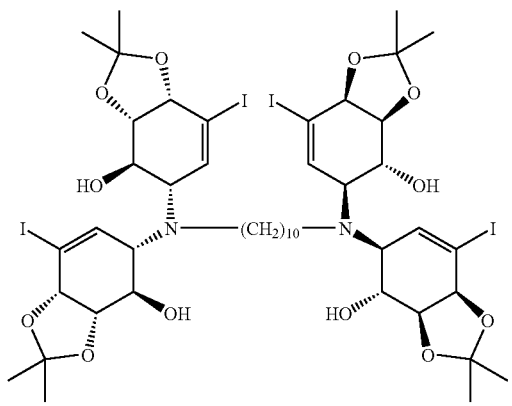

18c

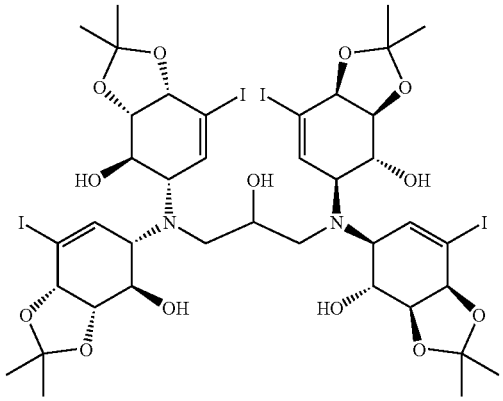

18e

Properties: mp 120–123° C. (pale-yellow solid). HRMS-FAB: M+H$^+$ (C$_{46}$H$_{68}$I$_4$N$_2$O$_{12}$) requires 1349.1030; Found 1349.1031. [α]$_D^{18}$+123.4° (c 0.54, CHCl$_3$). IR (CHCl$_3$)/cm$^{-1}$: 3392, 2986, 2927, 1621, 1455, 1380, 1246, 1215, 1163, 1072 (s), 866 and 754. MS-ES: 1371 ([M+Na]$^+$), 1349 ([M+H]$^+$); MS-FAB: 1371 ([M+Na]$^+$), 1349 ([M+H]$^+$). $^1$H: 6.46 (4H, s), 4.66 (4H, d, J 6.6), 4.35 (4H, br s), 4.16 (4H, dd, J 8.6, J 6.6), 3.36 (4H, dd, J 9.4, J 8.3), 3.23 (4H, d, J 9.4), 2.78–2.66 (2H, m), 2.62–2.48 (2H, m), 1.55 (12H, s), 1.40 (12H, s) and 1.61–1.18 [16H, m, (CH$_2$)$_8$ overlapping with methyl singlets]. $^{13}$C: 142.75 (CH), 109.67 (C), 93.23 (C), 79.27 (CH), 77.93 (CH), 70.06 (CH), 61.33 (CH), 48.01 (CH$_2$), 29.04 (CH$_2$), 28.78 (CH$_2$). 28.55 (CH$_2$), 27.94 (CH$_3$), 26.32 (CH$_2$) and 25.50 (CH$_3$).

Properties: mp 169–171° C. (colourless crystals, CHCl$_3$). HRMS-FAB: M+H (C$_{44}$H$_{57}$I$_4$N$_2$O$_{12}$) requires 1313.0091; Found 1313.0099. [α]$_D^{18}$+152.8° (c 0.91, CHCl$_3$). IR (CHCl$_3$)/cm$^{-1}$: 3377, 2984, 2924, 1621, 1452, 1375, 1248, 1211, 1163, 1071 (s), 973, 867 and 753. MS-ES: 1335 ([M+Na]$^+$), 1313 ([M+H]$^+$). MS-FAB: 1313 ([M+H]$^+$). $^1$H: 7.29 (4H, s), 6.56 (4H, s), 4.64 (4H, d, J 6.5), 4.09 (4H, dd, J 9.0, J 6.5), 4.03 (4H, br s), 3.94 (2H, d, J 14.7), 3.84 (2H, d, J 14.7), 3.52 (4H, dd, J 9.2, J 9.0), 3.29 (4H, d, J 9.2), 1.53 (12H, s) and 1.39 (12H, s). $^{13}$C: 141.99, 137.68, 128.71, 109.84, 93.59, 79.34, 77.84, 70.22, 61.12, 51.87, 29.63, 28.05 and 25.55.

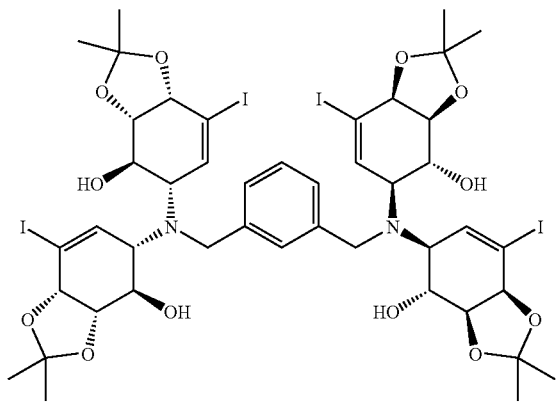

18d

18[linker: —CH$_2$CH(OH)CH$_2$—]

Properties: mp 159–162° C. (off-white solid). HRMS-FAB: M+H (C$_{44}$H$_{57}$I$_4$N$_2$O$_{12}$) requires 1313.0091; Found 1313.0091. [α]$_D^{18}$+147.3° (c 1.34, CHCl$_3$). IR (CHCl$_3$)/cm$^{-1}$: 3408, 2986, 2932, 1621, 1453, 1379, 1246, 1215, 1163, 1071 (s), 975, 866 and 753. MS-ES: 1335 ([M+Na]$^+$), 1313 ([M+H]$^+$); MS-FAB: 1313 ([M+H]$^+$). $^1$H: 7.46 (1H, s), Properties: Yield 22%; pale-yellow foam. HRMS-FAB: M+H (C$_{39}$H$_{55}$I$_4$N$_2$I$_{13}$) requires 1266.9883; Found 1266.9915. [α]$_D^{18}$+113.4° (c 0.62, CHCl$_3$). IR (CHCl$_3$)/cm$^{-1}$: 3400, 2985, 2933, 1622, 1455, 1380, 1250, 1214, 1162, 1071 (s), 997, 910, 866 (m), 823, 787, 752 (m) and 658. MS-FAB: 1289 (M+Na)$^+$), 1267 ([M+H]$^+$). $^1$H: 6.43

(4H, s), 4.67 (4H, m), 4.60 (4H, br s), 4.13 (4H, br m), 3.66 (2H, br s), 3.34 (4H, m), 3.21 (2H, m), 2.86–2.65 (4H, m), 2.48–2.38 (2H, m), 1.54 (12H, s) and 1.40 (12H, s).

23

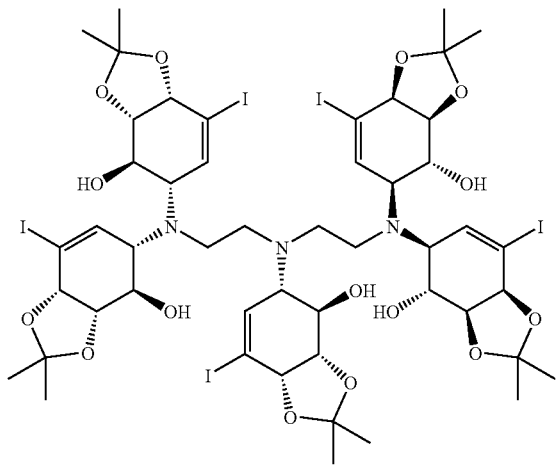

Properties: mp 165–167° C. (white solid, EtOAc). $[\alpha]_D^{18}$+104.3° (c 2.50, CHCl$_3$). IR (CHCl$_3$)/cm$^{-1}$: 3400, 2986, 2933, 1621, 1455, 1380, 1247, 1216, 1162, 1072, 995, 866 and 754. MS-ES: 1596 ([M+Na]$^+$), 1574 ([M+H]$^+$); MS-FAB: 1596 ([M+Na]$^+$), 1574 ([M+H]$^+$). $^1$H: 6.45 (5H, broadened signal), 4.67 (4H, d, 6.6), 4.63 (1H, d, 6.9), 4.32 (4H, br s, OH), 4.17–4.12 (5H, m), 3.68 (1H, br s, OH), 3.45–3.25 (10H, m), 2.81 (4H, br s), 2.71–2.66 (2H, m), 2.52–2.47 (2H, m), 1.55 (15H, s) and 1.41 (15H, s). $^{13}$C: 142.08, 140.25, 109.69, 109.66, 93.99, 93.51, 79.40, 79.11, 78.30, 77.65, 69.94, 69.08, 64.32, 61.83, 50.96, 46.74, 28.17, 27.98, 25.69 and 25.41.

41

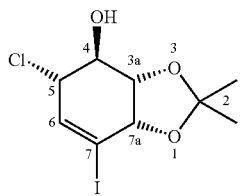

Properties: colourless gum. HRMS-EI: M–CH$_3$ (C$_8$H$_9$ClIO$_3$) requires $^{37}$Cl, 316.9255, $^{35}$Cl, 314.9285; found $^{37}$Cl, 316.9262, $^{35}$Cl, 314.9290. $[\alpha]_D^{18}$–19.9° (c 0.66, CHCl$_3$). IR (CHCl$_3$)/cm$^{-1}$: 3418, 2986, 2925, 1631, 1454, 1381, 1218, 1160, 1074(s) and 866. MS-EI: 330 (2%, M$^{+*}$), 317 (57, [M+2–CH$_3$]$^{+*}$), 315 (100, [M–CH$_3$]$^{+*}$), 257 (14), 255 (32), 209 (14), 207 (23), 229 (4), 227 (12), 130 (24) and 128 (45). $^1$H: 6.52 (1H, d, J$_{6,5}$ 2.1, H6), 4.71 (1H, d, J$_{7a,3a}$ 6.0, H7a), 4.31 (1H, ddd, J$_{5,4}$ 8.6, J$_{5,6}$ 2.1, $^4$J$_{5,3a}$ 1.5, H5), 4.14 (1H, dd, J$_{3a,4}$ 8.6, J$_{3a,7a}$ 6.3, H3a), 3.78 (1H, t, J$_{4,5}$ 8.6, J$_{4,3a}$ 8.6, H4), 3.00 (1H, br s, OH), 1.56 (3H, s) and 1.43 (3H, s) [Note: W-coupling between H3a and H5 (1.5 Hz)]. $^{13}$C: 140.13 (CH), 110.52 (C), 94.42 (C), 79.41 (CH), 77.20 (CH), 73.76 (CH), 59.90 (CH), 28.01 (CH$_3$) and 25.78 (CH$_3$). Note: W-coupling between H3a and H5 (1.5 Hz).

42

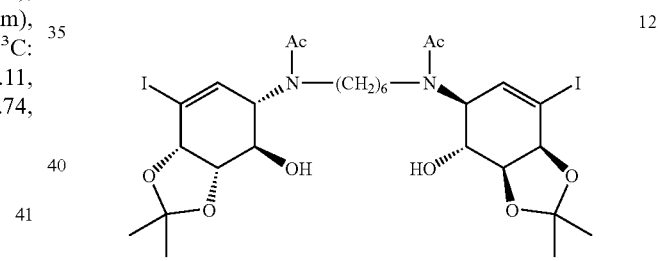

Properties: mp 105–107° C. (colourless needles). HRMS-EI: C$_9$H$_{12}$ClIO$_3$ requires $^{37}$Cl, 331.9490, $^{35}$Cl, 329.9520; found $^{37}$Cl, 331.9488, $^{35}$Cl, 329.9518. $[\alpha]_D^{18}$–18.5° (c 1.12, CHCl$_3$). IR (CHCl$_3$)/cm$^{-1}$: 3447, 2986, 2932, 1625, 1373, 1268, 1225, 1160, 1075(s), 1051, 869 and 853. MS-EI: 332 (2%, [M+2]$^+$), 330 (7, M$^{+*}$), 317 (52, [M+2–CH$_3$]$^+$), 315 (100, [M–CH$_3$]$^+$), 274 (7), 272 (22), 257 (5), 255 (15), 209 (14), 207 (19), 130 (30) and 128 (54). $^{13}$C: 136.33 (CH), 109.96 (C), 101.15 (C), 78.14 (CH), 75.93 (CH), 69.00 (CH), 58.47 (CH), 27.60 (CH$_3$) and 26.06 (CH$_3$).

Acetylation of Dimer 11: Formation of Compound 12

To a suspension of dimer 11 (0.521 g, 0.749 mmol) in DCM (14 mL) was added triethylamine (0.52 mL, 3.7 mmol, 5 eq). The resulting homogeneous solution was cooled at 0° C. and acetyl chloride (108 ml, 1.517 mmol, 2.05 eq) was added dropwise. The mixture was stirred at 0° C. for 3 h, then at 18° C. for 12 h, diluted with DCM (20 mL), washed with water, dried (MgSO$_4$), filtered, evaporated and the residue was separated by column (silica, CHCl$_3$-MeOH 100:5) to gave bis-acetamide 12.

12

Properties: Colourless gum (0.527 g, 90%). $[\alpha]_D^{18}$–2.9° (c 1.5, CHCl$_3$). IR (KBr)/cm$^{-1}$: 3411. 2986, 2930, 2857, 1623 (s), 1456, 1422, 1375, 1284, 1245, 1216, 1071 (s), 984, 867 and 749. MS-EI: 773 (10%, [M–CH$_3$]$^+$), 688 (6), 630 (22), 545 (13), 485 (9), 248 (16), 197 (13) and 128 (91). $^1$H NMR: two rotamers present in a molar ratio of 2:3 as determined by integration of olefinic resonances. Characteristic signals: major rotamer, 6.24 (2H, s), 2.14 (6H, s, NCOCH$_3$) and minor rotamer, 6.32 (2H, d, 6.1), 2.13 (6H, s, NCOCH$_3$). All signals (integration for total olefin protons δ 6.32 and δ 6.24 as two protons): 6.32 (0.8H, d, J 6.1), 6.24 (1.2H, s), 4.89 (0.8H, br s), 4.70 (3.2H, br m), 4.22–4.13 (4H, m), 3.90 (0.8H, br s), 3.75–3.56 (3.2H, br m), 3.38–3.02 (4H, m), 2.13 (2.4H, s), 2.14 (3.6H, s), 1.55 (6H, s), 1.42 (6H, s) and 1.70–1.28 (8H, m).

EXAMPLE 9

Pd[0]-catalysed Carbomethoxylation of Di-iodide 12

Following the general procedure outlined earlier for Pd(0)-catalysed carbomethoxylation, the bis-alkenyl iodide 12 was converted into the corresponding bis-ester 13 which was obtained after column chromatographic purification (silica, CHCl$_3$-MeOH 100:10).

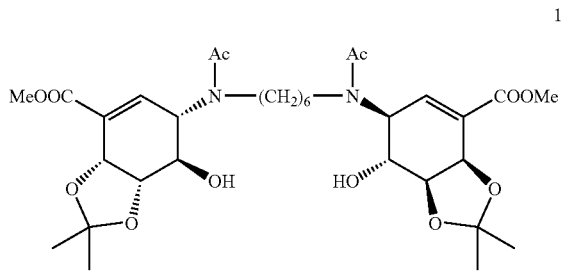

13

Properties: colourless gum, 33%. HRMS-EI: M−CH$_3$ (C$_{31}$H$_{45}$O$_{12}$N) requires 637.2973; found 637.2981. [α]$_D^{18}$ −6.2° (c 0.50, CHCl$_3$). IR (CHCl$_3$)/cm$^{-1}$: 3368, 2988, 2933, 2857, 1722 (s), 1626 (s), 1436, 1371, 1248, 1219, 1165, 1092, 1000, 919, 870, 755 and 665. MS-EI: 652 (10%, M$^{+*}$), 637 (12, [M−CH$_3$]$^+$), 500 (15), 458 (30), 292 (18), 248 (18), 209 (17) and 180 (76). $^1$H NMR: two rotamers present in molar ratio of 1:2 as determined by integration of olefinic resonances at δ 6.88 (s) and 6.84 (s). Signals at δ 6.88 (s) and δ 6.84 (s) account for 2 protons in total: δ 6.88 (0.66H, s), 6.84 (1.34H, s), 5.02–4.95 (3.34H, m), 4.32 (1.34H, br s), 4.18–4.13 (2.66H, m), 3.83 (0.99H, s), 3.80 (4H, s), 3.70 (2H, br m), 3.40–3.10 (4H, m), 2.16 (6H, s), 1.53 (6H, s), 1.46 (6H, s) and 1.78–1.25 (8H, m, overlapping with methyl singlets).

EXAMPLE 10

Deiodination of Tetramers 18

A magnetically stirred mixture of compound 18 (0.1 mmol) and 10% Pd/C (51 mg) in EtOAc (20 mL) and Et$_3$N (0.1 mL) was hydrogenated in a Parr reactor under a hydrogen atmosphere (55 PSI) for 5–24 h. The ensuing mixture was filtered through a plug of Celite™ and the filtrate concentrated under reduced pressure and purified by column chromatography (silica, CHCl$_3$-MeOH 100:5) to give pure deiodinated tetramer 21.

Details of the deiodination of other tetramers of the compound 18 class follow.

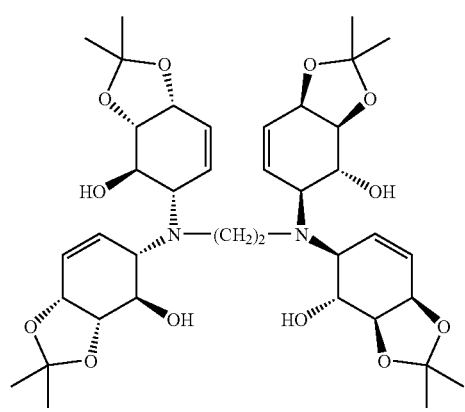

21f

Properties: Yield 77% (colourless foam). HRMS-EI: ½M (C$_{19}$H$_{28}$NO$_6$) requires 366.191663; Found 366.191668.

[α]$_D^{18}$ +33.7° (c 1.45, CHCl$_3$). IR (CHCl$_3$)/cm$^{-1}$: 3411, 2985, 2933, 1456, 1380, 1247, 1214, 1164, 1061 (s), 986, 895, 865 and 751. MS-EI: 732 (0.5%, M$^{+*}$), 717 (2, [M−CH$_3$]$^+$), 699 (0.8), 640 (1.1), 563 (17), 366 (100, 1/2M). $^1$H: 6.01–5.93 (8H, m), 4.74 (4H, br s), 4.59 (4H, d, J 6.6), 4.10(4H, dd, J 8.8, J 6.6), 3.40 (4H, dd, J 9.5, J 8.2), 3.21 (4H, d, J 9.5), 2.82 (4H, s), 1.52 (12H, s) and 1.37 (12H, s). $^{13}$H: 132.63, 125.68, 109.80, 78.28, 72.01, 70.61, 58.67, 46.15, 28.02 and 25.34.

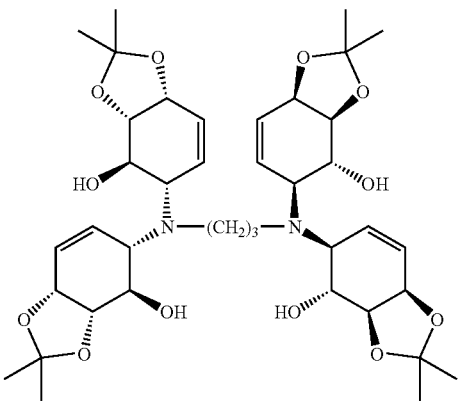

21a

Properties: Yield 60%, colourless foam. HRMS-EI: C$_{39}$H$_{58}$N$_2$O$_{12}$ requires 746.3990; Found 734.3995. [α]$_D^{18}$ +69.1° (c 1.08, CHCl$_3$). IR (CHCl$_3$)/cm$^{-1}$: 3400, 2985, 2933, 1380, 1245, 1215, 1165, 1060 (s), 894, 866 and 751. MS-EI: 747 (10%, [M+H]$^+$), 746 (7, M$^{+*}$), 731 (24, [M−CH$_3$]$^+$), 659 (9), 646 (79), 589 (13), 577 (77), 477 (32), 450 (12), 419 (11), 409 (14), 393 (30), 380 (56), 378 (48), 368 (60), 366 (99), 352 (26), 293 (54), 266 950) and 224 (100). $^1$H: 5.96–5.88 (8H, m), 4.59 (4H, d, J 5.6), 4.09 (4H, dd, J 8.8, J 6.6), 3.95 (4H, br s), 3.38 (4H, dd, J 9.5, J 8.8), 3.22 (4H, d, J 9.5), 2.95–2.84 (2H, m), 2.63–2.50 (2H, m), 2.44 (2H, br s), 1.52 (12H, s), and 1.39 (12H, s). $^{13}$C: 133.37, 125.21, 109.89, 78.47, 72.04, 70.77, 58.94, 45.28, 29.08, 28.09 and 25.51.

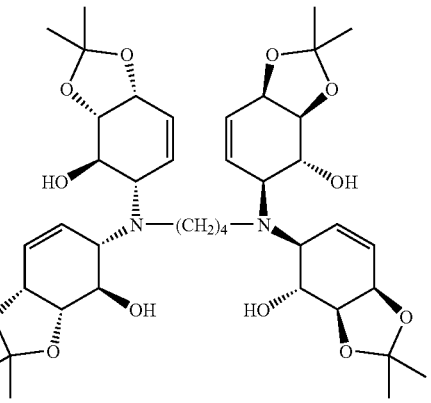

21g

Properties: Yield 84% colourless foam. HRMS-EI: C$_{40}$H$_{60}$N$_2$O$_{12}$ requires 760.4146; Found 760.4137. [α]$_D^{18}$ +66.1° (c 2.60, CHCl$_3$). IR (CHCl$_3$)/cm$^{-1}$: 3401, 2986, 2932, 2864, 1647, 1456, 1380, 1247, 1215, 1164, 1121, 1062 (s), 996, 896 (m), 867, 828, 752 (m), 697, 666, 622 and 502.

MS-EI: 760 (13%, M⁺*), 745 (12, [M–CH₃]⁺), 685 (4), 673 (20), 660 (100), 591 (40), 491 (10), 433 (8), 406 (12), 392 (8), 366 (12), 238 (51), 164 (11) and 138 (28). $^1$H: 5.93 (8H, br s), 4.58 (4H, d, J 6.6), 4.24 (4H, br s), 4.14 (4H, dd, J 8.3, J 7.1), 3.36 (4H, dd, J 9.2, J 9.1), 3.21 (4H, d, J 9.2), 2.91 (2H, br d, J 12.9), 2.55–2.48 (2H, m), 1.95–1.80 (2H, m), 1.52 (12H, s), 1.38 (12H, s) and 1.60–1.20 (2H, m, overlapping with methyl singlets). $^{13}$C: 132.66 (CH), 125.36 (CH), 109.78 (C), 78.36 (CH), 72.01 (CH), 70.95 (CH), 58.29 (CH), 46.93 (CH₂), 29.51 (CH₂), 28.03 (CH₃) and 25.40 (CH₃).

895, 865, 828, 751 (m), 697, 665 and 625. MS-EI: 788 (4%, M⁺*), 773 (5, [M–CH₃]⁺), 713 (6), 701 (688 (60), 619 (22), 519 (12), 461 (8) and 366 (8). $^1$H: 5.98–5.85 (8H, m), 4.60 (4H, d, J 6.6), 4.10 (4H, dd, J 8.7, J 6.6), 3.94 (4H, br s), 3.40 (4H, dd, J 9.5, J 8.7), 3.19 (4H, d, J 9.5), 2.79–2.68 (2H, m), 2.62–2.51 (2H, m), 1.53 (12H, s), 1.39 (12H, s), 1.75–1.15 (8H, m, overlapping with methyl singlets). $^{13}$C: 133.50 (CH), 125.05 (CH), 109.78 (C), 78.48 (CH), 71.98 (CH), 70.61 (CH), 58.74 (CH), 47.62 (CH₂), 29.21 (CH₂), 28.03 (CH₃), 26.46 (CH₂) and 25.94 (CH₃).

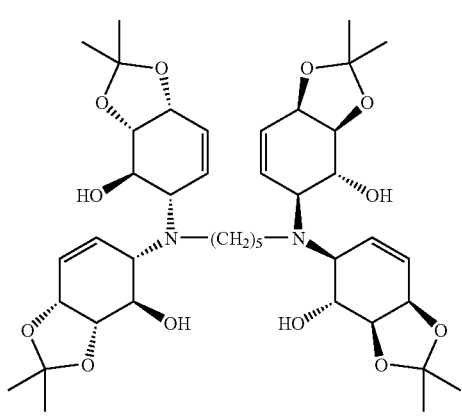

21k

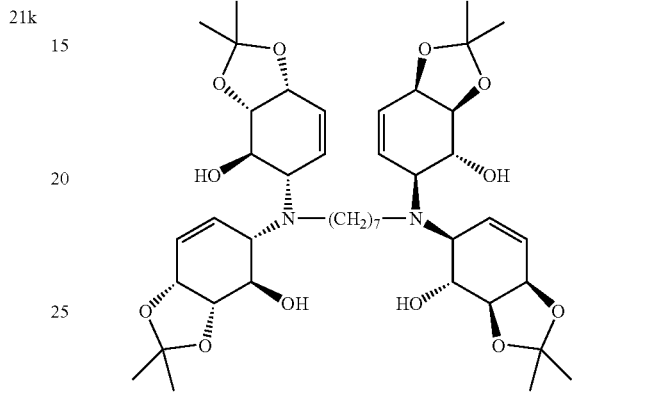

21h

Properties: Yield 48% colourless foam. HRMS-EI: C₄₁H₆₂N₂O₁₂ requires 774.4303; Found 774.4296. $[\alpha]_D^{18}$+ 69.6° (c 2.48, CHCl₃). IR (CHCl₃)/cm⁻¹: 3410, 2986, 2934, 2861, 1648, 1455, 1380, 1247, 1214, 1164, 1124, 1061 (s), 986, 896 (m), 865, 827, 801, 752 (m), 697, 666 and 503. MS-EI: 774 (12%, M⁺*), 759 (11, [M–CH₃]⁺), 699 (8), 687 (22), 674 (100), 605 (44), 505 (12), 447 (6), 366 (8), 252 (12), 178 (7) and 152 (13). $^1$H: 5.98–5.89 (8H, m), 4.59 (4H, d, J 6.5), 4.26 (4H, br s), 4.13 (4H, dd, J 7.4, J 7.2), 3.39 (4H, t, J 9.1), 3.19 (4H, d 9.3), 2.82–2.70 (2H, m), 2.68–2.52 (2H, m), 1.52 (12H, s), 1.38 (12H, s) and 1.60–1.20 (6H, m, (CH₂)₃ overlapping with methyl singlets). $^{13}$C: 133.29 (CH), 125.12 (CH), 109.70 (C), 78.45 (CH), 71.96 (CH), 70.54 (CH), 58.58 (CH), 47.51 (CH₂), 29.16 (CH₂), 27.97 (CH₃), 25.38 (CH₃) and 24.08 (CH₂).

Properties: Yield 61% colourless foam. HRMS-EI: C₄₃H₆₆N₂O₁₂ requires 802.4616; Found 802.4613. $[\alpha]_D^{18}$+ 71.2° (c 1.81, CHCl₃). IR (CHCl₃)/cm⁻¹: 3411, 2985, 2931, 2857, 1646, 1456, 1380, 1247, 1215, 1164, 1124, 1061 (s), 988, 895 (m), 866, 828, 752 (m) and 697. MS-EI: 802 (14%, M⁺*), 787 (9, [M–CH₃]⁺), 727 (6), 715 (18), 702 (100), 633 (32), 534 (10), 366 (8) and 301 (8). $^1$H: 5.98–5.89 (8H, m), 4.59 (4H, d, J 6.6), 4.24 (4H, br s), 4.13 (4H, d, J 8.2, J 7.2), 3.39 (4H, dd, J 9.2, J 9.1), 3.19 (4H, d, J 9.5), 2.80–2.68 (2H, m), 2.64–2.50 (2H, m), 1.52 (12H, s), 1.38 (12H, s), 1.60–1.20 [10H, m, (CH₂)₅ overlapping with methyl singlets]. $^{13}$C: 133.41 (CH), 125.10 (CH), 109.75 (C), 78.48 (CH), 71.98 (CH), 70.63 (CH), 58.64 (CH), 47.42 (CH₂), 29.05 (CH₂), 28.99 (CH₂), 28.04 (CH₃), 26.04 (CH₂) and 25.49 (CH₃).

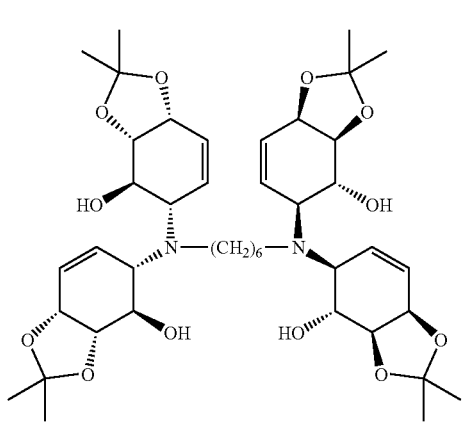

21b

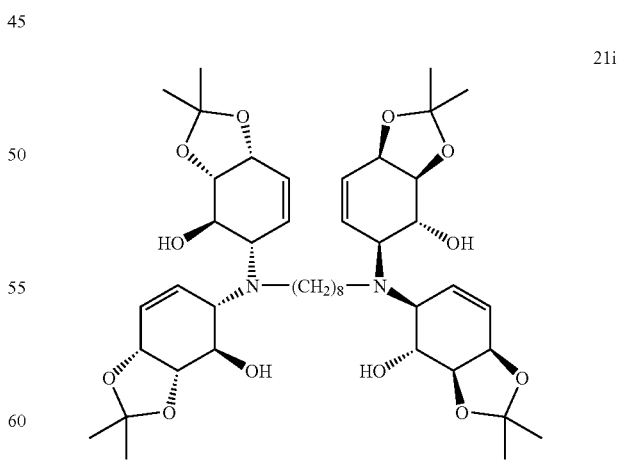

21i

Properties: Yield 100% colourless gum/foam. HRMS-EI: C₄₂H₆₄N₂O₁₂ requires 788.4459; Found 788.4464. $[\alpha]_D^{18}$+ 59.7° (c 1.89, CHCl₃). IR (CHCl₃)/cm⁻¹: 3399, 2985, 2933, 1646, 1456, 1379, 1246, 1214 (s), 1163, 1122, 1060 (s), 987, Properties: Yield 90% colourless foam. HRMS-EI: C₄₄H₆₈N₂O₁₂ requires 816.4772; Found 816.4761. $[\alpha]_D^{18}$+ 69.5° (c 4.50, CHCl₃). IR (CHCl₃)/cm⁻¹: 3413, 2986, 2933, 2856, 1549, 1456, 1380, 1247, 1215, 1164, 1123, 1060 (s), 993, 895 (m), 865, 828, 753 (m), 697 and 666. MS-EI: 816

(13%, M+*), 801 (7, [M–CH3]+), 729 (15), 716 (100), 647 (34), 547 (31), 489 (10), 366 (20) and 308 (40). ¹H: 5.96 (4H, d, J 10.8), 5.91 (4H, d, J 10.8), 4.60 (4H, d, J 6.5), 4.39 (4H, br s), 4.13 (4H, dd, J 7.6, J 7.4), 3.40 (4H, dd, J 9.1, J 9.0), 3.19 (4H, d, J 9.1), 2.80–2.66 (2H, m), 2.66–2.52 (2H, m), 1.52 (12H, s), 1.38 (12H, s) and 1.60–1.20 (12H, m, (CH2)6 overlapping with methyl singlets). ¹³C: 133.34, 124.82, 109.51, 78.33, 71.78, 70.31, 58.54, 47.48, 29.14, 28.99, 27.80 (CH3), 26.36, 25.22 (CH3).

(13), 744 (95), 675 (40), 366 (9) and 322 (10). ¹H: 5.99–5.88 (8H, m), 4.60 (4H, d, J 6.2), 4.12 (4H, dd, J 9.2, J 6.2), 4.02 (4H, br s), 3.40 (4H, dd, J 9.3, J 8.9), 3.20 (4H, d, J 9.3), 2.78–2.67 (2H, m), 2.63–2.50 (2H, m), 1.53 (12H, s), 1.39 (12H, s), 1.55–1.15 (16H), m, overlapping with methyl singlets). ¹³C: 133.62 (CH), 125.17 (CH), 109.90 (C), 78.62 (CH), 72.10 (CH), 70.75 (CH), 58.85 (CH), 47.82 (CH2), 29.35 (CH2), 29.16 (CH2), 29.05 (CH2), 28.11 (CH3), 26.63 (CH2) and 25.56 (CH3).

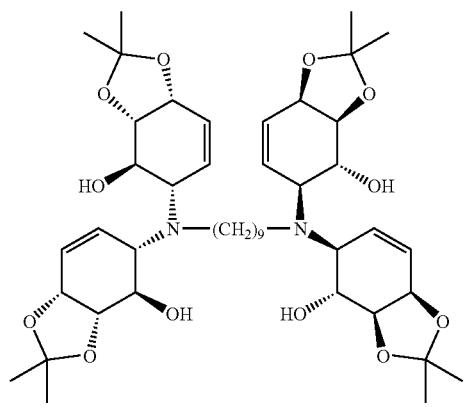

21j

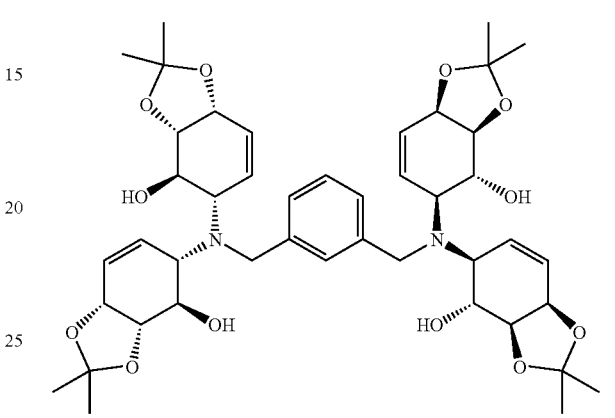

21d

Properties: Yield 100% mp 74–76° C. (white solid). HRMS-EI: C45H70N2O12 requires 830.4929; Found 830.4925. [α]D¹⁸+61.6° (c 3.55, CHCl3). IR (CHCl3)/cm⁻¹: 3411, 2985, 2928, 2855, 1456, 1379, 1246, 1214, 1164, 1061 (s), 988, 894, 865 and 752 (m). MS-EI: 830 (13%, M+*), 815 (8, [M–CH3]+), 743 (14), 730 (100), 661 (34), 561 (27), 366 (25) and 315 (49). ¹H: 5.94 (8H, br s), 4.60 (4H, d, J 4.5), 4.11 (4H, dd, J 7.6, J 7.4), 3.98 (4H, br s), 3.40 (4H, dd, J 8.8, J 8.4), 3.19 (4H, d, J 8.2), 2.82–2.67 (2H, m), 2.66–2.50 (2H, m), 1.53 (12H, s), 1.39 (12H, s), 1.70–1.10 [14H, m, (CH2)7 overlapping with methyl singlets]. ¹³C: 133.38, 124.87, 109.60, 78.43, 71.86, 70.40, 58.53, 47.58, 29.20 (2×CH2 overlapping), 29.05 (CH2), 27.89 (CH3), 26.62 (CH2) and 25.30 (CH3).

Properties: Yield 83% mp 130–132° C. (off-white solid). HRMS-EI: C44H60N2O12 requires 808.4146; Found 808.4141. [α]D¹⁸+43.3° (c 3.84, CHCl3). IR (CHCl3)/cm⁻¹: 3417, 2986, 2933, 1607, 1454, 1379, 1247, 1214, 1164, 1060 (s), 975, 895, 863 and 753. MS-EI: 808 (11%, M+*), 793 (12, [M–CH3]+), 721 (50), 708 (80), 639 (22), 539 (14), 481 (14), 457 (41), 399 (12), 355 (22), 186 (21) and 105 (100). ¹H: 7.46 (1H, s), 7.27–7.19 (3H, m), 6.08 (4H, d, J 10.0), 5.96 (4H, ddd, J 10.0, J 3.1, J 2.5), 4.59 (4H, br m), 4.16 (4H, br s), 4.05 (4H, dd, J 8.4, J 7.0), 3.93 (2H, d, J 14.4), 3.81 (2H, d, J 14.4), 3.51 (4H, dd, J 9.1, J 8.9), 3.24 (4H, d, J 9.1), 1.50 (12H, s) and 1.36 (12H, s). ¹³C: 139.24 (C), 132.31 (CH), 129.06 (CH), 128.12 (CH), 127.47 (CH), 125.44 (CH), 109.62 (C), 78.31 (CH), 71.92 (CH), 70.53 (CH), 58.13 (CH), 51.48 (CH2), 27.87 (CH3) and 25.29 (CH3).

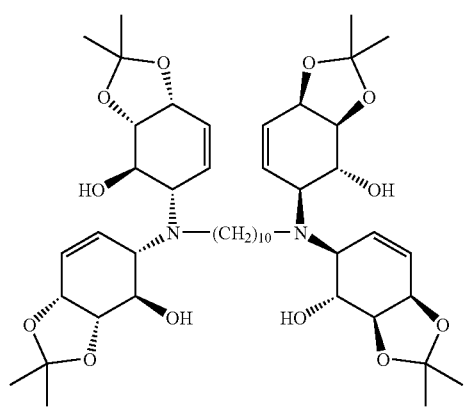

21c

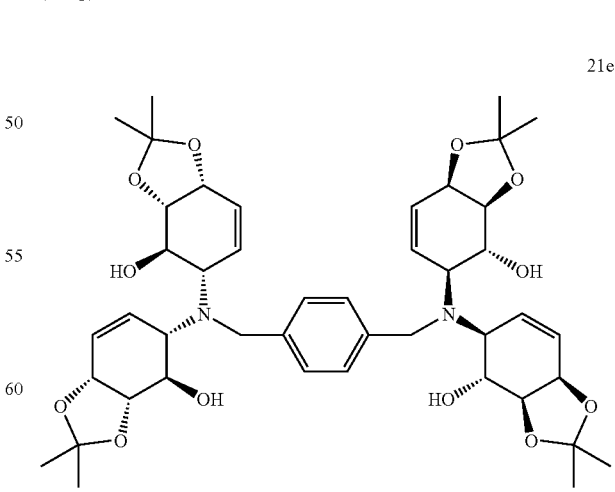

21e

Properties: Yield 55% colourless gum. HRMS-EI: C46H72N2O12 requires 844.5085; Found 844.5081. [α]D¹⁸+50.2° (c 0.42, CHCl3). IR (CHCl3)/cm⁻¹: 3401, 2984, 2928, 2854, 1455, 1380, 1245, 1214, 1163, 1061 (s), 895, 866, and 752. MS-EI: 844 (11%, M+*), 829 (10, [M–CH3]+), 757

Properties: Yield 100% mp 133–136° C. (colourless crystals). HRMS-EI: C44H60N2O12 requires 808.4146; Found 808.4138. $[\alpha]_D^{18}$+37.8° (c 1.69, CHCl$_3$). IR (CHCl$_3$)/cm$^{-1}$: 3417, 2986, 2933, 1379, 1247, 1215, 1164, 1060 (s), 970, 896, 863 and 751. MS-ES: 831 ([M+Na]$^+$), 809 ([M+H]$^+$); MS-FAB: 831 ([M+Na]$^+$), 809 ([M+H]$^+$). MS-EI: 708 (6%), 389 (21), 270 (42), 219 (70) and 179 (100). $^1$H: 7.32 (4H, m), 6.07 (4H, d, J 10.0), 5.96 (4H, dd, J 10.0, J 2.2), 4.58 (4H, br m), 4.28 (4H, br s), 4.08 (4H, dd, J 6.6, J 6.4), 3.92 (2H, d, J 13.6), 3.84 (2H, d, J 13.6), 3.53 (4H, dd, J 9.1, J 7.3), 3.27 (4H, d, J 9.1), 1.50 (12H, s) and 1.37 (12H, s). $^{13}$C: 138.30 (C), 132.66 (CH), 128.53 (CH), 125.59 (CH), 109.98 (C), 78.48 (CH), 72.12 (CH), 70.87 (CH), 58.35 (CH), 51.48 (CH$_2$), 28.14 (CH$_3$) and 25.51 (CH$_3$).

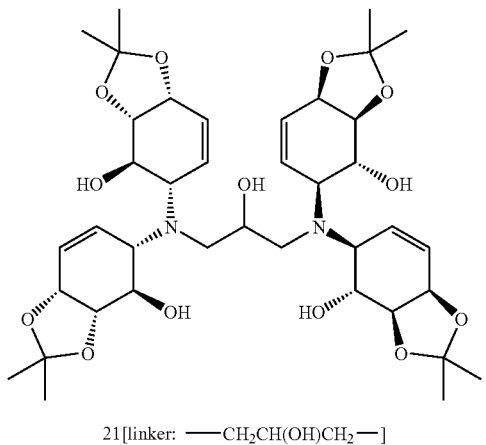

21 [linker: —CH$_2$CH(OH)CH$_2$—]

Properties: Yield 77% mp 138–140° C. (off-white solid). HRMS-EI: M–CH$_3$ (C$_{38}$H$_{55}$N$_2$O$_{13}$) requires 747.3704; Found 747.3716. $[\alpha]_D^{18}$+27.2° (c 1.05, CHCl$_3$). IR (CHCl$^3$)/cm$^{31}$ $^1$: 3391, 2985, 2934, 1647, 1455, 1380, 1244, 1216, 1163, 1061 (s), 985, 896, 863 and 752. MS-EI: 747 {7%, [M–CH$_3$]$^+$}, 664 (5), 575 (12), 398 (42), 368 (100) and 219 (36). $^1$H. NMR: 5.92–5.81 (8H, m), 4.63–2.16 (26H, m), 1.53 (12H, s) and 1.39 (12H, s).

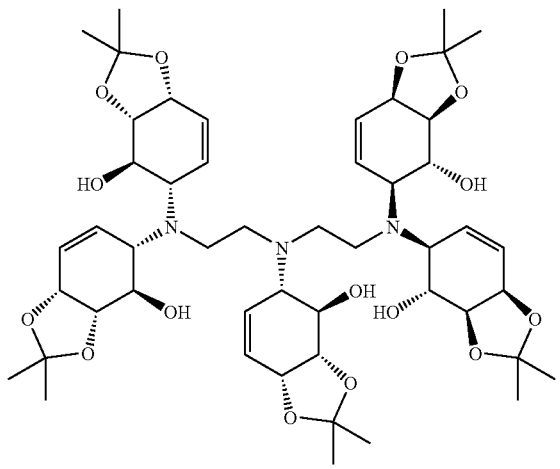

24

Properties: Yield 58% white foam. HRMS-EI: M–CH$_3$ (C$_{48}$H$_{70}$N$_3$O$_{15}$) requires 928.4807; Found 928.4802. $[\alpha]_D^{18}$+33.4° (c 0.89, CHCl$_3$). IR (CHCl$_3$)/cm$^{-1}$: 3401, 2984, 2932, 1642, 1456, 1380, 1246, 1214, 1163, 1062 (s), 985, 895, 865 and 751. MS-EI: 929 (2%, [M–CH$_3$]$^+$), 774 (19), 577 (100), 533 (13), 409 (13), 380 (28) and 366 (93). $^1$H: 5.92 (10H, s), 4.60–4.57 (5H, m), 4.25–3.82 (9H, m, contains 4×OH), 3.50–3.36 (6H, m, contains 1×OH), 3.30–3.17 (5H, m), 2.88–2.78 (4H, m), 2.78–2.62 (2H, m), 2.62–2.48 (2H, m), 1.52 (15H, s) and 1.37 (15H, s). $^{13}$C: 133.13, 130.54, 125.74 (2×C), 109.90 (2×C), 78.81, 78.39, 72.07 (2×C), 70.77, 70.09, 62.09, 59.41, 51.24, 46.92, 28.20, 28.05, 25.60 and 25.46.

EXAMPLE 11

Pd(0)-catalysed bis-Amide Insertion

A mixture of alkenyl-iodide 28 (1 eq), the appropriate 1,ω-diamine (0.5 eq), tributylamine (1.02 eq) and the appropriate Pd[0]-catalyst (3 mol %) in DME (0.2 M) was purged with CO for 5 min, then stirred under a CO atmosphere (balloon) at 100° C. for 4 h while being monitored by TLC (n-hexane-EtOAc 1:2 elution). The reaction mixture was then air-dried, and the residue purified by column chromatography (silica, n-hexane-EtOAc 1:2) or PTLC (n-hexane-EtOAc 1:2) to provide tetrameric product 30.

Details of specific syntheses follow.

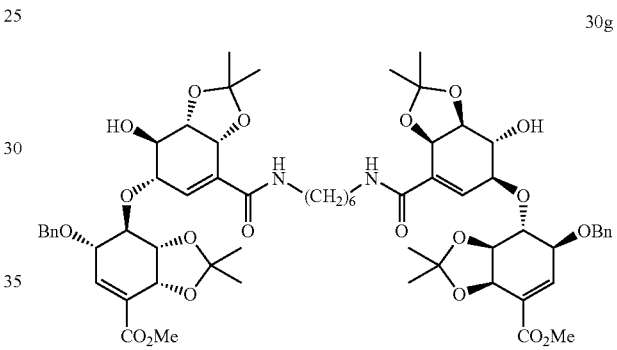

30g

Properties: Yield 8% mp 105–107° C. (pale-yellow solid). HRMS-FAB: M+H (C$_{62}$H$_{81}$N$_2$O$_{20}$) requires 1173.5382; Found 1173.5395. MS-FAB: 1195.5 (M+Na$^+$), 1173.5 (M+H$^+$). $^1$H: 7.48–7.29 (10H, m), 7.02 (2H, d, J 1.5), 7.00 (2H, s), 6.66 (2H, t, J 5.7, CONH—), 4.99 (2H, d, J 6.6), 4.77 (2H, d, J 7.0), 4.74 (4H, s), 4.62 (2H, s), 4.27–4.03 (8H, m), 3.81 (6H, s), 3.68 (2H, d, J 9.1) and 3.65 (2H, d, J 8.8) [or 3.70–3.63 (4H, triplet-like)], 3.32 (4H, dt, J 5.7, J 7.1, CONH—CH$_2$—), 1.55 (12H, s), 1.44 (6H, s), 1.43 (6H, s), 1.64–1.32 (8H, m, overlapping with CH$_3$ singlets at δ 1.55, 1.44 and 1.43).

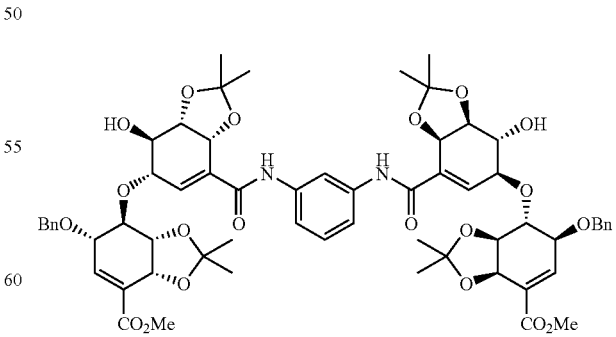

30 [linker: -m—C$_6$H$_4$—]

Properties: Yield 37% mp 242–244° C. (off-white solid). $[\alpha]_D^{18}$+118.4° (c 0.74, CHCl$_3$). IR (CHCl$_3$)/cm$^{-1}$: 3438, 2988, 2935, 1724 (s), 1679, 1646, 1608, 1542, 1486, 1437, 1372, 1320, 1253, 1217, 1163, 1110, 1069, 992, 866 and 753. MS-ES: 1187 (M+Na$^+$), 1165 (M+H$^+$). $^1$H: 8.56 (2H, s), 7.91 (1H, s), 7.47–7.24 (13H, m), 7.08 (2H, s), 7.05 (2H, s), 5.01 (2H, d, J 6.4), 4.90 (2H, d, J 6.9), 4.76 (2H, d, J 11.1), 4.71 (2H, d, J 11.1), 4,67 (2H, s), 4.28–4.22 (4H, m), 4.08 (4H, d, 8.8) [or 4.10 (2H, s), and 4.07 (2H, s)], 3.82 (6H, s), 3.74–3.65 (4H, m), 1.61 (6H, s), 1.56 (6H, s), 1.49 (6H, s) and 1.45 (6H, s). $^{13}$C: 165.07 (C), 163.07 (C), 140.75 (CH), 140.47 (CH), 138.45 (C), 136.51 (C), 129.74 (C), 129.47 (CH), 128.83 (CH), 128.66 (CH), 128.27 (CH), 127.20 (C), 116.21 (CH), 111.95 (CH), 111.48 (C), 111.40 (C), 84.02 (CH), 82.94 (CH), 77.78 (CH), 77.33 (CH), 77.06 (CH), 73.99 (CH), 72.46 (CH$_2$), 71.40 (CH), 71.23 (CH), 52.33 (CH$_3$), 27.99(CH$_3$), 27.66 (CH$_3$), 25.89 (CH$_3$) and 25.66 (CH$_3$).

resulting crude samples of polyols 2 used directly for the sulfation reaction described below.

EXAMPLE 14

Deprotection of Cyclitol Acetonides

A solution of compound 21 (0.4 mmol) in THF (4 mL) and 1 M aq. HCl (4 mL) was stirred at 18° C. for 16 h. After neutralisation with 1 M aq. NaOH, the reaction mixture was evaporated to dryness. The ensuing polyol 1 could be partially separated from the co-produced NaCl by extraction with MeOH, but in most cases, the crude material was freezed-dried overnight and used directly in the subsequent sulfation reaction.

Details of specific syntheses follow.

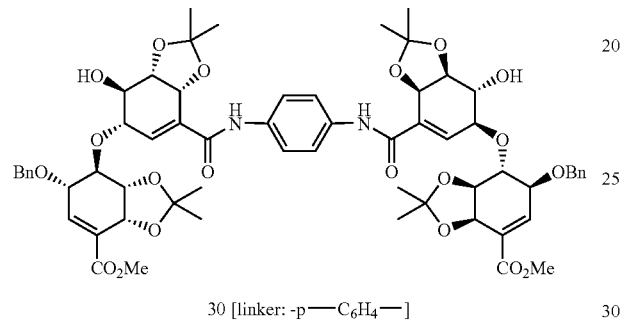

30 [linker: -p—C$_6$H$_4$—]

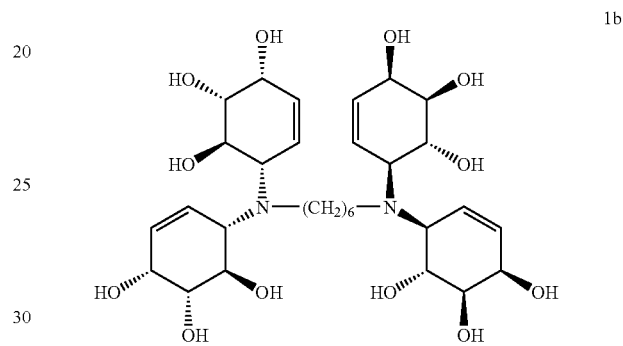

Properties: Yield 46% mp 265–266° C. (off-white solid, EtOAc). HRMS-FAB: M+H (C$_{62}$H$_{73}$N$_2$O$_{20}$) requires 1165.4757; Found 1165.4737. [α]$_D$$^{18}$+166.4° (c 1.00, CHCl$_3$). IR (CHCl$_3$)/cm$^{-1}$: 3453, 3364, 2988, 2925, 1725 (s), 1679, 1642, 1609, 1559, 1516, 1437, 1405, 1372, 1312, 1254 (s), 1217, 1166, 1112, 1069 (s), 1025, 991, 866 and 754. MS-FAB: 1187.6 (M+Na$^+$), 1165.4 (M+H$^+$). $^1$H: 8.56 (2H, s), 7.56 (4H, s), 7.48–7.29 (10H, m), 7.09 (2H, s), 7.05 (2H, d, J 1,1), 5.01 (2H, d, J 6.0), 4.91 (2H, d, J 7.6), 4.80–4.60 (6H, m), 4.28–4.23 (4H, m), 4.09 (4H, d, J 8.7) [or 4.11 (2H, s) and 4.08 (2H, s)], 3.82 (6H, s), 3.75–3.66 (4H, m), 1.62 (6H, s), 1.57 (6H, s), 1.50 (6H, s) and 1.46 (6H, s). $^{13}$C: 165.05 (C), 162.78 (C), 140.80 (CH), 140.38 (CH), 136.49 (C), 134.27 (C), 129.62 (C), 128.82 (CH), 128.65 (CH), 128.28 (CH), 127.11 (C), 120.60 (CH), 111.45 (C), 111.39 (C), 84.00 (CH), 82.94 (CH), 77.80 (CH), 77.31 (CH), 77.03 (CH), 73.99 (CH), 72.49 (CH$_2$), 71.40 (CH), 71.21 (CH), 52.36 (CH$_2$), 27.99 (CH$_3$), 27.66 (CH$_3$), 25.90 (CH$_3$) and 25.67 (CH$_3$).

EXAMPLE 12

OsO$_4$-catalysed Dihydroxylation of Tetra-enes 21

To a magnetically stirred solution of the appropriate deiodinated tetramer (0.1 mmol) in acetone (0.6 mL) and water (0.6 mL) was added N-methylmorpholine-N-oxide (NMMNO) (0.6 mmol) and catalytic amount of osmium tetroxide solution in t-BuOH (2.5% w/w). The mixture was stirred at 60° C. for 7 h then another portion of NMMNO (0.6 mmol) was added. The mixture was stirred for another 24 h while being monitored by TLC. The mixture was cooled, treated with 10% Na$_2$S$_2$O$_5$ aqueous solution (1.5 mL), stirred for 1 h at r.t. then treated with conc. HCl (0.5 mL), stirred overnight, neutralised with 1 M NaOH and evaporated to dryness. The residue was freeze-dried and the Properties: Yield 100% white solid. $^1$H (D$_2$O, internal reference acetone CH$_3$ at δ 2.22): 6.02 (4H, d, 10.0), 5.94 (4H, br s), 4.26 (4H, br s), 3.66 (8H, s), 3.37 (4H, s), 2.81 (2H, br s), 2.63 (2H, br s), 1.50 (4H, br m) and 1.33 (4H, br m). $^{13}$C (D$_2$O, internal reference acetone CH$_3$ at δ 30.89): 131.56, 128.50, 71.85, 68.79, 66.79, 62.73, 47.69, 28.58, 23.86.

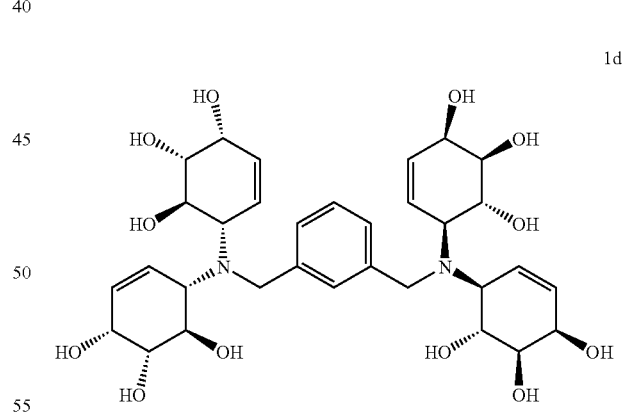

Properties: Yield 100% mp>300° C. (pale-yellow solid). [α]$_D$$^{18}$+40.0° (c 2.66, H$_2$O). IR (KBr)/cm$^{-1}$: 3391, 3027, 2906, 1642, 1393, 1259, 1180, 1156, 1089, 1037, 984, 869 and 802. MS-ES: 671 ([M+Na]$^+$). $^1$H (D$_2$O-acetone-d$_6$, 8:1, v/v with CD$_3$COCHD$_2$ at δ 2.22): 7.51 (1H, s), 7.34–7.24 (3H, m), 6.12 (4H, d, J 10.2), 5.95 (4H, dd, J 10.2, J 5.0), 4.24 (4H, dd, J 5.0, J 3.9), 3.86 (4H, s), 3.75 (4H, dd, J 10.9, J 8.2), 3.56 (4H, dd, J 10.7, J 3.9) and 3.25 (4H, d, J 8.2). $^{13}$C (D$_2$O-acetone-d$_6$, 8:1, v/v with CD$_3$COCHD$_2$ at δ 215.94): 140.96, 131.68, 128.36, 129.57, 128.88, 72.02, 69.30, 67.02, 61.64 and 51.22.

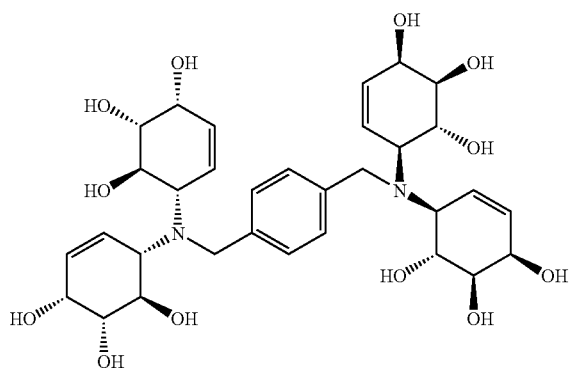

1e

Properties: Yield 100% white solid. $[\alpha]_D^{18}$+25.8° (c 0.64, H$_2$O). $^1$H (D$_2$O, internal reference acetone CH$_3$ at δ 2.22): 7.36 (4H, s), 6.12 (4H, d, J 10.3), 5.93 (4H, br s), 4.23 (4H, s), 3.83 (4H, s), 3.72 (4H, t, J 8.8), 3.55 (4H, d, J 10.4) and 3.25 (4H, d, J 7.8). $^{13}$C (D$_2$O, internal reference acetone CH$_3$ at δ 30.89): 139.54, 131.85, 129.63, 128.13, 71.98, 69.23, 67.01, 61.88 and 51.08.

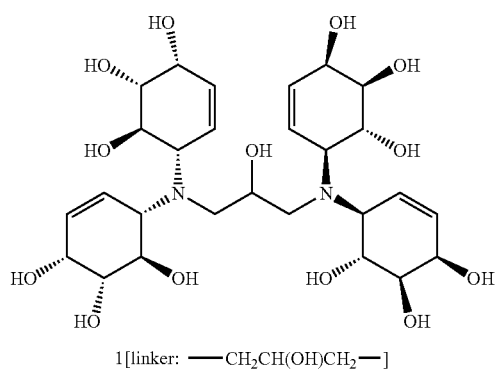

1 [linker: —CH$_2$CH(OH)CH$_2$—]

Properties: 100% white solid. MS-ES: 625 ([M+Na]$^+$).

EXAMPLE 14

Sulfation of Linked-Cyclitol Compounds

The appropriate polyol (0.1 mmol) was dissolved in dry DMF (2.4 mL) and treated with sulfur trioxide-pyridine complex (2 eq per hydroxy group). The ensuing mixture was stirred at 60° C. for 7 days, cooled to 0° C., basified to pH=9, with 1 M NaOH. EtOH (50 mL) was added and the mixture was stirred at room temperature for 30 min and the solid was collected by filtration and rinsed with EtOH (3×1 mL) and air-dried. This crude product was loaded on a G-25 column (ϕ1×52 cm, water as eluent, flow rate 7.7 mL/min), the organic fractions (spotted on TLC plate and charcoalised by using 10% H$_2$SO$_4$ in EtOH) were combined and separated again by G-25 column. The sodium salts obtained after two G-25 column separations were loaded on P-2 column (ϕ1× 52 cm, eluted with 0.1 M NH$_4$HCO$_3$, flow rate 1 ml/min). The organic fraction was combined and concentrated, freeze-dried (small amount of water was added every couple of hours in order to facilitate removal of ammonium bicarbonate salt). The resulting colorless or greenish flakes were loaded on a Na$^+$—NH$_4$$^+$ column, eluted with water, the organic fraction was concentrated and freeze-dried to give pure sodium salt of the product sulfate.

Details of specific syntheses follow.

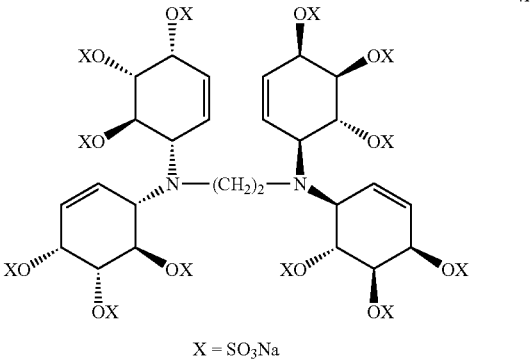

4f

X = SO$_3$Na

Properties: MS-ES: 12×SO$_3$Na: 921 (M+Na$^+$+Na$^+$), 910 (M+Na$^+$+H$^+$). 11×SO$_3$Na: 870 (M+Na$^+$+Na$^+$).

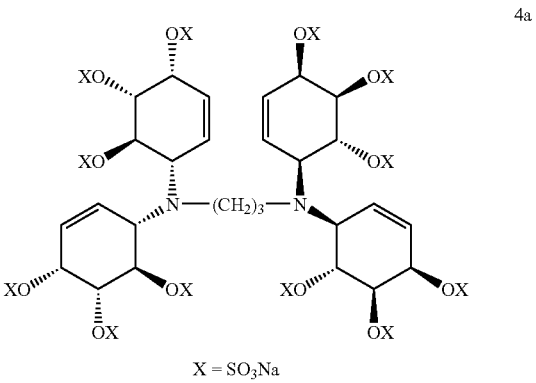

4a

X = SO$_3$Na

Properties: MS-ES: 12×SO$_3$Na: 928 (M+Na$^+$+Na$^+$), 917 (M+Na$^+$+H$^+$).

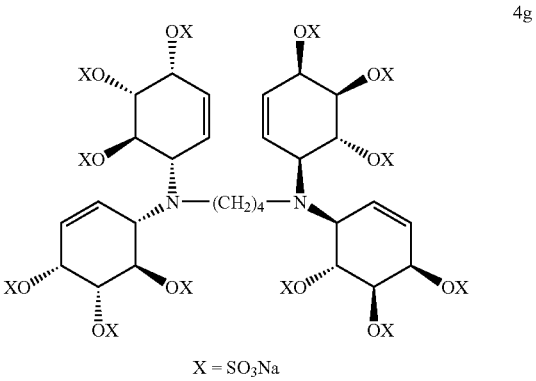

4g

X = SO$_3$Na

Properties: MS-ES: 12×SO$_3$Na: 935 (M+Na$^+$+Na$^+$), 924 (M+Na$^+$+H$^+$).

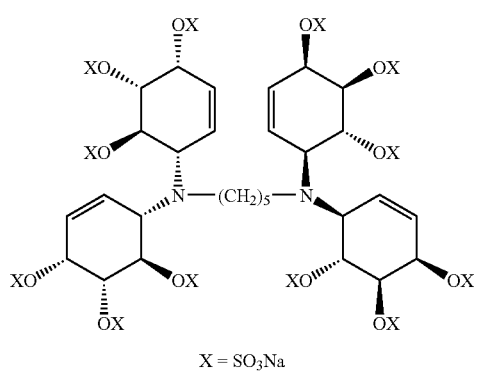

4k

X = SO₃Na

Properties: MS-ES: 12×SO₃Na: 942 (M+Na⁺+Na⁺), 931 (M+Na⁺+H⁺).

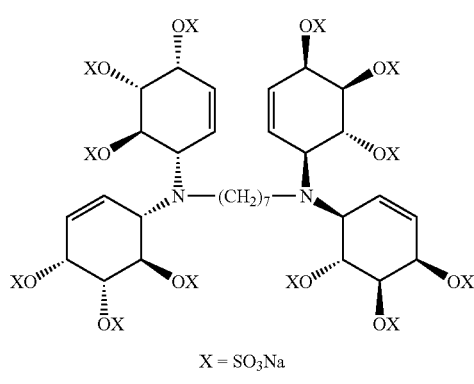

4h

X = SO₃Na

Properties: MS-ES: 12×SO₃Na: 956 (M+Na⁺+Na⁺), 945 (M+Na⁺+H), 934 (M+H⁺+H⁺).

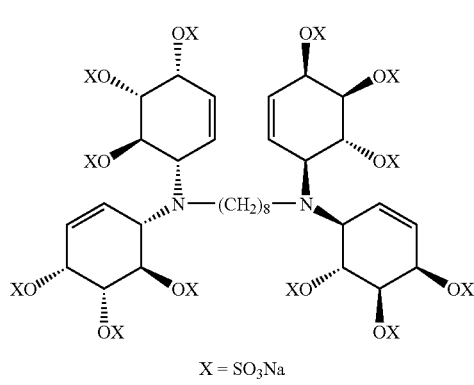

4i

X = SO₃Na

Properties: MS-ES: 12×SO₃Na: 963 (M+Na⁺+Na⁺), 952 (M+Na⁺+H⁺), 941 (M+H⁺+H⁺); 11×SO₃Na: 912 (M+Na⁺+Na⁺), 901 (M+Na⁺+H⁺).

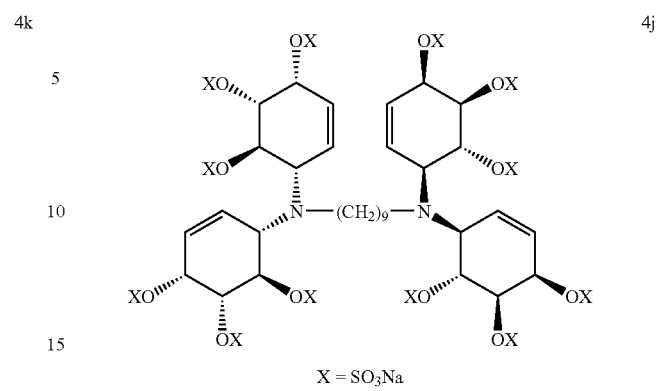

4j

X = SO₃Na

Properties: MS-ES: 12×SO₃Na: 970 (M+Na⁺+Na⁺), 959 (M+Na⁺+H⁺), 948 (M+H⁺+H⁺). ¹H (D₂O, acetone δ 2.22): 25° C., very broad signals merging into baseline. ¹H (D₂O, DMSO δ 2.49): 25° C., very broad signals merging into baseline. 90° C.: all signals clear but still broad, 6.04–5.95 (8H, br m), 4.96 (4H, br s), 4.84 (4H, br s), 4.56 (4H, br s), 4.23 (4H, br s), 3.04 (2H, br s), 2.88 (2H, br s), 1.51 (4H, br s), 1.08 (10H, br s). ¹³C (D₂O, DMSO δ 2.49): at 90° C., still very complicated due to the presence of various rotamers.

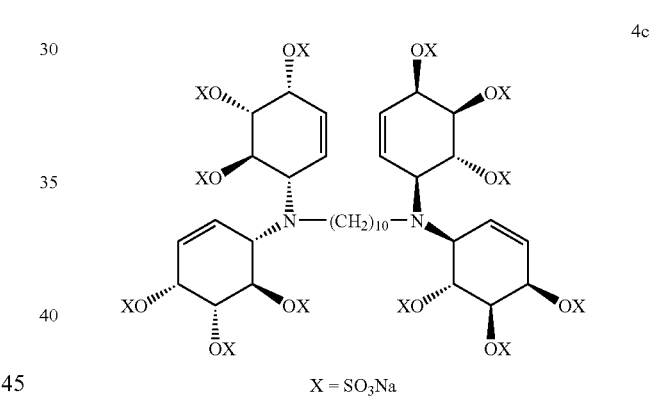

4c

X = SO₃Na

Properties: MS-ES: 12×SO₃Na: 959 (M+Na⁺+Na⁺); 11×SO₃Na: 908 (M+Na⁺+Na⁺).

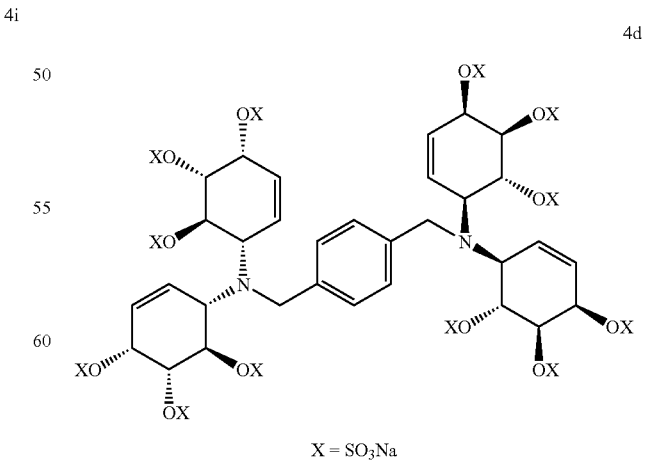

4d

X = SO₃Na

Properties: MS-ES: 12×SO₃Na: 959 (M+Na⁺+Na⁺), 948 (M+Na⁺+H⁺); 11×SO₃Na: 908 (M+Na⁺+Na⁺).

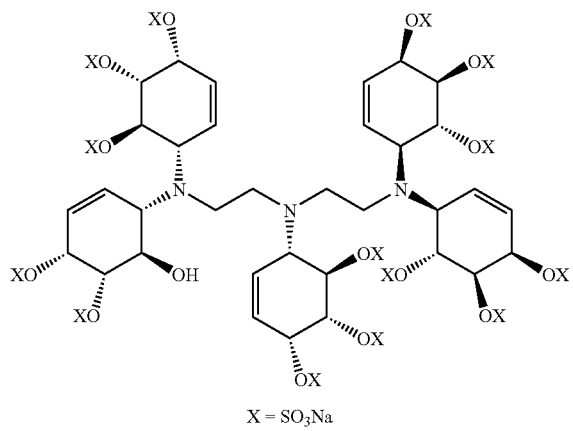

X = SO₃Na

Polysulfated Derivative of Compound 25

Properties: MS-ES: 15×SO₃Na: 1159 (M+Na$^+$+Na$^+$), 1148 M+Na$^+$+H$^+$).

B. Biological Activities of Linked Cyclitol Compounds

EXAMPLE 15

Effect of Linked-Cyclitol Compounds on Cathepsin G and Elastase Activity

Human neutrophil elastase and cathepsin G are serine proteases released from the primary granules following the activation of polymorphonuclear neutrophils in sites of acute inflammation. Both enzymes have been implicated in tissue destruction associated with a number of inflammatory diseases including adult respiratory distress syndrome, cystic fibrosis, emphysema and arthritis. Several anionic polymers including heparin have been shown to inhibit both enzymes. However, apart from suramin (a biphenyl disulfonic acid copolymer) and low molecular sized heparin fragments, no comprehensive study of the ability of small sized sulfated compounds to inhibit either enzyme has been reported.

A range of synthetic polysulfated linked cyclitol compounds were examined for their ability to inhibit human leukocyte cathepsin G activity. The conventional enzyme assays were found to be unsuitable for the large scale screening of potential inhibitors. A new assay procedure was therefore developed.

Methods

Cathepsin G activity was determined using a 96 well assay format in PVC microtitre U-bottom plates with activity determination by a fluorescence plate reader. Briefly, within a total incubation volume of 40 µl, human leukocyte Cathepsin G (100 ng protein) was added to a mixture of inhibitor and the fluorogenic substrate MeOSuc-ala-ala-pro-phe-AMAC in 50 mM-NaOAc buffer, pH 6.6 containing 50 mM NaCl and 0.1% (v/v) Brij 35. The mixture was incubated at 37° C. for 60 min, the reaction stopped by the addition of 40 µl of 250 mM acetic acid and the fluorescence determined with excitation at 360 nm and emitted light measured at 460 nm.

The results of the cathepsin G assays are presented below in Table 2. In this table, the linked cyclitol compound identifications are the same as those given in Section A above where the structures of the compounds are also given. With regard to the purity rating, a greater number of asterisks signifies a greater degree of purity with five asterisks signifying an essentially pure compound. The cathepsin G inhibition data are the concentrations of compounds required to inhibit the enzyme by 50%.

Results

Heparin, PI-88 and most of the sulfated linked cyclitol compounds inhibited Cathepsin G activity with IC$_{50}$ values less than 0.5 µg/mL (see Table 2). Heparin and PI-88 inhibited cathepsin G activity with IC$_{50}$ values of 0.32 and 0.15 µg/mL respectively. The most potent sulfated linked cyclitol was 4j [Linker: —(CH$_2$)$_9$—] with an IC$_{50}$ of 0.15 µg/mL. While the more highly sulfated of the linked cyclitols (hydroxylated tetra-enes) series were better heparanase inhibitors than the tetra-enes (see below), they were observed to be slightly less potent cathepsin G inhibitors (Table 2).

TABLE 2

Cathepsin G Inhibition Results

| Compound | Purity | Amount for 50% inhibition (µg/ml) |
|---|---|---|
| PI-88 | ***** | 0.32 |
| 4f | ***** | 0.29 |
| 4a | ***** | 0.25 |
| 4g | ***** | 0.20 |
| 4k | ***** | 0.21 |
| 4b | ***** | 0.22 |
| 4h | ***** | 0.51 |
| 4i | ***** | 0.22 |
| 4j | ***** | 0.15 |
| 4c | ***** | 0.26 |
| 4d | ***** | 0.43 |
| 4e | ***** | 0.30 |
| 4l | ** | 0.48 |
| Polysulfated derivative of compound 25 | ***** | 0.24 |
| 5l | ** | 0.53 |
| 5b | * | 0.72 |
| 5c | ** | 0.48 |
| 5d | ** | 0.53 |
| Sucrose octasulfate | ***** | 4.30 |
| Heparin (lung) | ***** | 0.15 |

EXAMPLE 16

Effect of Linked-Cyclitol Compounds on Heparanase Activity

Heparan sulphate (HS) is an important component of the extracellular matrix (ECM) and the vasculature basement membrane (BM) which functions as a barrier to the migration and vascular extravasation of metastising tumour cells and leukocytes. Cleavage of the HS chains by heparanase activity which is upregulated in invading cells assists in the disassembly of the ECM and facilitates cell migration. The normal physiological function of heparanase occurs during wound repair, angiogenesis and inflammation, permitting BM degradation and cellular invasion into the ECM. However, during the progression of autoimmune and other inflammatory diseases, excessive ECM invasion of leukocytes occurs. During tumour growth, heparanase activity released by the establishing tumour foci can release ECM-bound growth factors, sustaining further tumour growth and stimulating neoangiogenesis. Using a novel assay (see Freeman, C., and Parish, C. R. [1997], "A rapid quantitative assay for the detection of mammalian heparanase activity." *Biochemical Journal* 325: 229–37), heparanase was purified and cloned and it was demonstrated that the same enzyme is expressed in platelets, T lymphocytes and metastatic tumour cells (see Hulett, M. D., Freeman, C., Hamdorf, B. J., Baker, R. T., Harris, M. J., and Parish, C. R. [1999], "Cloning of mammalian heparanase, an important enzyme in tumor invasion and metastasis." *Nat Med* 5:7 803–9). Exhaustive studies have so far revealed the presence of only one enzyme, consistant with the view that heparanase is the dominant endoglucuronidase in mammalian tissues. Heparanase therefore represents an excellent target for the development of drugs to inhibit tumour metastasis, angiogenesis and inflammation.

The same compounds examined in the previous example were tested for their ability to inhibit human platelet heparanase activity.

Methods

Briefly, to an incubation mixture of 40 mL containing $^3$H-radiolabelled porcine mucosal HS (2 mg), 50 mM-sodium acetate buffer, pH 5.0, 100 mg/mL bovine serum albumin and the inhibitor to be tested, was added 10 ng of purified human platelet heparanase and the mixture incubated for 30 min. The reaction was terminated by freezing the assay tubes. The substrate was separated from the cleavage products on minicolumns of sepharose-bound histidine-rich glycoprotein (Freeman, C., and Parish, C. R. [1997], supra).

The results of the heparanase assays are presented below in Table 3. Inhibitory activity is based on a comparison with heparin with 100% inhibition at 30 µg/ml. In Table 3, the same compound identifications as given in Table 2 have been used. The compounds were also tested at the same purity as in Example 15.

Results

The data of Table 3 show that for cyclitols linked by alkyl diamines, N—$(CH_2)_n$—N, n=2–10, there is no clear relationship between the inhibition of heparanase activity and the length of the diamine linker, with all compounds being only moderate heparanase inhibitors. The addition of a sulphate moiety within the diamine linker (for example 4l [linker —$CH_2CH(OSO_3)NaCH_2$—]), did not enhance heparanase inhibition compared to the diamine 4a [linker —$(CH_2)_3$—]. Heparanase inhibition, however, was enhanced up to 3-fold by cyclitols linked by m- and p-benzyl diamines, N—$(CH_2)_2$-Bz-$(CH_2)_2$—N with the more extended p-substituted moiety of compound 4e being a more potent heparanase inhibitor. The most potent heparanase inhibitor in this series was the compound having the trisulphated cyclitol-substituted linker [—$(CH_2)_2$—N $(C_6H_6S_3O_{12})$—$(CH_2)_2$—]: see the result for "Polysulfated of compound 25".

Heparanase inhibition by sulfated oligosaccharides has been shown to be highly dependent upon the degree of sulphation of the compound being tested. In the expectation of generating more active compounds, more highly sulphated derivatives of the alkyl diamine linked cyclitols were produced from the tetra-enes of type 4 by osmium tetraoxide mediated dihydroxylation, which following hydrolysis to the corresponding polyols and subsequent sulphation, gave compounds of type 5. The cyclitols linked by alkyl diamines, N—$(CH_2)_6$—N, N—$CH_2CH(SO_3)CH_2$—N and N—$(CH_2)_2$-mBz-$(CH_2)_2$—N (compounds 5b, 5l and 5d respectively) were in each case more than 2-fold better heparanase inhibitors than the tetra-enes they were derived from. However, compound 5c [linker: —$(CH_2)_{10}$—] remained a poor heparanase inhibitor.

TABLE 3

Heparanase Inhibition Results

| Compound | Relative inhibition (%) | Inhibition (%) at 10 µg/ml | $EC_{50}$ (µg/ml) |
|---|---|---|---|
| PI-88 | 100 | 90 | 2.9 |
| 4f | 60 | 44 | 17 |
| 4a | 60 | 37 | 25 |
| 4g | 57 | 42 | 22 |
| 4k | 50 | 39 | 30 |
| 4b | 45 | | 40 |
| 4h | 48 | 33 | 32 |
| 4i | 53 | 39 | 26 |
| 4j | 73 | | 10 |
| 4c | 45 | | 42 |
| 4d | 75 | | 15 |
| 4e | 70 | | 9 |
| 4l | 48 | | 28 |
| Polysulfated derivative of compound 25 | 96 | 87 | 3.5 |
| 5l | 85 | | 12 |
| 5b | 74 | | 14 |
| 5c | 45 | | 50 |
| 5d | 100 | | 6 |
| Sucrose octasulfate | 0 | | >30 |
| Heparin (lung) | 100 | | 2.0 |

EXAMPLE 17

Effect of Linked-Cyclitol Compounds on the Binding of Effectors to Heparin and Heparan Sulfate The subject linked cyclitol compounds were tested for their ability to inhibit the binding of the growth factors bFGF, aFGF and VEGF, and the chemokine IL-8, to immobilised heparin and heparan sulfate.

Methods

Assays were performed using a Biacore™ 2000 optical biosensor obtained from Biacore AB, Uppsala, Sweden. The biosensor was operated in accordance with the manufacturer's instructions. Briefly, neutravidin was covalently coupled to the surface of CM5 chips of the biosensor and then either biotinylated heparin (1 µg/ml) or biotinylated heparan sulfate (5 µml) bound to the immobilised neutravidin. Mixtures of a test compound and a growth factor or other effector compound were preincubated for 2 to 5 minutes and the mixtures then added to individual biosensor cuvettes. Binding of growth factor or effector compound to the heparin or heparan sulfate was then monitored for approximately 5 minutes with the biosensor.

The results obtained are presented below in Table 4. For the testing of inhibition of bFGF, aFGF and VEGF binding, each potential inhibitor was tested at 0.034 µM with bFGF at the same concentration but aFGF and VEGF at 0.025 µM. The tabulated values are the $IC_{50}$ in µM or % inhibition of binding of the growth factor to the immobilised heparan sulfate (HS) or heparin.

The IL-8 data represent the % inhibition of binding of IL-8 at a concentration in assays of 0.068 µM to the immobilised HS or heparin with each potential inhibitor at 1.0 µM.

In Table 4, the same compound identifications as given in Table 2 have again been used. The compounds were also tested at the same purity as in Example 15.

Results

The data of Table 4 show that the length of the hydrocarbon spacer in the less sulfated compounds has a substantial effect on the ability of the compounds to block bFGF and aFGF binding to heparin and heparan sulfate. For maximum activity against bFGF a hydrocarbon spacer >—$(CH_2)_3$— is required whereas with aFGF the —$(CH_2)_3$— spacer (see 4a) is the most active, with increasing or decreasing spacer length resulting in reduced activity. Interestingly, the linked cyclitol with the shortest hydrocarbon spacer—compound 4f with a —$(CH_2)_2$— linker—is highly active in inhibiting aFGF binding to both heparin and HS but has no inhibitory activity against VEGF and is the least active linked cyclitol against bFGF. Furthermore, the more highly sulfated members of this series (ie, 5b and 5c) are less active against bFGF but 5c is quite a potent VEGF inhibitor, being comparable to PI-88. These data support the view that different heparan sulfate motifs bind to bFGF, aFGF and VEGF. Finally, a number of sulfated linked cyclitols have been identified that exhibit a broad range of inhibitory activities and are equal, if not superior, to PI-88: eg, 4e, 5l and 5d.

The data of Table 4 also show that a biosensor assay can be used to measure the binding of the chemokine IL-8 to HS or heparin. It was found that using 68 nM IL-8, 1 μM PI-88 was virtually unable to inhibit IL-8 binding to heparin (10% inhibition) or heparan sulfate (0% inhibition). On the other hand, 1 μM heparin essentially completely inhibited the binding of IL-8 to heparin (95%) and heparan sulfate (77%), with heparin having an $IC_{50}$ of 8 nM for the IL-8-heparin interaction and 63 nM for the IL-8-heparan sulfate interaction. However, all of the linked cyclitols exhibited considerable inhibitory activity at 1 μM with the less sulfated linked cyclitol with a —$(CH_2)_8$— hydrocarbon spacer being almost as active as heparin at inhibiting IL-8 binding (see the results for compound 4i). Of the more highly sulfated, linked cyclitols tested, the compound with a —$(CH_2)_{10}$— spacer was the most inhibitory (see the results for compound 5c). Since IL-8 is an important mediator of inflammation and angiogenesis, the IL-8 antagonists have clinical applications in treating inflammation- and angiogenesis-related disorders.

TABLE 4

Inhibition of Effector Binding

| Compound | Inhibition of Binding | | | |
|---|---|---|---|---|
| | bFGF | aFGF | VEGF | IL-8 |
| PI-88 | 56% (HS) | 33% (HS) | 65% (HS) | 0% (HS) |
| | IC50 = 0.025 μM | IC50 = ND | IC50 = ND | IC50 = ND |
| | 50% (Hep) | 96% (Hep) | 29% (Hep) | 10% (Hep) |
| | IC50 = 0.034 μM | IC50 = ND | IC50 = ND | IC50 = ND |
| 4f | 19% (HS) | 68% (HS) | 0% (HS) | 38% (HS) |
| | IC50 = 0.24 μM | IC50 = ND | IC50 = ND | IC50 = ND |
| | 15% (Hep) | 65% (Hep) | 0% (Hep) | 48% (Hep) |
| | IC50 > 0.25 μM | IC50 = ND | IC50 = ND | IC50 = ND |
| 4a | 29% (HS) | 73% (HS) | 4% (HS) | 38% (HS) |
| | IC50 = 0.11 μM | IC50 = ND | IC50 = ND | IC50 = ND |
| | 20% (Hep) | 74% (Hep) | 5% (Hep) | 48% (Hep) |
| | IC50 > 0.25 μM | IC50 = ND | IC50 = ND | IC50 = ND |
| 4g | 44% (HS) | 43% (HS) | 10% (HS) | 42% (HS) |
| | IC50 = ND | IC50 = ND | IC50 = ND | IC50 = ND |
| | 31% (Hep) | 44% (Hep) | 21% (Hep) | 67% (Hep) |
| | IC50 > 0.25 μM | IC50 = ND | IC50 = ND | IC50 = ND |
| 4k | 45% (HS) | 39% (HS) | 30% (HS) | 54% (HS) |
| | IC50 = ND | IC50 = ND | IC50 = ND | IC50 = ND |
| | 36% (Hep) | 43% (Hep) | 41% (Hep) | 67% (Hep) |
| | IC50 = ND | IC50 = ND | IC50 = ND | IC50 = ND |

TABLE 4-continued

Inhibition of Effector Binding

| Compound | Inhibition of Binding | | | |
|---|---|---|---|---|
| | bFGF | aFGF | VEGF | IL-8 |
| 4b | 48% (HS) | 47% (HS) | 32% (HS) | 48% (HS) |
| | IC50 = ND | IC50 = ND | IC50 = ND | IC50 = ND |
| | 52% (Hep) | 44% (Hep) | 45% (Hep) | 55% (Hep) |
| | IC50 = ND | IC50 = ND | IC50 = ND | IC50 = ND |
| 4h | 48% (HS) | 30% (HS) | 55% (HS) | 54% (HS) |
| | IC50 = ND | IC50 = ND | IC50 = ND | IC50 = ND |
| | 40% (Hep) | 28% (Hep) | 68% (Hep) | 52% (Hep) |
| | IC50 = ND | IC50 = ND | IC50 = ND | IC50 = ND |
| 4i | 51% (HS) | 28% (HS) | 71% (HS) | 89% (HS) |
| | IC50 = ND | IC50 = ND | IC50 = ND | IC50 = ND |
| | 45% (Hep) | 30% (Hep) | 70% (Hep) | 95% (Hep) |
| | IC50 = ND | IC50 = ND | IC50 = ND | IC50 = ND |
| 4j | 43% (HS) | 31% (HS) | 54% (HS) | 65% (HS) |
| | IC50 = ND | IC50 = ND | IC50 = ND | IC50 = ND |
| | 46% (Hep) | 31% (Hep) | 64% (Hep) | 62% (Hep) |
| | IC50 = ND | IC50 = ND | IC50 = ND | IC50 = ND |
| 4c | 43% (HS) | 21% (HS) | 53% (HS) | 77% (HS) |
| | IC50 = ND | IC50 = ND | IC50 = ND | IC50 = ND |
| | 34% (Hep) | 26% (Hep) | 62% (Hep) | 76% (Hep) |
| | IC50 = ND | IC50 = ND | IC50 = ND | IC50 = ND |
| 4d | 68% (HS) | 65% (HS) | 40% (HS) | 50% (HS) |
| | IC50 = 0.023 μM | IC50 = ND | IC50 = ND | IC50 = ND |
| | 52% (Hep) | 65% (Hep) | 44% (Hep) | 57% (Hep) |
| | IC50 = 0.032 μM | IC50 = ND | IC50 = ND | IC50 = ND |
| 4e | 61% (HS) | 63% (HS) | 51% (HS) | 65% (HS) |
| | IC50 = ND | IC50 = ND | IC50 = ND | IC50 = ND |
| | 49% (Hep) | 66% (Hep) | 63% (Hep) | 62% (Hep) |
| | IC50 = ND | IC50 = ND | IC50 = ND | IC50 = ND |
| 4l | 43% (HS) | 47% (HS) | 0% (HS) | 46% (HS) |
| | IC50 = ND | IC50 = ND | IC50 = ND | IC50 = ND |
| | 34% (Hep) | 54% (Hep) | 0% (Hep) | 52% (Hep) |
| | IC50 = ND | IC50 = ND | IC50 = ND | IC50 = ND |
| Polysulfated derivative of compound 25 | 54% (HS) IC50 = ND | 73% (HS) IC50 = ND | 21% (HS) IC50 = ND | 54% (HS) IC50 = ND |
| | 43% (Hep) | 88% (Hep) | 28% (Hep) | 52% (Hep) |
| | IC50 = ND | IC50 = ND | IC50 = ND | IC50 = ND |
| 5l | 43% (HS) | 54% (HS) | 11% (HS) | 42% (HS) |
| | IC50 = ND | IC50 = ND | IC50 = ND | IC50 = ND |
| | 33% (Hep) | 67% (Hep) | 13% (Hep) | 52% (Hep) |
| | IC50 = ND | IC50 = ND | IC50 = ND | IC50 = ND |
| 5b | 22% (HS) | 65% (HS) | 40% (HS) | 50% (HS) |
| | IC50 = 0.096 μM | IC50 = ND | IC50 = ND | IC50 = ND |
| | 15% (Hep) | 62% (Hep) | 53% (Hep) | 57% (Hep) |
| | IC50 > 0.25 μM | IC50 = ND | IC50 = ND | IC50 = ND |
| 5c | 14% (HS) | 36% (HS) | 46% (HS) | 88% (HS) |
| | IC50 > 0.25 μM | IC50 = ND | IC50 = ND | IC50 = ND |
| | 15% (Hep) | 20% (Hep) | 64% (Hep) | 86% (Hep) |
| | IC50 > 0.25 μM | IC50 = ND | IC50 = ND | IC50 = ND |
| 5d | 48% (HS) | 67% (HS) | 39% (HS) | 62% (HS) |
| | IC50 = 0.038 μM | IC50 = ND | IC50 = ND | IC50 = ND |
| | 35% (Hep) | 72% (Hep) | 54% (Hep) | 71% (Hep) |
| | IC50 = 0.16 μM | IC50 = ND | IC50 = ND | IC50 = ND |
| Sucrose octasulfate | 2.5% (HS) IC50 = 0.925 μM | 0% (HS) IC50 = ND | 0% (HS) IC50 = ND | ND |
| | 0% (Hep) IC50 > 1 μM | 0% (Hep) IC50 = ND | 0% (Hep) IC50 = ND | ND |
| Heparin (lung) | 68% (HS) IC50 = ND | 99% (HS) IC50 = ND | 84% (HS) IC50 = ND | 77% (HS) IC50 = 0.063 μM |
| | 13% (Hep) IC50 = ND | 97% (Hep) IC50 = ND | 66% (Hep) IC50 = ND | 95% (Hep) IC50 = 0.008 μM |

Figure 2:
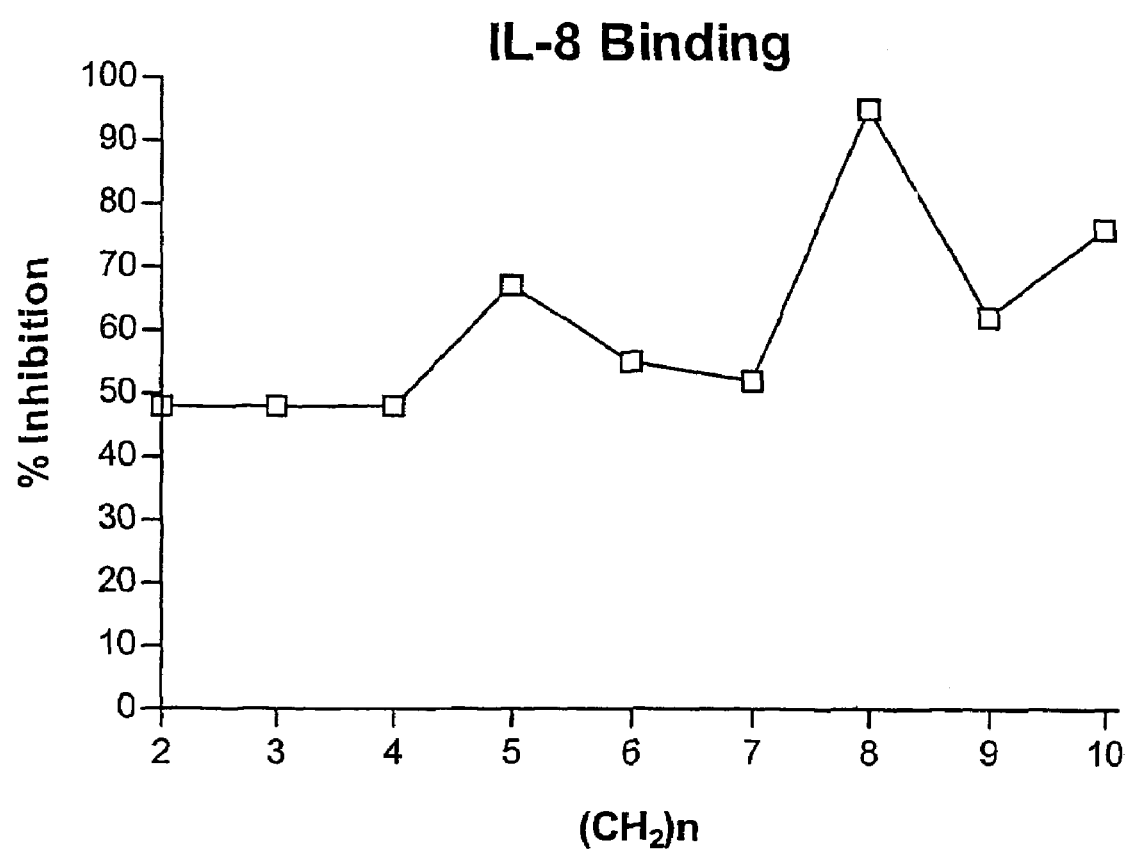
Figure 3:
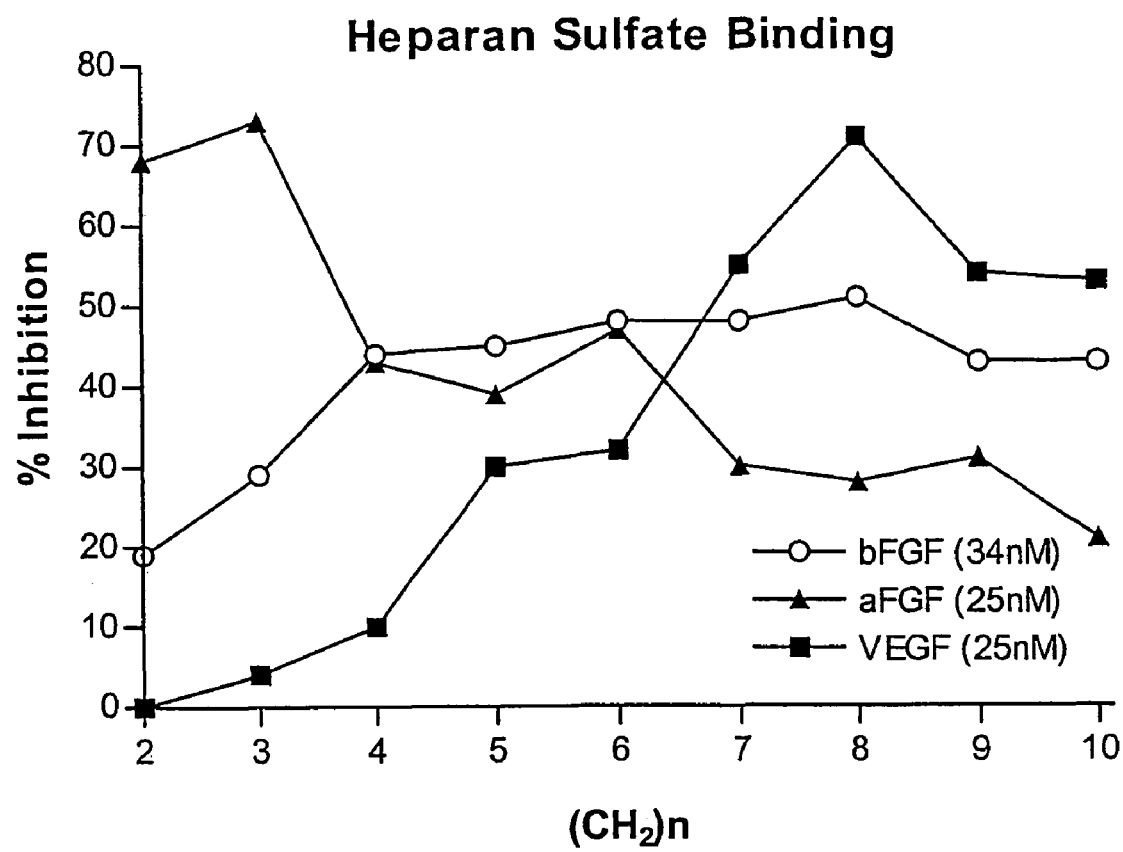

For ease of comparison, the inhibitory activities of linked cyclitols with increasing linker length are presented in FIGS. 1 to 3. The results presented in the figures are for inhibition of effector binding by compound 4f through to compound 4c in Table 4.

EXAMPLE 18

Angiogenesis Inhibition by Linked-Cyclitol Compounds

The ability of linked cyclitol compounds to inhibit angiogenesis in vitro was conducted using the assay essentially as described in the present applicant's International Patent Application No. PCT/AU95/00105 (Publication No. WO 95/23968), the entire content of which is incorporated herein by cross reference. The only changes to the procedure described in PCT/AU95/00105 were that the assays were conducted using rat aorta fragments rather than human placental vessel fragments.

The results of the angiogenesis inhibition assays are presented in Table 5. All potential inhibitors were tested at 100 µg/ml with PI-88 also being tested at 10 µg/ml. The tabulated data represent means of 4 culture wells for each experiment. Significant inhibition of angiogenesis is indicated with a single asterisk while double asterisks denote highly significant inhibition.

In Table 5, the same compound identifications as given in Table 3 have been used. The compounds were also tested at the same purity as in Example 15 save that the second entries for 4b and 4j relate to data obtained with higher purity compounds than the compounds used for the first data entries of each.

The results presented in Table 5 show that many of the heparinoid mimetics tested are inhibitors of angiogenesis (those exhibiting significant inhibition being marked by an asterisk or asterisks as indicated above) with the compound having a —(CH$_2$)$_4$— linker being the most potent.

TABLE 5

Angiogenesis Inhibition Results

| Compound | Number of experiments | % Growth |
| --- | --- | --- |
| Control | 7 | 90 |
| PI-88 | 7 | 45** |
| PI-88 (10 µg/ml) | 3 | 64* |
| 4f | 3 | 72 |
| 4a | 2 | 64* |
| 4g | 2 | 40** |
| 4k | 2 | 51* |
| 4b | 2 | 70 |
| 4b | 2 | 65* |
| 4h | 2 | 52* |
| 4i | 2 | 50* |
| 4j | 1 | 68 |
| 4j | 2 | 56* |
| 4c | 3 | 56* |
| 4d | 1 | 67 |
| 4e | 1 | 55* |
| 4l | 1 | 75 |
| Polysulfated derivative of compound 25 | 1 | 73 |
| 5l | 1 | 80 |
| 5b | 1 | 50* |
| 5c | 1 | 60* |
| 5e | 1 | 60* |

EXAMPLE 19

Anticoagulant Activity of Linked-Cyclitol Compounds

To determine the in vitro anticoagulation activity of the linked cyclitol compounds, prolongation of activated partial thromboplastin time (APTT), and Celite™-activated clotting time (ACT) were measured.

Methods

APTT

Test compounds were dissolved in saline and added to pooled normal human plasma in a 1:10 dilution, and then diluted serially with plasma starting with a concentration of 100 µg/ml. Immediately following dilution preparation, 100 µl of APTT reagent was added to 100 µL of test plasma and incubated for 5 minutes at 370° C. Clotting time was measured using a Fibrometer (BBL, Cockeysville, Md.) following the addition of 100 µl of pre-warmed 0.025 M CaCl$_2$. Measurement of clotting time was stopped at 300 seconds as clotting times beyond 300 seconds are outside the linear range of the instrument.

Reagents (0.025 M CaCl$_2$ and micronized silica based APTT reagent) were obtained from BioMerieux (Durham, N.C.). The reagents were reconstituted in 5 ml of sterile deionized water, and stored for no more than one week at 4° C.

ACT

Stock solutions of linked cyclitol compounds were made at 1,000 µg/ml in saline. A 0.5 ml aliquot from each stock was added to a 5 ml polypropylene syringe. Using a technique to discard the first 5 ml, blood was drawn from normal healthy volunteers via the antecubital vein to the 5 ml mark to give final concentrations of agent 1/10 of the relevant stock solution. The syringes were inverted to mix the blood and the test compound, then 2 ml of the mixture transferred to a Celitem-containing tube which was placed into a Hemochron ACT machine for measurement of clotting time.

Figure 4:
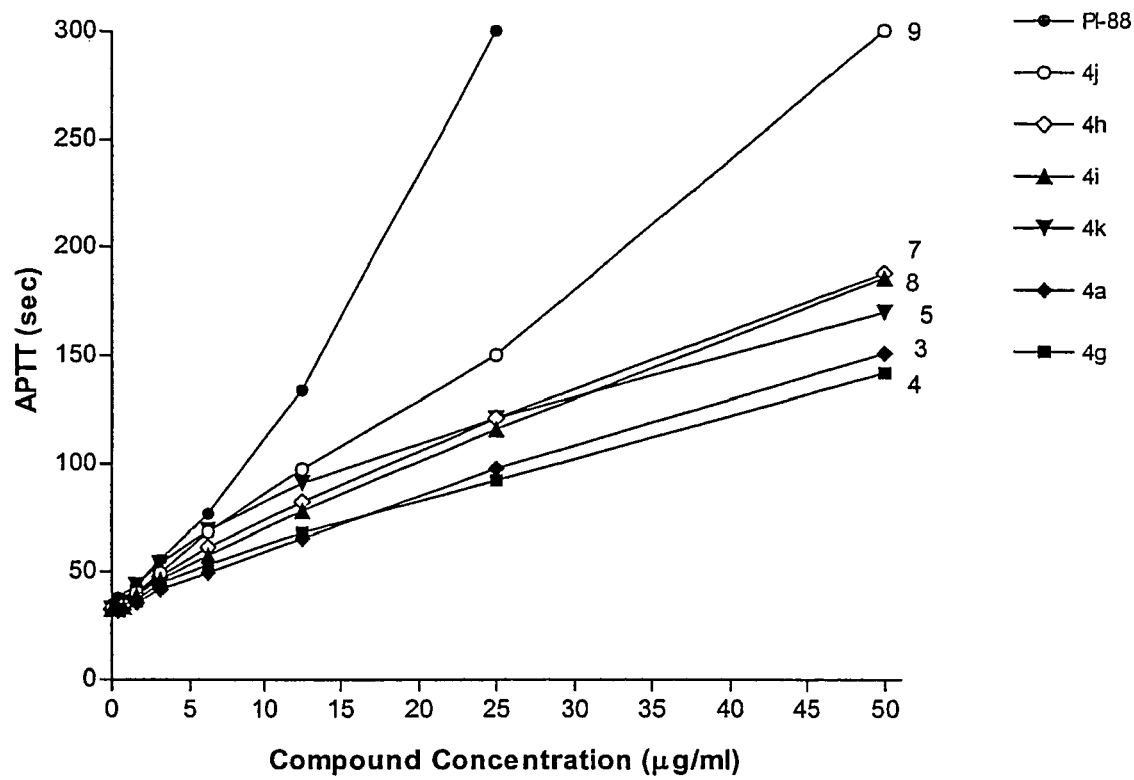
FIG. 4 comprises plots of clotting time in seconds against the concentration of the linked cyclitol compound under test in an activated partial thromboplastin time assay.
Figure 5:
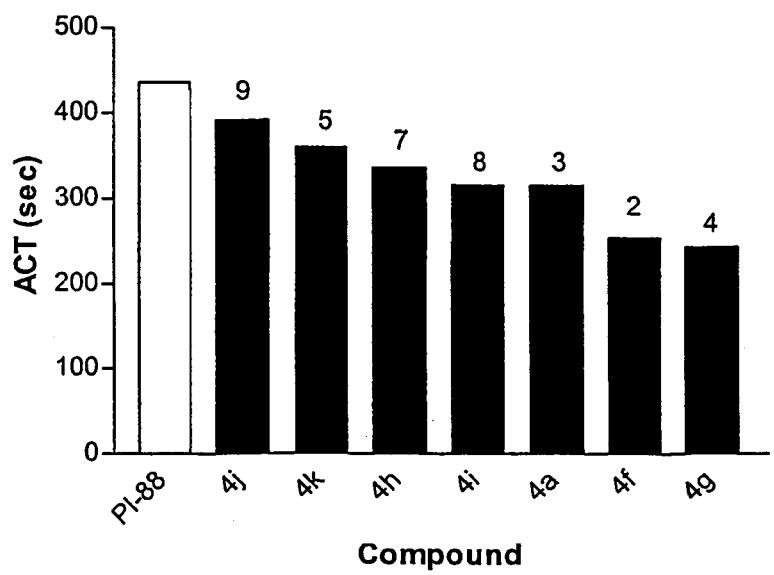
FIG. 5 comprises bar graphs of the clotting time in seconds in activated clotting time assay mixtures including the linked cyclitol compounds of the invention.

The results of the APTT and ACT experiments are presented in FIGS. 4 and 5, respectively. In these figures, the numbers at the ends of plots or above bars are the linker lengths of the compounds tested.

Results

FIGS. 4 and 5 clearly show that as the length of the linker increases, the linked cyclitol compounds generally have greater activity as anticoagutants.

It will be appreciated by those of skill in the art that many changes can be made to the compounds, the processes for preparing them, and their uses as exemplified above without departing from the broad ambit and scope of the invention.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

The reference to the publications cited in the "Background of the Invention" section of this specification is not an admission that the disclosures constitute common general knowledge in Australia.

The invention claimed is:

1. A compound of the formula

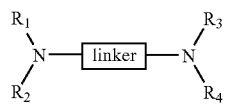

wherein:
R$_1$, R$_2$, R$_3$ and R$_4$ are independently a substituted or unsubstituted cyclitol with a ring comprising six carbon atoms, or hydrogen, substituted or unsubstituted alkyl, cycloalkyl, aryl, acyl, alkyloxycarbonyl, or alkylaminocarbonyl, with the proviso that at least two of R$_1$, R$_2$, R$_3$ and R$_4$ comprise said substituted or unsubstituted cyclitol; or $R_1$ and $R_3$ are independently a substituted or unsubstituted cyclitol carbamide with a ring comprising six carbon atoms with the linker bond at the carbamide nitrogen, and $R_2$ and $R_4$ are independently hydrogen, substituted or unsubstituted alkyl, cycloalkyl or aryl; and the linker is selected from the group consisting of $-(CH_2)_w-$, $-(CH_2)_x-C_6H_4-(CH_2)_x-$, $-(CH_2)_y-NR_5-(CH_2)_y-$, and $-(CH_2)_z-HCR_6-(CH_2)_z-$; wherein: x is an integer having a value of 1–10 and w, y and z are independently an integer having a value of 0–10; $R_5$ is a substituted or unsubstituted cyclitol with a ring comprising six carbon atoms; and, wherein x is independently an integer having a value of 1–10 $R_6$ is $-OH$, $-OSO_3Na$, $-OSO_3Na$ substituted with alkyl, cycloalkyl or aryl, or substituted or unsubstituted alkyl, cycloalkyl or aryl; and wherein each substituent on said substituted cyclitol is independently selected from:

(a) phosphoryl groups such as phosphate, thiophosphate $-O-P(S)(OH)_2$; phosphate esters $-O-P(O)(OR)_2$; thiophosphate esters $-O-P(S)(OR)_2$; phosphonate $-O-P(O)OHR$; thiophosphonate $-O-P(S)OHR$; substituted phosphonate $-O-P(O)OR_1R_2$; substituted thiophosphonate $-O-P(S)OR_1R_2$; $-O-P(S)(OH)(SH)$; and cyclic phosphate;

(b) other phosphorus containing compounds such as phosphoramidite $-O-P(OR)-NR_1R_2$; and phosphoramidate $-O-P(O)(OR)-NR_1R_2$;

(c) sulphur groups such as $-O-S(O)(OH)$, $-O-S(O)_2(OH)$, $RO-S(O)_3^-$, $-SH$, $-SR$, $-S(\rightarrow O)-R$, $S(O)_2R$, $RO-S(O)_2^-$, $-O-SO_2NH_2$, $-O-SO_2R_1R_2$ or sulphamide $-NHSO_2NH_2$;

(d) amino groups such as $-NHR$, $-NR_1R_2$, $-NHAc$, $-NHCOR$, $-NH-O-COR$, $-NHSO_3$, $-NHSO_2R$, $-N(SO_2R)_2$, and/or amidino groups such as $-NH-C(=NH)NH_2$ and/or ureido groups such as $-NH-CO-NR_1R_2$ or thiouriedo groups such as $-H-C(S)-NH_2$;

(e) substituted hydroxy groups such as $-OR_3$, where $R_3$ is $C_{1-10}$ unsubstituted or substituted alkyl, alkoxyalkyl, aryloxyalkyl, cycloalkyl, alkenyl (unsubstituted alkyl), alkylene ($C_{3-7}$ cycloalkyl), $-OCOR$, aryl, heteroaryl, acetal, or where two hydroxyl groups are joined as a ketal;

(f) a halogen;

(g) a cyclitol or substituted cyclitol as defined above; or (h) a physiologically acceptable salt of any of the above;

wherein in (a) to (g) above R, $R_1$ and $R_2$ are independently hydrogen or $C_{1-10}$ unsubstituted or substituted alcyl or aryl;

with the proviso that when each $R_1$ and $R_3$ are H and $R_4$ are cyclitols, each cyclitol being independently substituted with one amino group, then the linker is not $-CH_2C_6H_4CH_2-$.

2. A compound according to claim 1 having a structure selected from:

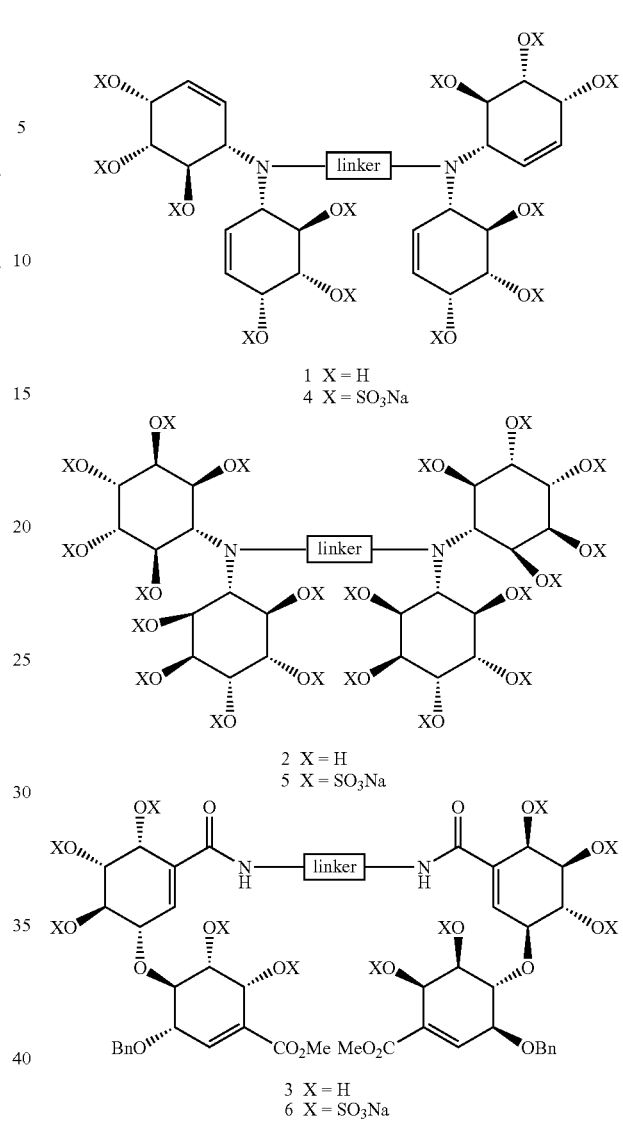

1 X = H
4 X = SO$_3$Na

2 X = H
5 X = SO$_3$Na

3 X = H
6 X = SO$_3$Na wherein the linker is selected from the group consisting of $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, m-$C_6H_4-$, p-$C_6H_4-$, m-$(CH_2)-C_6H_4-(CH_2)-$ and p-$(CH_2)-C_6H_4-(CH_2)-$.

3. A compound according to claim 1, the compound having the structure:

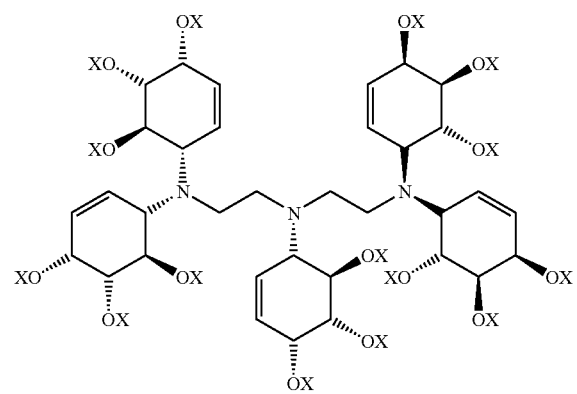

where X is SO$_3$Na.

4. A process for preparing a compound comprising linked cyclitol residues, which process comprises the steps of:
i) reacting a substituted or unsubstituted epoxide of the formula

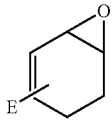

with a 1,ω-diol or a 1,ω-diamine, wherein E is an electrophilic moiety and said substituents on said epoxide comprise at least one group selected from a protected or unprotected hydroxyl or amino group;
ii) if necessary, deprotecting the linked cyclitol compound formed in step (i); and, optionally,
iii) sulphating the compound formed in step (ii).

5. The process according to claim 4, wherein said electrophilic group is a halo group, a carboxyl group, a derivatised carboxyl group, a cyano group, a nitro group, a sulfoxide group, a sulfonate group, a halo-substituted alkyl group, an acyl- or aryl-substituted amino group, a sulfhydryl groups, a phenyl group or a substituted phenyl group.

6. The process according to claim 4, wherein said epoxide has the following structure:

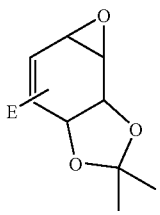

in which E is a halo group, a carboxyl group, a derivatised carboxyl group, a cyano group, a nitro group, a sulfoxide group or a sulfonate group.

7. The process according to claim 4, wherein said epoxide has the following structure:

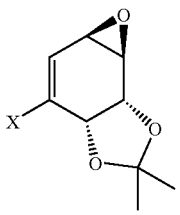

in which X is a halo group, a carboxyl group, or a derivatised carboxyl group.

8. The process according to claim 7, wherein said halo group is bromo, chloro or iodo.

9. The process according to claim 4, wherein said process includes a further step selected from:
Pd[0]-mediated carbomethoxylation of the linked cyclitol compound;
acetylation of the linked cyclitol compound;
dehalogenation of the linked cyclitol compound; and
hydroxylation of the linked cyclitol compound.

10. The process according to claim 4, wherein step (i) is carried out at room temperature to 80° C.

11. The process according to claim 4, wherein step (i) is carried out at about 110° C.

12. The process according to claim 4, wherein step (i) is carried out at about 120° C.

13. The process according to claim 4, wherein step (i) is carried out at 5–19 kbar.

14. A pharmaceutical or veterinary composition for the prevention or treatment in a mammalian subject of a disorder resulting from angiogenesis, tumour metastasis, inflammation and/or coagulation/thrombosis, which composition comprises at least one compound according to claim 1 together with a pharmaceutically or veterinarially acceptable carrier or diluent for said at least one compound.

15. The composition according to claim 14 which further includes a pharmaceutically or veterinarially acceptable excipient, buffer, stabiliser, isotonicising agent, preservative or anti-oxidant.

16. The composition according to claim 14, wherein said compound is present therein as an ester, a free acid or base, a hydrate, or a prodrug.

17. A method for the treatment in a mammalian subject of a disorder resulting from angiogenesis, tumour metastasis, inflammation and/or coagulation/thrombosis, which method comprises administering to the subject an effective amount of at least one compound according claim 1, or a composition comprising said at least one compound.

18. The method according to claim 17, wherein said mammalian subject is a human subject.

19. The method according to claim 17, wherein said disorder resulting from angiogenesis is a proliferative retinopathy or angiogenesis resulting from the growth of a solid tumour.

20. The method according to claim 17, wherein said disorder resulting from inflammation is rheumatoid arthritis, multiple sclerosis, inflammatory bowel disease, allograft rejection or chronic asthma.

21. The method according to claim 17, wherein said disorder resulting from coagulation and/or thrombosis is deep venous thrombosis, pulmonary embolism, thrombotic stroke, peripheral arterial thrombosis, unstable angina or myocardial infarction.

* * * * *